United States Patent
Wang et al.

(10) Patent No.: US 11,149,253 B2
(45) Date of Patent: Oct. 19, 2021

(54) SMALL MOLECULE COMPOUND COMBINATION FOR REPROGRAMMING DIGESTIVE TRACT DERIVED EPITHELIAL CELLS TO ENDODERMAL STEM/PROGENITOR CELLS, REPROGRAMMING METHOD AND APPLICATION

(71) Applicant: INSTITUE OF TRANSFUSION MEDICINE, ACADEMY OF MILITARY MEDICAL SCIENCES, PEOPLE'S LIBRATION ARMY OF CHINA, Beijing (CN)

(72) Inventors: Yunfang Wang, Beijing (CN); Shuyong Wang, Beijing (CN); Wencheng Zhang, Beijing (CN); Jinhua Qin, Beijing (CN); Xuan Wang, Beijing (CN); Mingyang Chang, Beijing (CN); Fang Yan, Beijing (CN); Xuetao Pei, Beijing (CN)

(73) Assignee: INSTITUTE OF TRANSFUSION MEDICINE, ACADEMY OF MILITARY MEDICAL SCIENCES, PEOPLE'S LIBRATION ARMY OF CHINA, Beijing (CN)

( * ) Notice: Subject to any disclaimer, the term of this patent is extended or adjusted under 35 U.S.C. 154(b) by 465 days.

(21) Appl. No.: 16/306,646

(22) PCT Filed: May 27, 2017

(86) PCT No.: PCT/CN2017/086336
§ 371 (c)(1),
(2) Date: Jan. 9, 2019

(87) PCT Pub. No.: WO2017/206837
PCT Pub. Date: Dec. 7, 2017

(65) Prior Publication Data
US 2020/0385682 A1  Dec. 10, 2020

(30) Foreign Application Priority Data
Jun. 3, 2016  (CN) .......................... 201610391309.7

(51) Int. Cl.
C12N 5/073  (2010.01)
C12N 5/071  (2010.01)
A61P 35/00  (2006.01)

(52) U.S. Cl.
CPC ............ *C12N 5/0679* (2013.01); *A61P 35/00* (2018.01); *C12N 2501/11* (2013.01); *C12N 2501/115* (2013.01); *C12N 2501/999* (2013.01); *C12N 2506/45* (2013.01)

(58) Field of Classification Search
CPC .................................................. C12N 5/0679
See application file for complete search history.

(56) References Cited

U.S. PATENT DOCUMENTS

2012/0288936 A1  11/2012  Ahlfors et al.
2015/0322405 A1  11/2015  Han et al.

FOREIGN PATENT DOCUMENTS

| CN | 101445791 A   | 6/2009  |
| CN | 102959076 A   | 3/2013  |
| CN | 104120107 A   | 10/2014 |
| CN | 104673741 A   | 6/2015  |
| CN | 104694570 A   | 6/2015  |
| EP | 3 321 354 A1  | 5/2018  |
| WO | 2012/006577 A2| 1/2012  |
| WO | 2016/022992 A1| 2/2016  |

OTHER PUBLICATIONS

Bellin M.D. et al., "Potent Induction Immunotherapy Promotes Long-Term Insulin Independence After Islet Transplantation in Type 1 Diabetes", American Journal of Transplantation 12(6):1576-1583 (Jun. 2012).
Cheng X. et al., "Self-Renewing Endodermal Progenitor Lines Generated from Human Pluripotent Stem Cells", Cell Stem Cell 10:371-384 (Apr. 6, 2012).
Du Y. et al., "Human Hepatocytes With Drug Metabolic Function Induced from Fibroblasts by Lineage Reprogramming", Cell Stem Cell 14:394-403 (Mar. 6, 2014).
Gouon-Evans V. et al., "BMP-4 is Required for Hepatic Specification of Mouse Embryonic Stem Cell-Derived Definitive Endoderm", Nature Biotechnology 24(11):1402-1411 (Nov. 2006).
Hou P. et al., "Pluripotent Stem Cells Induced from Mouse Somatic Cells by Small-Molecule Compounds", Science 341:651-654 (Aug. 9, 2013).
Huang P. et al., "Direct Reprogramming of Human Fibroblasts to Functional and Expandable Hepatocytes", Cell Stem Cell 14:370-384 (Mar. 6, 2014).
Huang P. et al., "Induction of Functional Hepatocyte-Like Cells from Mouse Fibroblasts by Defined Factors", Nature 474:386-389 (Jul. 21, 2011).

(Continued)

*Primary Examiner* — Scott Long
(74) *Attorney, Agent, or Firm* — Scully, Scott, Murphy & Presser, P.C.

(57) ABSTRACT

Provided are a small molecule compound combination for reprogramming digestive tract derived epithelial cells to endodermal stem/progenitor cells, a reprogramming method and an application. Human gastric epithelial cells (hGECs) are used as initiating cells, human gastric subepithelial myofibroblasts (aGSEMFs) are used as a trophoblast, a compound combination having all or a plurality of FBP, Bay K 8644, Bix01294, SB431542 or A813-01, VPA, RG108, PD0325901 and PS48 including SB or A83 is used to reprogram digestive tract derived epithelial cells to endodermal stem/progenitor cells, and the endodermal stem/progenitor cells can be used for inducing differentiation towards liver cells, pancreatic beta cells and intestinal cells.

19 Claims, 21 Drawing Sheets
Specification includes a Sequence Listing.

(56) References Cited

OTHER PUBLICATIONS

Hu W. et al., "Direct Conversion of Normal and Alzheimer's Disease Human Fibroblasts into Neuronal Cells by Small Molecules", Cell Stem Cell 17:204-212 (Aug. 6, 2015).
Kubota H. et al., "Clonogenic Hepatoblasts, Common Precursors for Hepatocytic and Biliary Lineages, are Lacking Classical Major Histocompatibility Complex Class I Antigen", PNAS 97(22):12132-12137 (Oct. 24, 2000).
Li X. et al., "Small-Molecule-Driven Direct Reprogramming of Mouse Fibroblasts into Functional Neurons", Cell Stem Cell 17:195-203 (Aug. 6, 2015).
Li K. et al., "Small Molecules Facilitate the Reprogramming of Mouse Fibroblasts into Pacreatic Lineages", Cell Stem Cell 14:228-236 (Feb. 6, 2014).
Li W. et al., "Chemical Approaches to Stem Cell Biology and Therapeutics", Cell Stem Cell 13:270-283 (Sep. 5, 2013).
Li R. et al., "A Mesenchymal-to-Epithelial Transition Initiates and is Required for the Nuclear Reprogramming of Mouse Fibroblasts", Cell Stem Cell 7:1-13 (Jul. 2, 2010).
Longmire T.A. et al., "Efficient Derivation of Purified Lung and Thyroid Progenitors from Embryonic Stem Cells", Cell Stem Cell 10:398-411 (Apr. 6, 2012).
Murry C.E. et al., "Differentiation of Embryonic Stem Cells to Clinically Relevant Populations: Lessons from Embryonic Development", Cell 132:661-680 (Feb. 22, 2008).
Pagliuca F.W. et al., "Generation of Functional Human Pancreatic β Cells In Vitro", Cell 159(2):428-439 (Oct. 9, 2014).
Rezania A. et al., "Reversal of Diabetes With Insulin-Producing Cells Derived In Vitro from Human Pluripotent Stem Cells", Nature Biotechnology 32(11):1121-1133 (Nov. 2014).
Sancho-Martinez I. et al., "Lineage Conversion Methodologies Meet the Reprogramming Toolbox", Nature Cell Biology 14(9):892-899 (Sep. 2012).
Sneddon J.B. et al., "Self-Renewal of Embryonic-Stem-Cell-Derived Progenitors by Organ-Matched Mesenchyme", Nature 491(7426):765-768 (Nov. 29, 2012).
Spence J.R. et al., "Directed Differentiation of Human Pluripotent Stem Cells into Intestinal Tissue In Vitro", Nature 470(7332):105-109 (Feb. 3, 2011).
Takahashi K. et al., "Induction of Pluripotent Stem Cells from Adult Human Fibroblasts by Defined Factors", Cell 131:861-872 (Nov. 30, 2007).
Takahashi K. et al., "Induction of Pluripotent Stem Cells from Mouse Embryonic and Adult Fibroblast Cultures by Defined Factors", Cell 126:663-676 (Aug. 25, 2006).
Thomson J.A. et al., "Embryonic Stem Cell Lines Derived from Human Blastocysts", Science 282:1145-1147 (Nov. 6, 1998).
Vierbuchen T. et al., "Direct Conversion of Fibroblasts to Functional Neurons by Defined Factors", Nature 463:1035-1041 (Feb. 25, 2010).
Wang Y. et al., "Conversion of Human Gastric Epithelial Cells to Multipotent Endodermal Progenitors Using Defined Small Molecules", Cell Stem Cell 19:449-461 (Oct. 6, 2016).
Wang F-S et al., "The Global Burden of Liver Disease: The Major Impact of China", Hepatology 60:2099-2108 (Dec. 2014).
Watson C.L. et al., "An In Vivo Model of Human Small Intestine Using Pluripotent Stem Cells", Nat Med. 20(11):1310-1314 (Nov. 2014).
Yu B. et al., "Reprogramming Fibroblasts into Bipotential Hepatic Stem Cells by Defined Factors", Cell Stem Cell 13:1-13 (Sep. 5, 2013).
Zhang L. et al., "Small Molecules Efficiently Reprogram Human Astroglial Cells into Functional Neurons", Cell Stem Cell 17:735-747 (Dec. 3, 2015).
Zhou Q. et al., "In Vivo Reprogramming of Adult Pancreatic Exocrine Cells to β-Cells", Nature 455:627-632 (Oct. 2, 2008).
Zhu S. et al., "Human Pancreatic Beta-Like Cells Converted from Fibroblasts", Nature Communications 7: DOI.10.1038/ncomms10080 (Jan. 6, 2016).
Zhu S. et al., "Mouse Liver Repopulation With Hepatocytes Generated from Human Fibroblasts", Nature 508 (7494):93-97 (Apr. 3, 2014) (Author manuscript: available in PMC Oct. 3, 2014).
International Search Report dated Aug. 25, 2017 received in International Application No. PCT/CN2017/086336, together with an English-language translation.
Asadi S. et al., "Comparing the Effects of Small Molecules BIX-01294, Bay K8644, RG-108 and Valproic Acid, and Their Different Combinations on Induction of Pluripotency Marker-Genes by Oct4 in The Mouse Brain", Cell Journal 16 (4):416-425 (2015).
Xu A. et al., "Chemical Transdifferentiation: Closer to Regenerative Medicine", Front. Med. 10(2):152-165 (2016).

(Red fluorescence)  (Green fluorescence)  (Upper green, lower red)

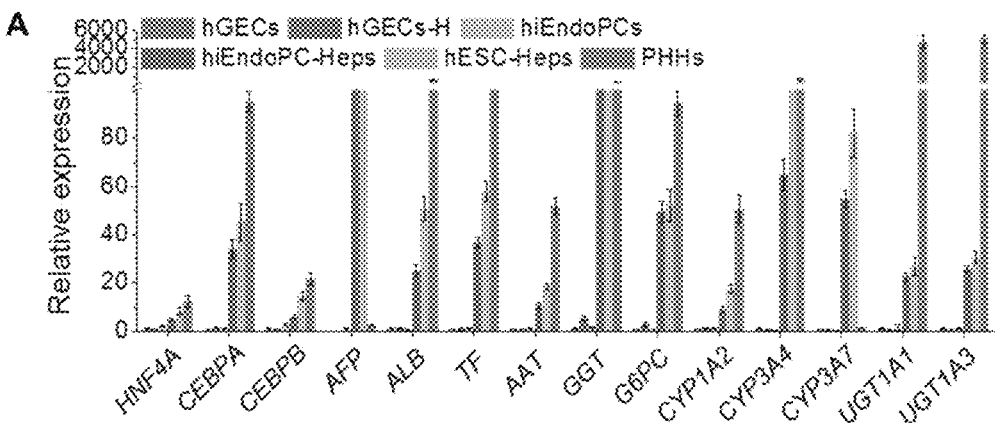
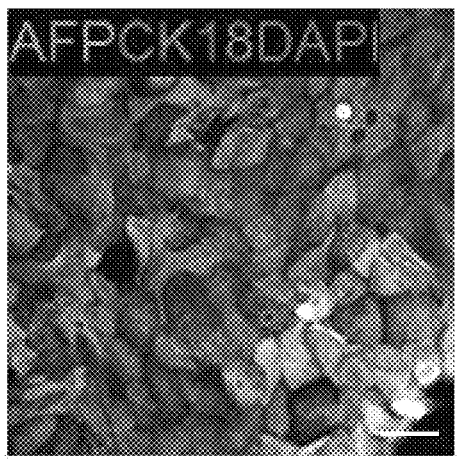
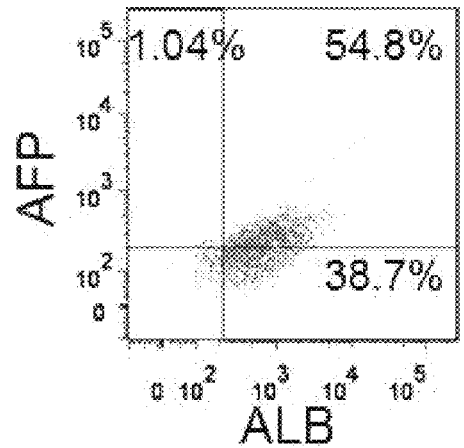
Figures 35A-35C
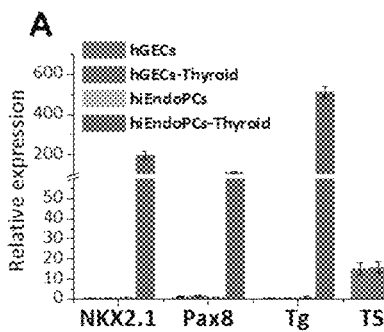
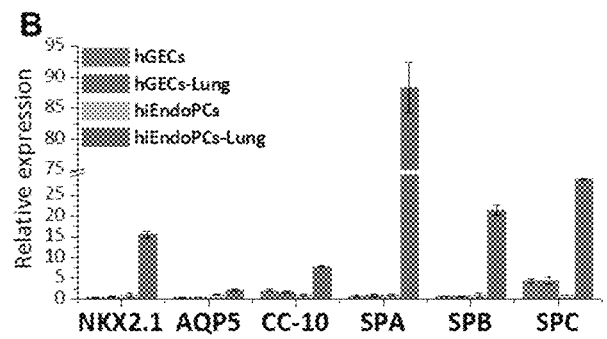
Figures 36A-36B under US 11,149,253 B2

SEQUENCE LISTING

<160> NUMBER OF SEQ ID NOS: 100

<210> SEQ ID NO 1

```
<211> LENGTH: 20
<212> TYPE: DNA
<213> ORGANISM: Artificial Sequence
<220> FEATURE:
<223> OTHER INFORMATION: Description of artificial sequence: Synthetic
      polynucleotides

<400> SEQUENCE: 1
gagtcaacgg atttggtcgt                                                   20

<210> SEQ ID NO 2
<211> LENGTH: 20
<212> TYPE: DNA
<213> ORGANISM: Artificial Sequence
<220> FEATURE:
<223> OTHER INFORMATION: Description of artificial sequence: Synthetic
      polynucleotides

<400> SEQUENCE: 2
ttgattttgg agggatctcg                                                   20

<210> SEQ ID NO 3
<211> LENGTH: 19
<212> TYPE: DNA
<213> ORGANISM: Artificial Sequence
<220> FEATURE:
<223> OTHER INFORMATION: Description of artificial sequence: Synthetic
      polynucleotides

<400> SEQUENCE: 3
gcgaccccaa gacctacag                                                    19

<210> SEQ ID NO 4
<211> LENGTH: 19
<212> TYPE: DNA
<213> ORGANISM: Artificial Sequence
<220> FEATURE:
<223> OTHER INFORMATION: Description of artificial sequence: Synthetic
      polynucleotides

<400> SEQUENCE: 4
ggttctgccg gtagaaggg                                                    19

<210> SEQ ID NO 5
<211> LENGTH: 21
<212> TYPE: DNA
<213> ORGANISM: Artificial Sequence
<220> FEATURE:
<223> OTHER INFORMATION: Description of artificial sequence: Synthetic
      polynucleotides

<400> SEQUENCE: 5
cccagacgtt ctcagtcagt g                                                 21

<210> SEQ ID NO 6
<211> LENGTH: 20
<212> TYPE: DNA
<213> ORGANISM: Artificial Sequence
<220> FEATURE:
<223> OTHER INFORMATION: Description of artificial sequence: Synthetic
      polynucleotides

<400> SEQUENCE: 6
gctgttccaa gagtcctgct                                                   20

<210> SEQ ID NO 7
<211> LENGTH: 24
```

<212> TYPE: DNA
<213> ORGANISM: Artificial Sequence
<220> FEATURE:
<223> OTHER INFORMATION: Description of artificial sequence: Synthetic
      polynucleotides

<400> SEQUENCE: 7
cgatctttgc gcagagggtg ctgt                                          24

<210> SEQ ID NO 8
<211> LENGTH: 22
<212> TYPE: DNA
<213> ORGANISM: Artificial Sequence
<220> FEATURE:
<223> OTHER INFORMATION: Description of artificial sequence: Synthetic
      polynucleotides

<400> SEQUENCE: 8
tttgcacgct gccaggcgta ag                                            22

<210> SEQ ID NO 9
<211> LENGTH: 20
<212> TYPE: DNA
<213> ORGANISM: Artificial Sequence
<220> FEATURE:
<223> OTHER INFORMATION: Description of artificial sequence: Synthetic
      polynucleotides

<400> SEQUENCE: 9
tgtacgcaca caagcaggaa                                               20

<210> SEQ ID NO 10
<211> LENGTH: 22
<212> TYPE: DNA
<213> ORGANISM: Artificial Sequence
<220> FEATURE:
<223> OTHER INFORMATION: Description of artificial sequence: Synthetic
      polynucleotides

<400> SEQUENCE: 10
gttggtgagt gtactgatgc tg                                            22

<210> SEQ ID NO 11
<211> LENGTH: 22
<212> TYPE: DNA
<213> ORGANISM: Artificial Sequence
<220> FEATURE:
<223> OTHER INFORMATION: Description of artificial sequence: Synthetic
      polynucleotides

<400> SEQUENCE: 11
agcagctcca gctcaggcga aa                                            22

<210> SEQ ID NO 12
<211> LENGTH: 20
<212> TYPE: DNA
<213> ORGANISM: Artificial Sequence
<220> FEATURE:
<223> OTHER INFORMATION: Description of artificial sequence: Synthetic
      polynucleotides

<400> SEQUENCE: 12
tggcgctcag tgaggttcag                                               20

<210> SEQ ID NO 13
<211> LENGTH: 21
<212> TYPE: DNA

<213> ORGANISM: Artificial Sequence
<220> FEATURE:
<223> OTHER INFORMATION: Description of artificial sequence: Synthetic
      polynucleotides

<400> SEQUENCE: 13
acaactggcc gaagaatagc a                                                    21

<210> SEQ ID NO 14
<211> LENGTH: 23
<212> TYPE: DNA
<213> ORGANISM: Artificial Sequence
<220> FEATURE:
<223> OTHER INFORMATION: Description of artificial sequence: Synthetic
      polynucleotides

<400> SEQUENCE: 14
ggaggaagct gacaacaatg aaa                                                  23

<210> SEQ ID NO 15
<211> LENGTH: 19
<212> TYPE: DNA
<213> ORGANISM: Artificial Sequence
<220> FEATURE:
<223> OTHER INFORMATION: Description of artificial sequence: Synthetic
      polynucleotides

<400> SEQUENCE: 15
agcgaacgca catcaagac                                                       19

<210> SEQ ID NO 16
<211> LENGTH: 21
<212> TYPE: DNA
<213> ORGANISM: Artificial Sequence
<220> FEATURE:
<223> OTHER INFORMATION: Description of artificial sequence: Synthetic
      polynucleotides

<400> SEQUENCE: 16
gctgtagtgt gggaggttga a                                                    21

<210> SEQ ID NO 17
<211> LENGTH: 22
<212> TYPE: DNA
<213> ORGANISM: Artificial Sequence
<220> FEATURE:
<223> OTHER INFORMATION: Description of artificial sequence: Synthetic
      polynucleotides

<400> SEQUENCE: 17
cttgaatccc gaatggaaag gg                                                   22

<210> SEQ ID NO 18
<211> LENGTH: 23
<212> TYPE: DNA
<213> ORGANISM: Artificial Sequence
<220> FEATURE:
<223> OTHER INFORMATION: Description of artificial sequence: Synthetic
      polynucleotides

<400> SEQUENCE: 18
gtgtatatcc cagggtgatc ctc                                                  23

<210> SEQ ID NO 19
<211> LENGTH: 21
<212> TYPE: DNA
<213> ORGANISM: Artificial Sequence

```
<220> FEATURE:
<223> OTHER INFORMATION: Description of artificial sequence: Synthetic
      polynucleotides

<400> SEQUENCE: 19
tacagcatgt cctactcgca g                                              21

<210> SEQ ID NO 20
<211> LENGTH: 21
<212> TYPE: DNA
<213> ORGANISM: Artificial Sequence
<220> FEATURE:
<223> OTHER INFORMATION: Description of artificial sequence: Synthetic
      polynucleotides

<400> SEQUENCE: 20
gaggaagagg taaccacagg g                                              21

<210> SEQ ID NO 21
<211> LENGTH: 20
<212> TYPE: DNA
<213> ORGANISM: Artificial Sequence
<220> FEATURE:
<223> OTHER INFORMATION: Description of artificial sequence: Synthetic
      polynucleotides

<400> SEQUENCE: 21
tcggaaggac tatcctgctg                                                20

<210> SEQ ID NO 22
<211> LENGTH: 21
<212> TYPE: DNA
<213> ORGANISM: Artificial Sequence
<220> FEATURE:
<223> OTHER INFORMATION: Description of artificial sequence: Synthetic
      polynucleotides

<400> SEQUENCE: 22
gtgtgttcgc ctcttgacat t                                              21

<210> SEQ ID NO 23
<211> LENGTH: 19
<212> TYPE: DNA
<213> ORGANISM: Artificial Sequence
<220> FEATURE:
<223> OTHER INFORMATION: Description of artificial sequence: Synthetic
      polynucleotides

<400> SEQUENCE: 23
ttaggatgtg gacgtaatt                                                 19

<210> SEQ ID NO 24
<211> LENGTH: 20
<212> TYPE: DNA
<213> ORGANISM: Artificial Sequence
<220> FEATURE:
<223> OTHER INFORMATION: Description of artificial sequence: Synthetic
      polynucleotides

<400> SEQUENCE: 24
ggtcaagttc aacatgacag                                                20

<210> SEQ ID NO 25
<211> LENGTH: 22
<212> TYPE: DNA
<213> ORGANISM: Artificial Sequence
<220> FEATURE:
```

```
<223> OTHER INFORMATION: Description of artificial sequence: Synthetic
      polynucleotides

<400> SEQUENCE: 25
atgcagcgac tatgtgtgta tg                                              22

<210> SEQ ID NO 26
<211> LENGTH: 19
<212> TYPE: DNA
<213> ORGANISM: Artificial Sequence
<220> FEATURE:
<223> OTHER INFORMATION: Description of artificial sequence: Synthetic
      polynucleotides

<400> SEQUENCE: 26
gcccctgtac ctaagggtg                                                  19

<210> SEQ ID NO 27
<211> LENGTH: 21
<212> TYPE: DNA
<213> ORGANISM: Artificial Sequence
<220> FEATURE:
<223> OTHER INFORMATION: Description of artificial sequence: Synthetic
      polynucleotides

<400> SEQUENCE: 27
actcatggag aactcggtga c                                               21

<210> SEQ ID NO 28
<211> LENGTH: 21
<212> TYPE: DNA
<213> ORGANISM: Artificial Sequence
<220> FEATURE:
<223> OTHER INFORMATION: Description of artificial sequence: Synthetic
      polynucleotides

<400> SEQUENCE: 28
gggccttcaa gttgtaggct c                                               21

<210> SEQ ID NO 29
<211> LENGTH: 22
<212> TYPE: DNA
<213> ORGANISM: Artificial Sequence
<220> FEATURE:
<223> OTHER INFORMATION: Description of artificial sequence: Synthetic
      polynucleotides

<400> SEQUENCE: 29
agtctatccg tgagaccatg aa                                              22

<210> SEQ ID NO 30
<211> LENGTH: 19
<212> TYPE: DNA
<213> ORGANISM: Artificial Sequence
<220> FEATURE:
<223> OTHER INFORMATION: Description of artificial sequence: Synthetic
      polynucleotides

<400> SEQUENCE: 30
gcggtacttc caagcagga                                                  19

<210> SEQ ID NO 31
<211> LENGTH: 20
<212> TYPE: DNA
<213> ORGANISM: Artificial Sequence
<220> FEATURE:
<223> OTHER INFORMATION: Description of artificial sequence: Synthetic
``` polynucleotides

<400> SEQUENCE: 31
acggacagat gtgtgagtgg					20

<210> SEQ ID NO 32
<211> LENGTH: 21
<212> TYPE: DNA
<213> ORGANISM: Artificial Sequence
<220> FEATURE:
<223> OTHER INFORMATION: Description of artificial sequence: Synthetic
      polynucleotides

<400> SEQUENCE: 32
caggagctta tagggctcag a					21

<210> SEQ ID NO 33
<211> LENGTH: 21
<212> TYPE: DNA
<213> ORGANISM: Artificial Sequence
<220> FEATURE:
<223> OTHER INFORMATION: Description of artificial sequence: Synthetic
      polynucleotides

<400> SEQUENCE: 33
cttgcacaca aaaagcccac t					21

<210> SEQ ID NO 34
<211> LENGTH: 23
<212> TYPE: DNA
<213> ORGANISM: Artificial Sequence
<220> FEATURE:
<223> OTHER INFORMATION: Description of artificial sequence: Synthetic
      polynucleotides

<400> SEQUENCE: 34
gggatgcctt cttgctatct cat				23

<210> SEQ ID NO 35
<211> LENGTH: 21
<212> TYPE: DNA
<213> ORGANISM: Artificial Sequence
<220> FEATURE:
<223> OTHER INFORMATION: Description of artificial sequence: Synthetic
      polynucleotides

<400> SEQUENCE: 35
tttatgcccc ggaactcctt t					21

<210> SEQ ID NO 36
<211> LENGTH: 21
<212> TYPE: DNA
<213> ORGANISM: Artificial Sequence
<220> FEATURE:
<223> OTHER INFORMATION: Description of artificial sequence: Synthetic
      polynucleotides

<400> SEQUENCE: 36
acaggcaggc agctttatca g					21

<210> SEQ ID NO 37
<211> LENGTH: 22
<212> TYPE: DNA
<213> ORGANISM: Artificial Sequence
<220> FEATURE:
<223> OTHER INFORMATION: Description of artificial sequence: Synthetic
      polynucleotides

<400> SEQUENCE: 37
cctcctacct tgattgcatc ag                                    22

<210> SEQ ID NO 38
<211> LENGTH: 22
<212> TYPE: DNA
<213> ORGANISM: Artificial Sequence
<220> FEATURE:
<223> OTHER INFORMATION: Description of artificial sequence: Synthetic
      polynucleotides

<400> SEQUENCE: 38
ttttgaccca tagaactctg cc                                    22

<210> SEQ ID NO 39
<211> LENGTH: 21
<212> TYPE: DNA
<213> ORGANISM: Artificial Sequence
<220> FEATURE:
<223> OTHER INFORMATION: Description of artificial sequence: Synthetic
      polynucleotides

<400> SEQUENCE: 39
atgctgccca gaagacagat a                                     21

<210> SEQ ID NO 40
<211> LENGTH: 21
<212> TYPE: DNA
<213> ORGANISM: Artificial Sequence
<220> FEATURE:
<223> OTHER INFORMATION: Description of artificial sequence: Synthetic
      polynucleotides

<400> SEQUENCE: 40
ttgttgaagg ttgggtgatc c                                     21

<210> SEQ ID NO 41
<211> LENGTH: 21
<212> TYPE: DNA
<213> ORGANISM: Artificial Sequence
<220> FEATURE:
<223> OTHER INFORMATION: Description of artificial sequence: Synthetic
      polynucleotides

<400> SEQUENCE: 41
ggggagatcg agggctatga g                                     21

<210> SEQ ID NO 42
<211> LENGTH: 21
<212> TYPE: DNA
<213> ORGANISM: Artificial Sequence
<220> FEATURE:
<223> OTHER INFORMATION: Description of artificial sequence: Synthetic
      polynucleotides

<400> SEQUENCE: 42
gatgacggtc cgcttgtttt c                                     21

<210> SEQ ID NO 43
<211> LENGTH: 22
<212> TYPE: DNA
<213> ORGANISM: Artificial Sequence
<220> FEATURE:
<223> OTHER INFORMATION: Description of artificial sequence: Synthetic
      polynucleotides

```
<400> SEQUENCE: 43
tcagggaaag ataaagccga cc                                              22

<210> SEQ ID NO 44
<211> LENGTH: 23
<212> TYPE: DNA
<213> ORGANISM: Artificial Sequence
<220> FEATURE:
<223> OTHER INFORMATION: Description of artificial sequence: Synthetic
      polynucleotides

<400> SEQUENCE: 44
aggtagattc gtgacagaca gac                                             23

<210> SEQ ID NO 45
<211> LENGTH: 21
<212> TYPE: DNA
<213> ORGANISM: Artificial Sequence
<220> FEATURE:
<223> OTHER INFORMATION: Description of artificial sequence: Synthetic
      polynucleotides

<400> SEQUENCE: 45
atggcattgt cccagtctgt t                                               21

<210> SEQ ID NO 46
<211> LENGTH: 21
<212> TYPE: DNA
<213> ORGANISM: Artificial Sequence
<220> FEATURE:
<223> OTHER INFORMATION: Description of artificial sequence: Synthetic
      polynucleotides

<400> SEQUENCE: 46
tggctctggt ggactttca g                                                21

<210> SEQ ID NO 47
<211> LENGTH: 21
<212> TYPE: DNA
<213> ORGANISM: Artificial Sequence
<220> FEATURE:
<223> OTHER INFORMATION: Description of artificial sequence: Synthetic
      polynucleotides

<400> SEQUENCE: 47
aagtcgcctc gaagatacac a                                               21

<210> SEQ ID NO 48
<211> LENGTH: 21
<212> TYPE: DNA
<213> ORGANISM: Artificial Sequence
<220> FEATURE:
<223> OTHER INFORMATION: Description of artificial sequence: Synthetic
      polynucleotides

<400> SEQUENCE: 48
aaggagagaa cactgctcgt g                                               21

<210> SEQ ID NO 49
<211> LENGTH: 20
<212> TYPE: DNA
<213> ORGANISM: Artificial Sequence
<220> FEATURE:
<223> OTHER INFORMATION: Description of artificial sequence: Synthetic
      polynucleotides

<400> SEQUENCE: 49
```
aaggtcgcct caaagagaca                                                20

<210> SEQ ID NO 50
<211> LENGTH: 20
<212> TYPE: DNA
<213> ORGANISM: Artificial Sequence
<220> FEATURE:
<223> OTHER INFORMATION: Description of artificial sequence: Synthetic
      polynucleotides

<400> SEQUENCE: 50
tgcactttct gctggacatc                                                20

<210> SEQ ID NO 51
<211> LENGTH: 19
<212> TYPE: DNA
<213> ORGANISM: Artificial Sequence
<220> FEATURE:
<223> OTHER INFORMATION: Description of artificial sequence: Synthetic
      polynucleotides

<400> SEQUENCE: 51
gcgggaacgc aacaacatc                                                 19

<210> SEQ ID NO 52
<211> LENGTH: 21
<212> TYPE: DNA
<213> ORGANISM: Artificial Sequence
<220> FEATURE:
<223> OTHER INFORMATION: Description of artificial sequence: Synthetic
      polynucleotides

<400> SEQUENCE: 52
gtcactggtc aactccagca c                                              21

<210> SEQ ID NO 53
<211> LENGTH: 19
<212> TYPE: DNA
<213> ORGANISM: Artificial Sequence
<220> FEATURE:
<223> OTHER INFORMATION: Description of artificial sequence: Synthetic
      polynucleotides

<400> SEQUENCE: 53
cttcagcccg tacctggag                                                 19

<210> SEQ ID NO 54
<211> LENGTH: 19
<212> TYPE: DNA
<213> ORGANISM: Artificial Sequence
<220> FEATURE:
<223> OTHER INFORMATION: Description of artificial sequence: Synthetic
      polynucleotides

<400> SEQUENCE: 54
ggagaggaag tcgtggtgc                                                 19

<210> SEQ ID NO 55
<211> LENGTH: 20
<212> TYPE: DNA
<213> ORGANISM: Artificial Sequence
<220> FEATURE:
<223> OTHER INFORMATION: Description of artificial sequence: Synthetic
      polynucleotides

<400> SEQUENCE: 55
taagtggcta ccccaaaacg                                        20

<210> SEQ ID NO 56
<211> LENGTH: 20
<212> TYPE: DNA
<213> ORGANISM: Artificial Sequence
<220> FEATURE:
<223> OTHER INFORMATION: Description of artificial sequence: Synthetic
      polynucleotides

<400> SEQUENCE: 56
gctttgcatt gtccatctga                                        20

<210> SEQ ID NO 57
<211> LENGTH: 22
<212> TYPE: DNA
<213> ORGANISM: Artificial Sequence
<220> FEATURE:
<223> OTHER INFORMATION: Description of artificial sequence: Synthetic
      polynucleotides

<400> SEQUENCE: 57
tcagatggac aatgcaaagc gc                                     22

<210> SEQ ID NO 58
<211> LENGTH: 22
<212> TYPE: DNA
<213> ORGANISM: Artificial Sequence
<220> FEATURE:
<223> OTHER INFORMATION: Description of artificial sequence: Synthetic
      polynucleotides

<400> SEQUENCE: 58
ggcgcatgat gttctccttg ta                                     22

<210> SEQ ID NO 59
<211> LENGTH: 19
<212> TYPE: DNA
<213> ORGANISM: Artificial Sequence
<220> FEATURE:
<223> OTHER INFORMATION: Description of artificial sequence: Synthetic
      polynucleotides

<400> SEQUENCE: 59
ttaggatgtg gacgtaatt                                         19

<210> SEQ ID NO 60
<211> LENGTH: 20
<212> TYPE: DNA
<213> ORGANISM: Artificial Sequence
<220> FEATURE:
<223> OTHER INFORMATION: Description of artificial sequence: Synthetic
      polynucleotides

<400> SEQUENCE: 60
ggtcaagttc aacatgacag                                        20

<210> SEQ ID NO 61
<211> LENGTH: 25
<212> TYPE: DNA
<213> ORGANISM: Artificial Sequence
<220> FEATURE:
<223> OTHER INFORMATION: Description of artificial sequence: Synthetic
      polynucleotides

<400> SEQUENCE: 61
aggacgacga ctacaataag cctct                                  25

<210> SEQ ID NO 62
<211> LENGTH: 22
<212> TYPE: DNA
<213> ORGANISM: Artificial Sequence
<220> FEATURE:
<223> OTHER INFORMATION: Description of artificial sequence: Synthetic
      polynucleotides

<400> SEQUENCE: 62
gcgctgctgg acttgtgctt ct                                              22

<210> SEQ ID NO 63
<211> LENGTH: 19
<212> TYPE: DNA
<213> ORGANISM: Artificial Sequence
<220> FEATURE:
<223> OTHER INFORMATION: Description of artificial sequence: Synthetic
      polynucleotides

<400> SEQUENCE: 63
ggagtcggcg aaagaaggc                                                  19

<210> SEQ ID NO 64
<211> LENGTH: 21
<212> TYPE: DNA
<213> ORGANISM: Artificial Sequence
<220> FEATURE:
<223> OTHER INFORMATION: Description of artificial sequence: Synthetic
      polynucleotides

<400> SEQUENCE: 64
tacaagctgt ggtccgctat g                                               21

<210> SEQ ID NO 65
<211> LENGTH: 21
<212> TYPE: DNA
<213> ORGANISM: Artificial Sequence
<220> FEATURE:
<223> OTHER INFORMATION: Description of artificial sequence: Synthetic
      polynucleotides

<400> SEQUENCE: 65
gcagcctttg tgaaccaaca c                                               21

<210> SEQ ID NO 66
<211> LENGTH: 20
<212> TYPE: DNA
<213> ORGANISM: Artificial Sequence
<220> FEATURE:
<223> OTHER INFORMATION: Description of artificial sequence: Synthetic
      polynucleotides

<400> SEQUENCE: 66
ccccgcacac taggtagaga                                                 20

<210> SEQ ID NO 67
<211> LENGTH: 19
<212> TYPE: DNA
<213> ORGANISM: Artificial Sequence
<220> FEATURE:
<223> OTHER INFORMATION: Description of artificial sequence: Synthetic
      polynucleotides

<400> SEQUENCE: 67
gctgctgtct gaacccaac                                                  19

<210> SEQ ID NO 68
<211> LENGTH: 19
<212> TYPE: DNA
<213> ORGANISM: Artificial Sequence
<220> FEATURE:
<223> OTHER INFORMATION: Description of artificial sequence: Synthetic
      polynucleotides

<400> SEQUENCE: 68
cgttctcggg gtgccatag                                                    19

<210> SEQ ID NO 69
<211> LENGTH: 21
<212> TYPE: DNA
<213> ORGANISM: Artificial Sequence
<220> FEATURE:
<223> OTHER INFORMATION: Description of artificial sequence: Synthetic
      polynucleotides

<400> SEQUENCE: 69
ttcagacctt ggtgggaaag a                                                 21

<210> SEQ ID NO 70
<211> LENGTH: 22
<212> TYPE: DNA
<213> ORGANISM: Artificial Sequence
<220> FEATURE:
<223> OTHER INFORMATION: Description of artificial sequence: Synthetic
      polynucleotides

<400> SEQUENCE: 70
acgaacccca acattgttac at                                                22

<210> SEQ ID NO 71
<211> LENGTH: 19
<212> TYPE: DNA
<213> ORGANISM: Artificial Sequence
<220> FEATURE:
<223> OTHER INFORMATION: Description of artificial sequence: Synthetic
      polynucleotides

<400> SEQUENCE: 71
gacaagcgcc attcacagg                                                    19

<210> SEQ ID NO 72
<211> LENGTH: 23
<212> TYPE: DNA
<213> ORGANISM: Artificial Sequence
<220> FEATURE:
<223> OTHER INFORMATION: Description of artificial sequence: Synthetic
      polynucleotides

<400> SEQUENCE: 72
tgacgtttgg caatgttatt cct                                               23

<210> SEQ ID NO 73
<211> LENGTH: 20
<212> TYPE: DNA
<213> ORGANISM: Artificial Sequence
<220> FEATURE:
<223> OTHER INFORMATION: Description of artificial sequence: Synthetic
      polynucleotides

<400> SEQUENCE: 73
ggcagccaag tgaaaaccag                                                   20

<210> SEQ ID NO 74
<211> LENGTH: 22
<212> TYPE: DNA
<213> ORGANISM: Artificial Sequence
<220> FEATURE:
<223> OTHER INFORMATION: Description of artificial sequence: Synthetic
      polynucleotides

<400> SEQUENCE: 74
ggtgatgtag cgactgtagt aa                                              22

<210> SEQ ID NO 75
<211> LENGTH: 24
<212> TYPE: DNA
<213> ORGANISM: Artificial Sequence
<220> FEATURE:
<223> OTHER INFORMATION: Description of artificial sequence: Synthetic
      polynucleotides

<400> SEQUENCE: 75
tgcagtgtga tgtctctgtt gggt                                            24

<210> SEQ ID NO 76
<211> LENGTH: 24
<212> TYPE: DNA
<213> ORGANISM: Artificial Sequence
<220> FEATURE:
<223> OTHER INFORMATION: Description of artificial sequence: Synthetic
      polynucleotides

<400> SEQUENCE: 76
atccatgggc cagcaacaat tgac                                            24

<210> SEQ ID NO 77
<211> LENGTH: 24
<212> TYPE: DNA
<213> ORGANISM: Artificial Sequence
<220> FEATURE:
<223> OTHER INFORMATION: Description of artificial sequence: Synthetic
      polynucleotides

<400> SEQUENCE: 77
agctcctcta caggcttgtt cact                                            24

<210> SEQ ID NO 78
<211> LENGTH: 26
<212> TYPE: DNA
<213> ORGANISM: Artificial Sequence
<220> FEATURE:
<223> OTHER INFORMATION: Description of artificial sequence: Synthetic
      polynucleotides

<400> SEQUENCE: 78
ggacgtgttc aatgctaaca gcaacc                                          26

<210> SEQ ID NO 79
<211> LENGTH: 20
<212> TYPE: DNA
<213> ORGANISM: Artificial Sequence
<220> FEATURE:
<223> OTHER INFORMATION: Description of artificial sequence: Synthetic
      polynucleotides

<400> SEQUENCE: 79
tgacctcaac gatgcatttc                                                 20

<210> SEQ ID NO 80

```
<211> LENGTH: 20
<212> TYPE: DNA
<213> ORGANISM: Artificial Sequence
<220> FEATURE:
<223> OTHER INFORMATION: Description of artificial sequence: Synthetic
      polynucleotides

<400> SEQUENCE: 80
ctgtcctggc tcttctgctc                                               20

<210> SEQ ID NO 81
<211> LENGTH: 22
<212> TYPE: DNA
<213> ORGANISM: Artificial Sequence
<220> FEATURE:
<223> OTHER INFORMATION: Description of artificial sequence: Synthetic
      polynucleotides

<400> SEQUENCE: 81
cttgtcctcc tttctgttac gg                                            22

<210> SEQ ID NO 82
<211> LENGTH: 20
<212> TYPE: DNA
<213> ORGANISM: Artificial Sequence
<220> FEATURE:
<223> OTHER INFORMATION: Description of artificial sequence: Synthetic
      polynucleotides

<400> SEQUENCE: 82
cccctgtagc catccattcc                                               20

<210> SEQ ID NO 83
<211> LENGTH: 24
<212> TYPE: DNA
<213> ORGANISM: Artificial Sequence
<220> FEATURE:
<223> OTHER INFORMATION: Description of artificial sequence: Synthetic
      polynucleotides

<400> SEQUENCE: 83
gccatccttt acttctacct gctc                                          24

<210> SEQ ID NO 84
<211> LENGTH: 24
<212> TYPE: DNA
<213> ORGANISM: Artificial Sequence
<220> FEATURE:
<223> OTHER INFORMATION: Description of artificial sequence: Synthetic
      polynucleotides

<400> SEQUENCE: 84
gctcatacgt gcctttgatg atgg                                          24

<210> SEQ ID NO 85
<211> LENGTH: 26
<212> TYPE: DNA
<213> ORGANISM: Artificial Sequence
<220> FEATURE:
<223> OTHER INFORMATION: Description of artificial sequence: Synthetic
      polynucleotides

<400> SEQUENCE: 85
tcatggacac accctccagt tatgag                                        26

<210> SEQ ID NO 86
<211> LENGTH: 26
```

```
<212> TYPE: DNA
<213> ORGANISM: Artificial Sequence
<220> FEATURE:
<223> OTHER INFORMATION: Description of artificial sequence: Synthetic
      polynucleotides

<400> SEQUENCE: 86
tgagcttaat gatgctttct ctgggc                                              26

<210> SEQ ID NO 87
<211> LENGTH: 21
<212> TYPE: DNA
<213> ORGANISM: Artificial Sequence
<220> FEATURE:
<223> OTHER INFORMATION: Description of artificial sequence: Synthetic
      polynucleotides

<400> SEQUENCE: 87
cggcatgaac atgagcggca t                                                   21

<210> SEQ ID NO 88
<211> LENGTH: 24
<212> TYPE: DNA
<213> ORGANISM: Artificial Sequence
<220> FEATURE:
<223> OTHER INFORMATION: Description of artificial sequence: Synthetic
      polynucleotides

<400> SEQUENCE: 88
gccgacaggt acttctgttg cttg                                                24

<210> SEQ ID NO 89
<211> LENGTH: 24
<212> TYPE: DNA
<213> ORGANISM: Artificial Sequence
<220> FEATURE:
<223> OTHER INFORMATION: Description of artificial sequence: Synthetic
      polynucleotides

<400> SEQUENCE: 89
gtgcgaagtg aaggacgttt gtgt                                                24

<210> SEQ ID NO 90
<211> LENGTH: 23
<212> TYPE: DNA
<213> ORGANISM: Artificial Sequence
<220> FEATURE:
<223> OTHER INFORMATION: Description of artificial sequence: Synthetic
      polynucleotides

<400> SEQUENCE: 90
tttgagacca tctctcccgt ccc                                                 23

<210> SEQ ID NO 91
<211> LENGTH: 22
<212> TYPE: DNA
<213> ORGANISM: Artificial Sequence
<220> FEATURE:
<223> OTHER INFORMATION: Description of artificial sequence: Synthetic
      polynucleotides

<400> SEQUENCE: 91
tctgagtgcc acctctgcat gt                                                  22

<210> SEQ ID NO 92
<211> LENGTH: 22
<212> TYPE: DNA
```

```
<213> ORGANISM: Artificial Sequence
<220> FEATURE:
<223> OTHER INFORMATION: Description of artificial sequence: Synthetic
      polynucleotides

<400> SEQUENCE: 92
tggagcattg cctgtggtat gg                                              22

<210> SEQ ID NO 93
<211> LENGTH: 24
<212> TYPE: DNA
<213> ORGANISM: Artificial Sequence
<220> FEATURE:
<223> OTHER INFORMATION: Description of artificial sequence: Synthetic
      polynucleotides

<400> SEQUENCE: 93
ccttcttatc gtggtggtgg tggt                                            24

<210> SEQ ID NO 94
<211> LENGTH: 24
<212> TYPE: DNA
<213> ORGANISM: Artificial Sequence
<220> FEATURE:
<223> OTHER INFORMATION: Description of artificial sequence: Synthetic
      polynucleotides

<400> SEQUENCE: 94
tctccgtgtg tttctggctc atgt                                            24

<210> SEQ ID NO 95
<211> LENGTH: 24
<212> TYPE: DNA
<213> ORGANISM: Artificial Sequence
<220> FEATURE:
<223> OTHER INFORMATION: Description of artificial sequence: Synthetic
      polynucleotides

<400> SEQUENCE: 95
actacaaacg ccagaaccct acca                                            24

<210> SEQ ID NO 96
<211> LENGTH: 23
<212> TYPE: DNA
<213> ORGANISM: Artificial Sequence
<220> FEATURE:
<223> OTHER INFORMATION: Description of artificial sequence: Synthetic
      polynucleotides

<400> SEQUENCE: 96
tgtcattgtc acagacgccc tca                                             23

<210> SEQ ID NO 97
<211> LENGTH: 20
<212> TYPE: DNA
<213> ORGANISM: Artificial Sequence
<220> FEATURE:
<223> OTHER INFORMATION: Description of artificial sequence: Synthetic
      polynucleotides

<400> SEQUENCE: 97
acggttcctc gcagttcaat                                                 20

<210> SEQ ID NO 98
<211> LENGTH: 20
<212> TYPE: DNA
<213> ORGANISM: Artificial Sequence
```

-continued

```
<220> FEATURE:
<223> OTHER INFORMATION: Description of artificial sequence: Synthetic
      polynucleotides

<400> SEQUENCE: 98
gcagcttgga acataggggt                                                   20

<210> SEQ ID NO 99
<211> LENGTH: 21
<212> TYPE: DNA
<213> ORGANISM: Artificial Sequence
<220> FEATURE:
<223> OTHER INFORMATION: Description of artificial sequence: Synthetic
      polynucleotides

<400> SEQUENCE: 99
agccactgct gtgcttttaa g                                                 21

<210> SEQ ID NO 100
<211> LENGTH: 21
<212> TYPE: DNA
<213> ORGANISM: Artificial Sequence
<220> FEATURE:
<223> OTHER INFORMATION: Description of artificial sequence: Synthetic
      polynucleotides

<400> SEQUENCE: 100
ccaaaaccaa tgatctcatc c                                                 21
```

SMALL MOLECULE COMPOUND COMBINATION FOR REPROGRAMMING DIGESTIVE TRACT DERIVED EPITHELIAL CELLS TO ENDODERMAL STEM/PROGENITOR CELLS, REPROGRAMMING METHOD AND APPLICATION

INCORPORATION BY REFERENCE OF SEQUENCE LISTING

The Sequence Listing in the ASCII text file, named as 36900_SequenceListing.txt of 24 KG, created on Jul. 8, 2021, and submitted to the United States Patent and Trademark Office via EFS-Web, is incorporated herein by reference.

FIELD OF THE INVENTION

The present invention belongs to the field of cell engineering technology and relates to a technology for reprogramming digestive tract-derived epithelial cells into endoderm stem/progenitor cells, including specific small molecule compound combinations, reprogramming kits, reprogramming methods used in reprogramming, and the application of the endodermal stem/progenitor cells to further induce differentiation into parenchymal cells.

BACKGROUND OF THE INVENTION

Stem cell technology has been rated as the most promising technology in the life sciences in the 21st century by "Nature" and "Science" magazines. It is a brand-new medical technology that overcomes those serious diseases which are beyond the reach of traditional medical treatments. Because of the potential of self-renewal and multipotential differentiation of stem cells, which are wildly used in the fields of organ regeneration, disease modeling, developmental biology and drug discovery. Stem cell theory and technology research has achieved rapid development over the past decade, and it is expected to become a new disease treatment method, promote the paradigm shift of medical treatment, and lead a new medical revolution. There are many different classification methods for stem cells. From a developmental perspective, stem cells are roughly classified into two categories: Embryonic stem cells (ESCs) and Adult stem cells (ASCs). ESCs are derived from the inner cell mass (ICM) of the blastocyst stage and are pluripotent stem cells with infinite self-renewal and differentiation into all cell types of the human body. In 1998, Thomson established human embryonic stem cell lines (hESCs) for the first time in the world [Thomson J A, Itskovitz-Eldor J, Shapiro S S, Waknitz M A, Swiergiel J J, Marshall V S, et al. Embryonic Stem Cell Lines Derived from Human Blastocysts. *Science*. 1998; 282:1145-7.]. Because it can produce all cell types in adults, it can theoretically provide an ideal source of cells for basic research, disease treatment and drug discovery. The use of ESCs over the years has produced a variety of functional cells, including cardiomyocytes, nerve cells, blood cells, and liver cells [Murry C E, Keller G Differentiation of Embryonic Stem Cells to  Clinically Relevant Populations: Lessons from Embryonic Development. *Cell*. 132: 661-80.]. However, many problems such as the international ethical concerns faced by the use of ESCs, and immune rejection after transplantation produced by ESCs-derived cells, and teratoma formed by undifferentiated ESCs greatly limit the clinical application of ESCs. Adult stem cells, such as hematopoietic stem cells, mesenchymal stem cells, liver stem cells and neural stem cells, exist in various tissues at various stages after birth. ASCs have a certain self-renewal ability and can differentiate into mature cells related to their source tissues. Since they are derived from adult tissues and can only differentiate into specific lineages, they do not have the risk of teratoma and have no ethical problems, they are good seed cells for clinical disease treatment. However, the scarcity of cell sources of ASCs, which can only be isolated from human tissues, and the restricted differentiation potential of ASCs, which can only generate one or several mature cell types in their lineage, and the limited proliferation capacity in vitro of ASCs severely impede the clinical application of ASCs. Over the years, numerous studies have focused on finding more desirable cell types for disease treatment, drug discovery, and mechanism research.

The traditional epigenetic view holds that lineage specialization and differentiation of cells are unidirectional and irreversible processes, and the cell fate of pluripotent cells can only be specified to terminal mature cells (Waddington' epigenetic landscape). The emergence of induced Pluripotent Stem Cells (iPSCs) profoundly changed this concept. In 2006, Yamanaka et al. successfully converted fibroblasts into ESCs-like pluripotent stem cell iPSCs using four pluripotency-related transcription factors OCT4, SOX2, KLF4, and c-MYC (OSKM), which for the first time demonstrated that terminally differentiated cells could regain differentiation pluripotency under the action of pluripotency-related transcription factors. This is the classic reprogramming technique [Takahashi K, Yamanaka S. Induction of Pluripotent Stem Cells from Mouse Embryonic and Adult Fibroblast Cultures by Defined Factors. *Cell*. 126:663-76. Takahashi K, Tanabe K, Ohnuki M, Narita M, Ichisaka T, Tomoda K, et al. Induction of Pluripotent Stem Cells from Adult Human Fibroblasts by Defined Factors. *Cell*. 131:861-72.]. The emergence of iPSCs has a milestone significance: Firstly, it breaks through the classical epigenetic panoramic mode, greatly enriching the theory of cell fate conversion, leading the paradigm shift of cell fate coversion research and stem cell research, opening a new era for basic research and clinical applications in regenerative medicine. Secondly, iPSCs have the potential to infinitely self-renew and differentiate into all cell types in the body which ESCs also have, while avoiding ethical controversy in the study and application of ESCs. Thirdly, since fibroblasts can be obtained from the patient's own body, the immune rejection problem caused by the transplantation of terminal cells produced by ESCs differentiation into the body can also be avoided. Finally, patient-derived iPSCs can establish personalized disease cell models and individualized drug screening platforms. The emergence of iPSCs not only brings new research models for basic research, drug screening, but also promote the clinical application of pluripotent stem cells (PSCs). The iPSCs has been successfully used to produce a variety of functional cell types, and clinical trials of iPSCs-derived retinal pigment epithelium for the treatment of blinding eye diseases are underway. Yamanaka also won the 2012 Nobel Prize in Physiology or Medicine for this technology.

Although iPSCs have many advantages and are a very promising cell type, it is still difficult to avoid the risk of teratoma due to the similar pluripotency of ESCs. In addition, there are a variety of undesired cell types produced due to the problem of random differentiation during the differentiation of iPSCs into functional cells. These problems cause safety concerns in large-scale clinical applications of iPSCs. In order to make up for this shortcoming, in recent years, lineage reprogramming technology which is based on the technology and principle of iPSCs has received increasing attention. Lineage reprogramming mainly involves the overexpression of lineage specific transcriptional factors rather than pluripotent transcription factors (OSKM) in initiating cells, mainly dermal fibroblasts or blood cells, for converting the initiating cells into cells of interest directly. The emergence of lineage reprogramming is also a milestone in the stem cell field. Firstly, lineage reprogramming avoids the teratoma risk of iPSCs by bypassing the pluripotency stage. Secondly, lineage reprogramming can directly obtain mature functional cells or adult stem cells with expansion ability depending on the transcription factors and culture conditions, and the obtained target cell types are relatively homogenous. Thirdly, lineage reprogramming also has the advantages of iPSCs without immunological rejection and can also achieve individualized treatment, thus showing a broad application prospect in stem cell and regenerative medicine research and disease treatment [Sancho-Martinez I, Baek S H, Izpisua Belmonte J C Lineage conversion methodologies meet the reprogramming toolbox. *Nat Cell Biol.* 2012; 14:892-9.]. Finally, lineage reprogramming has greatly enriched the theory of cell fate conversion and cell reprogramming, helping people to understand the specialization and regulation of cell fate and to apply this concept to a broader perspective.

Many breakthroughs have been achieved in the field of lineage reprogramming. The lineage reprogramming of pancreatic exocrine cells to endocrine beta cells was first realized in 2008, in which the two cells were from the same germ layer [ZHOU Q, Brown J, Kanarek A, Rajagopal J, Melton D A. In vivo reprogramming of adult pancreatic exocrine cells to beta-cells. *Nature.* 2008; 455: 627-32.]. And the conversion of fibroblasts to neuroblasts across the germ layer was achieved in 2010 [Vierbuchen T, Ostermeier A, Pang Z P, Kokubu Y, Sudhof T C, Wernig M. Direct conversion of fibroblasts. *Nature.* 2010; 463:1035-41.]. Currently, cell fate coversion in a variety of cell types of all the three germ layers can be realized by using the viral-mediated transcription factors overexpression in somatic cells. In the ectoderm, fibroblasts have been converted into neurons, neural stem cells, etc.; in the mesoderm, cardiomyocytes, myocardial progenitor cells, and hematopoietic stem/progenitor cells have been induced; in the endoderm, pancreatic cells, hepatocytes and liver stem cells also have been obtained. Chinese scientists have made great breakthrough in lineage reprogramming of liver cells. In 2011, Lijian Hui and colleagues successfully converted mouse fibroblasts into hepatocytes using a combination of hepatocyte-specific transcription factors [HUANG P, He Z, Ji S, Sun H, Xiang D, Liu C, et al. Induction of functional hepatocyte-like cells from mouse fibroblasts by defined factors. *Nature.* 2011; 475:386-9.]. In 2013, Yiping Hu et al. used transcription factor combinations to obtain the mouse liver stem cells which had proliferation ability and can differentiate into both hepatocytes and biliary cells [Yu B, He Z Y, You P, Han Q W, Xiang D, Chen F, et al Reprogramming fibroblasts into bipotential hepatic stem cells by defined factors. *Cell Stem Cell.* 2013; 13:328-40.]. In 2015, Hui lab and Deng lab independently reported successful conversion of human fibroblasts into functional hepatocytes using different transcription factor combinations, providing a good cell source for liver disease treatment and drug screening [Du Y, Wang J, Jia J, Song N, Xiang C, Xu J, et al. Human hepatocytes with drug metabolic function induced from fibroblasts by lineage reprogramming. *Cell Stem Cell.* 2014; 14:394-403. Huang P, Zhang L, Gao Y, He Z, Yao D, Wu Z, et al. Direct reprogramming of human fibroblasts to functional and expandable hepatocytes. *Cell Stem Cell.* 2014; 14:370-84.]. Although many human or mice cells types have been induced by lineage reprogramming over the years and lineage reprogramming has made up for multiple defects of iPSCs, most of the current lineage reprogramming studies rely on lentivirus or retrovirus-mediated transcription factor overexpression. These viral vectors are integrated in the host genome after they enter the target cells, which may lead to genome of the host instability, thus causing safety concerns for future clinical application. In addition, transcription factor is hard to scale up due to the complicated procedures varying among different labs and the low efficiency. Therefore, many studies are currently looking for a safer and more efficient way to replace transcription factor.

Compared with transcription factors, small molecule compounds have many advantages. Small molecule compounds are cell permeable, easy to synthesize, cost-effective, non-immunogenic. They act on protein levels without genome integration, and can be standardized and scaled for production. Spatiotemporal and intensity regulation of proteins is relatively easy to achieve by changing the concentration and duration of small molecules treatment. In recent years, many researchers have been devoted to screening small molecules for improving the generation efficiency of iPSCs, shortening the generation time of iPSCs, and reducing the use of transcription factors. The ultimate goal is to completely replace the classical Yamanaka four factors with small molecules, avoiding the integration of the virus in host cells [Li W, Li K, Wei W, Ding S. Chemical approaches to stem cell biology and therapeutics. *Cell Stem Cell.* 2013; 13:270-83.]. In 2013, Deng Lab made a breakthrough progress in this area. Through multiple screenings, the team found a suitable combination of small molecule compounds to achieve the reprogramming of mouse fibroblasts to iPSCs without relying on any exogenous transcription factors. Despite the reprogramming efficiency of 0.2% and the complicated process, this finding provided theoretical and practical basis for small molecule-based reprogramming and lineage reprogramming [Hou P, Li Y, Zhang X, Liu C, Guan J, Li H, et al. Pluripotent Stem Cells Induced from Mouse Somatic Cells by Small-Molecule Compounds. *Science.* 2013; 341:651-4.]. While studying the production of iPSCs by small molecule compounds, in order to generate safe, efficient and controllable target cells, researchers have made great efforts to screen small molecules to promote lineage reprogramming or replace lineage-specific transcription factors [Li K, Zhu S, Russ H A, Xu S, Xu T, Zhang Y, et al. Small molecules facilitate the reprogramming of mouse fibroblasts into pancreatic lineages. *Cell Stem Cell.* 2014; 14:228-36. Zhu S, Rezvani M, Harbell J, Mattis A N, Wolfe A R, Benet L Z, et al. Mouse liver repopulation with hepatocytes generated from human fibroblasts. *Nature.* 2014; 508:93-7. Zhu S, Russ H A, Wang X, Zhang M, Ma T, Xu T, et al. Human pancreatic beta-like cells converted from fibroblasts. *Nat Commun.* 2016; 7:10080.]. Chinese scientists have also achieved remarkable achievements in this field. Recently, Pei lab reported a combination of small molecules which was used to reprogram fibroblasts derived from Alzheimer's disease patients into mature functional neurons [Hu W, Qiu B, Guan W, Wang Q, Wang M, Li W, et al. Direct Conversion of Normal and Alzheimer's Disease Human Fibroblasts into Neuronal Cells by Small Molecules. *Cell Stem Cell.* 2015; 17:204-12.]. Deng lab successfully converted mouse fibroblasts into neurons using a combination of small molecules [Li X, Zuo X, Jing J, Ma Y, Wang J, Liu D, et al. Small-Molecule-Driven Direct Reprogramming of Mouse Fibroblasts into Functional Neurons. *Cell Stem Cell*. 2015; 17:195-203.]. Lei Zhang et al. reported the lineage reprogramming of human astrocyte to functional neurons with small molecules [Zhang L, Yin J C, Yeh H, Ma N X, Lee G, Chen X A, et al. Small Molecules Efficiently Reprogram Human Astroglial Cells Into Functional Neurons. *Cell Stem Cell*. 2015; 17:735-47.]. These breakthroughs have established a solid theoretical basis and laid great promise for the complete use of small molecules to convert adult cells into other types of functional cells or stem cells. "Basic Research on the Application of Somatic *Cell Reprogramming* Technology in Liver Regeneration" [Wencheng Zhang, 2012 Ph.D Thesis] reported the lineage reprogramming of gastrointestinal cells to induced endoderm multipotent stem cells (iEMSC) by small molecule compounds. Small molecule compounds of SB431542, VPA, Y27632 and unpublished 1#-6# combination of small molecules were used to compare the reprogramming efficiency.

Endoderm stem/progenitor cells give rise to cells of internal organs such as liver, pancreas, stomach, and intestine. Endodermal stem/progenitor cells are obtained and extensively expanded, and then induced to differentiate, obtaining a large number of functional hepatocytes, pancreatic cells or intestinal epithelial cells, which will have great implications for the treatment of various types of endoderm organ disorders. As we all know, China is seriously threatened by liver diseases. There are currently 97 million hepatitis B virus carriers and 10 million hepatitis C virus carriers in China. In recent years, the incidence of alcoholic fatty liver disease and nonalcoholic fatty liver disease in China has also increased significantly. Other liver diseases, including drug-induced liver damage and immune liver disease, have seriously threatened national health [Wang F S, Fan J G, Zhang Z, Gao B, Wang H Y. The global burden of liver disease: the major impact of China. *Hepatology*. 2014; 60:2099-108.]. Many liver diseases will develop into end-stage liver disease (ESLD) represented by liver cirrhosis, liver failure and liver cancer if lack of timely and effective treatment. Hundreds of thousands of Chinese people suffer from ESLD every year. At current, the treatments for ESLDs are still very limited. Artificial liver is not mature enough to be carried out on a large scale, while the Medical Treatment can only adopt a conservative and palliative approach. The most effective treatment for ESLD is the orthotopic liver transplantation. However, it is severely limited by the shortage of the donor liver. It is estimated that more than 380,000 people die in ESLD each year in China, causing tremendous suffering to thousands of families and bringing a heavy medical burden to society. Functional hepatocyte transplantation is considered a good alternative to liver transplantation, yet it is also limited by the source. In addition, as other countries in the world, China also has a large number of populations with diabetes, with a stablily increasing trendency year by year. The International Diabetes Federation indicates that diabetes will affect more than 3 billion people worldwide in the coming future. The current treatments of diabetes are also limited and the outcomes are various. Especially for patients with type I diabetes (T1DM) injection of exogenous insulin for a lifetime is currently the only treatment. Long-term injection of insulin is expensive and prone to insulin tolerance, and there are a series of common chronic complications such as infection, hypoglycemia and allergic reactions. Remarkable progress has been made using exogenous transplantation of islet beta cells to cure T1DM. [Bellin M D, Barton F B, Heitman A, Alejandro R, Hering B J. Potent induction immunotherapy promotes long-term insulin independence after islet transplantation in type 1 diabetes. American Journal of Transplantation. 2012; 12:1576-83.]. However, the lack of exogenous islets or beta cells severely hampers the application of this treatment. If endodermal stem/progenitor cells can be obtained and extensively expanded and then induced to differentiate to obtain a large number of functional hepatocytes, pancreatic beta cells or intestinal epithelial cells, which will bring great hope for cell treatment of liver disease, cell treatment of diabetes and even the treatment of intestinal diseases.

Many studies have reported obtaining the endodermal stem/progenitor cells from pluripotent stem cell (ESCs or iPSCs) and the differentiation of those cells into hepatocyte and pancreatic cells. [Sneddon J B, Borowiak M, Melton D A. Self-renewal of embryonic-stem-cell-derived progenitors by organ-matched mesenchyme. Nature. 2012; 491:765-8. Cheng X, Ying L, Lu L, Galvao A M, Mills J A, Lin H C, et al. Self-renewing endodermal progenitor lines generated from human pluripotent. Cell stem cell. 2012; 10: 371-84.]. However, as those cells are all derived from pluripotent stem cells, it is hard to avoid the aforementioned issues related to the applications pluripotent stem cells. Currently, many international studies are devoted to the use of small molecules to reprogram human adult cells into endodermal progenitor cells or liver cells and pancreatic cells from which they are derived. In 2014, Sheng Ding, et al use Yamanaka four-factor OSKM to transiently overexpress in human fibroblasts and combine small molecules to first enter a pluripotent intermediate state which was different from ESCs or iPSCs pluripotent state, and then given the induction condition of endoderm, the fibroblasts were reprogrammed into the endoderm progenitor cells (EPs) state, followed by sequential induction of hepatocytes to obtain hepatocyte-like cells [Zhu S, Rezvani M, Harbell J, Mattis A N, Wolfe A R, Benet L Z, et al. Mouse liver repopulation with hepatocytes generated from human fibroblasts. Nature. 2014; 508:93-7.]. Recently, using the similar strategy, Ding's team could reprogram human fibroblasts into the endoderm progenitor cells state, and then induced differentiation into the pancreas to obtain functional beta cells [Zhu S, Russ H A, Wang X, Zhang M, Ma T, Xu T, et al. Human pancreatic beta-like cells converted from fibroblasts. Nat Commun. 2016; 7:10080.]. This strategy does not pass the pluripotent state, so it avoids the teratogenicity of pluripotent stem cells, but it still needs the initial driving of the OSKM four factors, so it is still a strategy that depends partly on transcription factors. It is not completely dependent on the role of small molecules. Analyzing the cause that the current reprogramming field has not yet achieved the use of small molecules to mediate lineage reprogramming to obtain epithelial-derived endoderm lineage cell types including endodermal progenitor cells, hepatocytes or pancreatic cells, we consider those listed below are the most critical scientific questions:

1. Problems with initiating cells: First, whether it is classical reprogramming of iPSCs or lineage reprogramming, most of them start with fibroblasts. Fibroblasts are relatively easy to obtain than other adult cells, and can be obtained by skin biopsy. Therefore, they are also a major advantage in clinical application. However, for the desired target cells such as endoderm progenitor cells, hepatocytes or pancreatic cells, there are epigenetic barriers initiating with fibroblasts. Fibroblasts are the mesoderm-derived cells, while the target endodermal progenitor cells belong to the endoderm. The transition from mesoderm to endoderm is a great obstacle, especially for small molecules that act more mildly. Second, fibroblasts belong to mesenchymal cells in histological classification, while endodermal progenitor cells belong to epithelial cells. The transition from fibroblasts to endoderm progenitors requires a process of interstitial epithelial transition (MET). MET has been proven to be the priority obstacle for generating iPSCs [Li R, Liang J, Ni S, Zhou T, Qing X, Li H, et al. A mesenchymal-to-epithelial transition initiates and is required For the nuclear reprogramming of mouse fibroblasts. Cell Stem Cell. 2010; 7:51-63.], which is also an important obstacle for lineage reprogramming.

2. Issues with the selection of small molecules. The selection of small molecules is closely related to the characteristics of the initiating cells, and the different initiating cells determine the combination of small molecules required for the transition to endodermal progenitor cells. Since there is no report on the complete use of small molecules to obtain any cell type of endoderm as a reference, detailed investigation and screening are required for the selection of small molecules.

3. Issues with the use of trophoblast cells: trophoblast cells can secrete a variety of cytokines, soluble extracellular matrices or microRNAs, and are in close contact with the cultured cells to provide a suitable extracellular microenvironment for cell growth and survival. trophoblast cells are often necessary for culture and reprogramming of stem/progenitor cells, and the most commonly used trophoblast cells, whether reprogramming or lineage reprogramming, are mouse embryonic fibroblasts (MEFs), human foreskin Fibroblasts (HFFs) or mesenchymal stem cells (MSCs), etc., which provide only a basic stem cell growth environment and do not have lineage-specific support and induction.

SUMMARY OF THE INVENTION

The object of the present invention is to provide a small molecule compound combination for reprogramming digestive tract derived epithelial cells to endodermal stem/progenitor cells, and a reprogramming kit and a reprogramming method for reprogramming digestive tract derived epithelial cells to endodermal stem/progenitor cells.

Because the definition of stem cells and progenitor cells is still a disputed issue and the name of stem cells and progenitor cells is also non-unity, thus the stem/progenitor cells refer to the stem cells or progenitor cells in this invention.

The small molecule compound combination provided by the present invention can reprogram digestive tract derived epithelial cells to endodermal stem/progenitor cells. Wherein the small molecule compound is selected from the group consisting of TGF-β signaling pathways, epigenetic modulators, $Ca^{2+}$ channel activators, and metabolic pathway regulators, and the like functional groups, typically, a combination including 8 small molecule compounds (8M), including a combination of all or a plurality of FBP, Bay K 8644 (Bay), Bix01294 (Bix), SB431542 (SB) or A83-01 (A83), VPA, RG108 (RG), PD0325901, and PS48, including SB or A83.

Wherein, the combination including 8 small molecule compounds (abbreviated as 8M) is: a combination of SB431542: VPA: PD0325901: RG108: Bix01294: Bay K 8644: PS48: FBP in a molar ratio of 50:12500:12.5:1:12.5: 50:125:87500; or a combination of A83:VPA:PD0325901: RG108:Bix01294:Bay K 8644:PS48:FBP in a molar ratio of 12.5:12500:12.5:1:12.5:50:125:87500. When use the 8M combination according to the above ratio, the RG working concentration needs to be 0.01 to 1 μM, preferably 0.04 μM.

Preferably, the small molecule compound combination for reprogramming digestive tract derived epithelial cells to endodermal stem/progenitor cells is a combination including 4 small molecule compounds, such as Bix01294 (Bix), Bay K 8644 (Bay), RG108 (RG), and SB431542 (SB), referred to as BBRS combination, or A83-01 (A83), Bay K 8644 (Bay), RG108 (RG), and SB431542 (SB), referred to as BBRA combination.

Each compound in the small molecule compound combination is used at a concentration of SB43152 of 1 to 10 μM, A83 of 0.4 to 1 μM, RG108 of 0.01 to 1 μM, Bix01294 of 0.1 to 2 μM, Bay K 8644 of 1 to 4 μM, respectively.

Wherein the BBRS combination is a combination of each compound of SB:RG:Bix:Bay in a molar ratio of 50:1:12.5: 50, and the BBRA combination is a combination of each compound of A83:RG:Bix:Bay in a molar ratio of 12.5:1: 12.5:50. Preferably, each compound is used at a concentration of SB431542 of 2 μM, A83 of 0.5 μM, RG108 of 0.04 M, Bix01294 of 0.5 μM, and Bay K 8644 of 2 μM.

In the present invention, the small molecule compound combination can reprogram the digestive tract derived epithelial cells to endodermal stem/progenitor cells with the support of gastric subepithelial myofibroblasts (GSEMFs) or intestinal subepithelial myofibroblasts (ISEMFs) as trophoblast cells.

The reprogramming kit for reprogramming digestive tract derived epithelial cells to endodermal stem/progenitor cells provided by the present invention includes the above small molecule compound combination for reprogramming digestive tract derived epithelial cells to endodermal stem/progenitor cells, and instructions for use of the compounds. Each compound is packaged separately, or each compound is mixed and packaged in an 8M combination or a BBRS combination or a BBRA combination, and the concentration range or specific concentration of each compound used is described in the instructions.

The reprogramming kit further includes trophoblast cells and instructions for use thereof, the trophoblast cells being digestive tract derived stromal cells, such as gastric subepithelial myofibroblasts or intestinal subepithelial myofibroblasts.

The reprogramming kit further includes basal medium, Advanced DMEM/F12, basal additive components for cell culture, Glutamine (Glutamax) and Antibiotic (SP), and instructions for use thereof, wherein Glutamine is used at a concentration of 2 mM (1×) relative to Advanced DMEM/F12 basal medium, the Antibiotic is penicillin and streptomycin, penicillin is used at a concentration of 100 U/mL and streptomycin is used at a concentration of 0.1 mg/mL relative to Advanced DMEM/F12 basal medium, and each substance is packaged separately or mixed with basal medium according to the listed concentration.

The present invention also provides a reprogramming medium for reprogramming digestive tract derived epithelial cells to endodermal stem/progenitor cells. The reprogramming medium is prepared by blending the small molecule compound combination with basal medium and basal additive components for cell culture.

An optimized reprogramming medium is formulated as: Advanced DMEM/F12 containing 2 mM of Glutamine (Glutamax), penicillin and streptomycin (100 U/mL of penicillin and 0.1 mg/mL of streptomycin), 2 μM of SB431542, 0.5 mM of VPA, 0.5 μM of PD0325901, 0.04 μM of RG108, 0.5 μM of Bix01294, 2 μM of Bay K8644, 5 μM of PS48, 3.5 mM of FBP. The concentrations listed are the concentrations used, i.e. the concentrations of the components in Advanced DMEM/F12 (solvent).

A more preferred reprogramming medium is formulated as: Advanced DMEM/F12 containing 2 mM of Glutamine (Glutamax), penicillin and streptomycin (100 U/mL of penicillin and 0.1 mg/mL of streptomycin), 1 to 10 μM of SB431542, 0.01 to 1 μM of RG108, 0.1 to 2 μM of Bix01294, 1 to 4 μM of Bay K 8644; most preferred reprogramming medium herein is formulated as: Advanced DMEM/F12 containing 2 mM of Glutamine (Glutamax), penicillin and streptomycin (100 U/mL of penicillin and 0.1 mg/mL of streptomycin), 2 μM of SB431542, 0.04 μM of RG108, 0.5 M of Bix01294, 2 μM of Bay K 8644.

Another more preferred reprogramming medium is formulated as: Advanced DMEM/F12 containing 2 mM of glutamine (Glutamax), penicillin and streptomycin (100 U/mL of penicillin and 0.1 mg/mL of streptomycin), 0.4-1 μM of A83-01, 0.01 to 1 μM of RG108, 0.1 to 2 μM of Bix01294, 1 to 4 μM of Bay K 8644; most preferred reprogramming medium herein is formulated as: Advanced DMEM/F12 containing 2 mM of glutamine (Glutamax), penicillin and streptomycin (100 U/mL of penicillin and 0.1 mg/mL of streptomycin), 0.5 μM of A83-01, 0.04 μM of RG108, 0.5 M of Bix01294, 2 μM of Bay K 8644.

The present invention also provides the application of the above small molecule compound combination or kit or reprogramming medium, which is to reprogram digestive tract derived epithelial cells to endodermal stem/progenitor cells using the above small molecule compound combination or kit or reprogramming medium on the basis of digestive tract derived stromal cells as trophoblast cells.

The reprogramming method for reprogramming digestive tract derived epithelial cells to endoderm stem/progenitor cells provided by the present invention comprises the following steps of:

1) using the isolated primary digestive tract derived epithelial cells as initiating cells to expand and culture the digestive tract derived epithelial cells;

2) treating the trophoblast cells with mitomycin-C, washing, and digesting the cells with enzymes for later use;

3) adding the trophoblast cells prepared in the step 2) to the digestive tract derived epithelial cells expanded and cultured in step 1), and continuing co-cultivation overnight;

4) changing to reprogramming medium on day 2, changing the medium every 2-3 days, and culturing for 7-15 days to obtain clones of induced endoderm stem/progenitor cells (hiEndoPCs).

In the above method, the initiating cells in the step 1) are digestive tract derived epithelial cells, including gastric and duodenal epithelial cells. Gastric epithelial cells are more easily obtained from the viewpoint of ease of clinical acquisition, and therefore the initiating cells are preferably gastric epithelial cells (hGECs), and particularly preferably NCAM (neural cell adhesion molecule) positive gastric epithelial cells (hGECs). In the step 1), NCAM positive gastric epithelial cells are preferably used as initiating cells, and cultured in Kubota medium at 37° C. in a 5% $CO_2$ incubator for 5 days.

The trophoblast cells in the step 2) are digestive tract derived stromal cells, including gastric subepithelial myofibroblasts or intestinal subepithelial myofibroblasts, preferably human gastric subepithelial myofibroblasts (aGSEMFs). In the step 2), human gastric subepithelial myofibroblasts (aGSEMFs) are preferably treated with mitomycin-C for 2-3 hours, and then the cells are washed with PBS, and then the cells are digested with TrypLE enzyme.

In the step 3), the trophoblast cells prepared in the step 2) are preferably added at a density of 1 to $3\times10^5$ per square centimeter to the digestive tract derived epithelial cells cultured for 5 days in the step 1), and cultured at 37° C. in a 5% $CO_2$ incubator overnight (12-16 hours).

The reprogramming medium in the step 4) is a mixture of the small molecule compound combination with the basal medium and the basal additive components for cell culture, and the specific compositions thereof are as described above.

Specifically, the method for reprogramming digestive tract derived epithelial cells to endodermal stem/progenitor cells, comprises the following steps of:

1) using the isolated primary digestive tract derived epithelial cells as initiating cells, and culturing in a serum-free Kubota's medium at 37° C. in a 5% $CO_2$ incubator for 5 days;

2) treating the trophoblast cells with mitomycin-C for 2-3 hours, washing the cells with PBS, and digesting the cells with TrypLE enzyme;

3) adding the trophoblast cells prepared in the step 2) at a density of 1 to $3\times10^5$ per square centimeter to the initiating epithelial cells cultured for 4-5 days in the step 1), and co-culturing at 37° C. in a 5% $CO_2$ incubator overnight (12-16 hours).

4) changing to reprogramming medium on day 2, changing the medium every 2-3 days, and culturing for 7-15 days to obtain clones of human induced endodermal progenitor cells (hiEndoPCs).

The endodermal stem/progenitor cells (hiEndoPCs) obtained by the above reprogramming method are also incorporated in the present invention.

The present invention also provides a method for passage of endodermal stem/progenitor cells (hiEndoPCs), comprising the following steps of:

1) preparation before passage: seeding the adult human gastric subepithelial myofibroblasts (aGSEMFs) treated with mitomycin-C (10 μg/mL) in a well plates, or about 3 hours in advance, coating Fibronectin (FN), Cell-TAK (CT, cell tissue adhesive) glue in the well plates and dring at room temperature;

2) preparation of medium for passage: Advanced DMEM/DF12+AWF (A83-01 0.5 μM+Wnt3a 50 ng/mL+bFGF 10 ng/mL), or Advanced DMEM/DF12+A (A83-01, 0.5 μM);

3) manually picking the clones of endodermal stem/progenitor cells (hiEndoPCs) and dividing them into small pieces at a ratio of about 1:3-, placing them in FN+AWF, CT+AWF or, trophoblast [trophoblast cells, adult human gastric subepithelial myofibroblasts aGSEMFs) treated with mitomycin-C (10 μg/mL)]+A medium at 37° C. in a 5% $CO_2$ incubator to subculture so as to obtain passaged endodermal stem/progenitor cells.

The application of endodermal stem/progenitor cells (hiEndoPCs) or passaged endodermal stem/progenitor cells obtained above for inducing differentiation into liver cells, pancreatic β cells, and intestinal cells is also incorporated in the present invention.

The present invention provides a small molecule compound combination for reprogramming digestive tract derived epithelial cells to endodermal stem/progenitor cells, a reprogramming kit, a reprogramming medium, and a method for reprogramming digestive tract derived epithelial cells to endodermal stem/progenitor cells. In the present invention, human gastric epithelial cells (hGECs) are used as initiating cells, and the muscle layers of human gastric tissue are isolated and cultured to obtain adult human gastric subepithelial myofibroblasts (aGSEMFs) as trophoblast cells, and human gastric epithelial cells lineage are reprogrammed to endodermal stem/progenitor cells with a small molecule compound combination with the support of trophoblast cells, which can be further subcultured and expanded. The endodermal stem/progenitor cells obtained by the present invention or the passaged cells thereof can be used in combination with the corresponding induced differentiation system to obtain mature liver cells, pancreatic β cells and intestinal cells, and are expected to provide ideal seed sources for cell therapy for liver diseases, diabetes and intestinal diseases, which has broad application prospects.

Hereinafter, the present invention will be further described in detail in conjunction with specific embodiments.

BRIEF DESCRIPTION OF THE DRAWINGS

FIG. 35A-35C show the results of induced differentiation of hiEndoPCs into the liver, A is the liver-specific gene expression map of hiEndoPC-Heps; B is the AFP and CK18 staining map of hiEndoPC-Heps (scale: 50 μM); C is the ALB and AFP Flow level detection map of hiEndoPC-Heps;

FIG. 36A-36B are bar graphs showing the gene expression level of hiEndoPCs induced differentiation into thyroid (A) and lung (B).

DETAILED DESCRIPTION OF THE INVENTION

Figure 1:
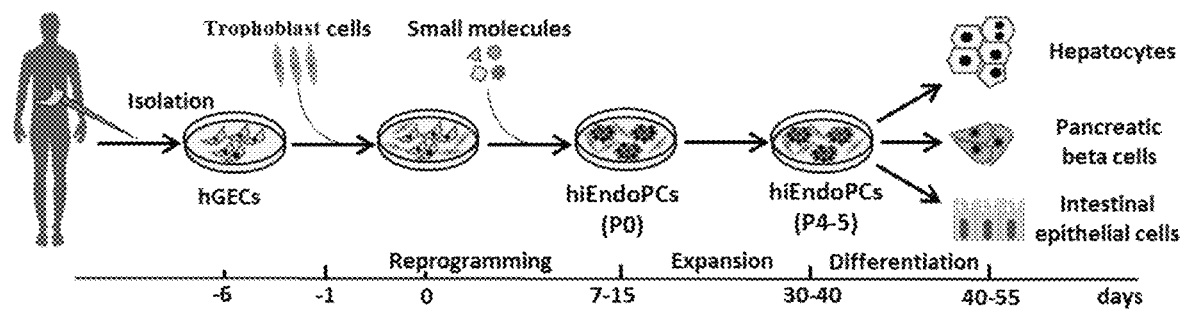
FIG. 1 is a technical roadmap of the present invention after determining the initiating cells, the initial small molecules, and the trophoblast cells.

After determining the initiating cells, the initial small molecules, and the trophoblast cells, the technical route of the present invention (shown in 1) is that: obtaining human gastric epithelial cells (hGECs) as initiating cells, and isolating gastric subepithelial myofibroblasts (aGSEMFs) as trophoblast cells from the muscle layer of human gastric tissue, screening appropriate small molecule combinations and reprogramming hGECs to endodermal stem/progenitor cells with the support of aGSEMFs.

Firstly, human gastric epithelial cells (hGECs) were isolated and cultured as initiating cells for lineage reprogramming, and the combination of eight small molecule were determined by preliminary screening: SB431542+VPA+PD0325901+RG108+Bix01294+BayK8644+PS48+FBP. hGECs could be reprogrammed into induced endodermal progenitor cells (hiEndoPCs)-like clones by the small molecules under conditions of aGSEMFs as a trophoblast cells. Based on the ability to develop endodermal progenitor-like clones, the reprogramming system, including small molecule compounds and trophoblast cells, were optimized and finally, the combination of Bix01294+BayK8644+RG108+SB431542 (BBRS) was determined as the optimal small molecule compound combination. And the necessary small molecule compound that assured successful reprogramming was SB431542. Since the human gastric subepithelial myofibroblasts (GSEMFs) as the trophoblast cells, were the easiest to access, therefore the optimal reprogramming system was the combination of BBRS+GSEMFs. And the reprogramming efficiency under this condition was 4%-6%. Moreover, the present invention also confirmed that induced endodermal progenitor cells (hiEndoPCs) were derived from NCAM-positive hGECs, achieving precise localization of the initiating cells.

Secondly, the endoderm-specific markers of hiEndoPCs viewing from the perspect of gene expression, proteins expression, epigenetic levels, genome-wide expression levels, and cell micromorphology, cell proliferation, and endoderm differentiation potential were analyzed comprehensively. The expressions in hiEndoPCs of common endodermal progenitor cell-specific transcription factors FOXA2, SOX9, HNF1B, PDX1, GATA4, other stem/progenitor cell-specific proteins CXCR4, EPCAM, LGR5, CK19 and gastric epithelial-specific markers MMC6, GASTRIN were first detected. It was found that the endodermal marker genes were significantly up-regulated in hiEndoPCs when compared with hGECs, while the gastric-specific genes were not expressed, which confirmed the successful reprogramming of hGECs to endoderm progenitor cells. The epigenetic analysis also showed significant changes in cells after reprogramming, acquiring molecular features of endodermal progenitor cells. Deep sequencing analysis revealed that the precise developmental stage of hiEndoPCs were located between the endoderm developmental stages of the hESCs-derived original digestive tract (PGT) and the posterior foregut (PFG), and were more closer to PFG Additionally, hiEndoPCs have the characteristics of microscopic feature of stem cells and could be passaged 4-6 times. Although the expansion potential of hiEndoPCs is limited when compared to ESCs or iPSCs, the genome of the cells within a limited number of passages was relatively stable, safer, and more conducive to cell therapy in the future. Theoretically, $10^9$ cells could be obtained from $10^6$ initiating cells via reprogramming and 4-6 times amplification, which is sufficient for cell therapy for one person. Since endodermal progenitor cells in vivo have the potential to differentiate into pancreas, liver, intestine, lung, and thyroid gland during development, hiEndoPCs were then tested and we confirmed that hiEndoPCs has the ability to form functional pancreatic beta cells, hepatocytes, and intestinal cells when using induced differentiation conditions correspondingly.

The methods used in the following examples are conventional methods, unless otherwise specified. For specific steps, see: "MolecuLar Cloning: A Laboratory Manual" (Sambrook, J., Russell, David W., MolecuLar Cloning: A Laboratory Manual, 3rd edition, 2001, NY, Cold Spring Harbor).

The percentage concentration is a mass/mass (W/W, unit of g/100 g) percent concentration, mass/volume (W/V, unit of g/100 mL) percent concentration, or volume/volume (V/V, units of mL/100 mL) percent concentration, unless otherwise specified.

Access to the various biological materials described in the examples is merely provided for an access in the experiment for the purpose of specific disclosure, and should not be considered as a limitation on the source of the biomaterial of the present invention. In fact, the sources of biological materials used are widely available, and any biological materials that are available without legal and ethical violations can be replaced and used in accordance with the instructions in the examples.

The examples are implemented on the premise of the technical solution of the present invention, and detailed embodiments and specific operation process are given. Although the examples will be helpful for understanding the present invention, the scope of protection in the present invention is not limited to the following examples.

Example 1. Establishment of a System for Inducing Conversion of Human Gastric Epithelial Cells to Endoderm Progenitor Cells by Small Molecule Compounds The target cells of reprogramming in this invention are endoderm progenitor cells, and the liver, pancreas, biliary tract, stomach, intestine, etc. are all derived from endoderm. Given the same germ layer origin, the epigenetic similarity, and the less reprogramming barrier, we believed stomach cells were the appropriate initiating cell type. Furthermore, the normal stomach tissues could be obtained easily from the gastrointestinal surgery such as major gastrectomy or gastric cancer resection when some normal stomach or duodenal tissues are inevitably abandoned as medical waste. And the normal stomach or duodenal tissue was also available by gastroscopy with follow-up biopsies after the treatment of gastric ulcer or duodenal ulcer. Generally, gastric epithelial cells as the initiating cells from the normal stomach tissues was feasible. In the present invention, we established culture system for gastric epithelial cells and trophoblast cells, and then performed reprogramming using a total of eight small molecules selected from the four major classes with the digestive tract myofibroblasts as trophoblast cells. Under these conditions, endodermal stem/progenitor-like clones were successfully produced from gastric epithelial or duodenal epithelial cells. After the reprogramming was successful, the reprogramming system was further optimized to find the optimal combination of small molecules and the essential small molecules. Finally, due to the heterogeneity of the initiating cells, we then separated the initiating cells into different sections to identify the subset of the initiating cells which could be reprogrammed successfully.

The general strategy for reprogramming gastrointestinal tract (GI-tract)-derived epithelial cells into endoderm stem/progenitor cells was as follows:

1, In the selection of the initiating cells, because the liver, pancreas, GI-tract and other internal organs are all derived from endodermal progenitor cells, therefore they are same origin and have closer affinities and more epigenetic similarity when compared to other germ layer-derived cells. In addition, they are all belong to epithelial cell types, therefore the MET barriers can be omitted and cell conversion between them is relatively easy during the conversion process. Furthermore, the cells of GI-tract tissues are frequently renewed, a large number of cells are actively proliferating, and proliferating cells or progenitor cells are more easily reprogrammed. As the channel that connects the various organs of the internal organs, large number of GI-tract tissues are accessible after gastrointestinal surgery and the gastroduodenal biopsy. Therefore, GI-tract-derived human gastric epithelial cells (hGECs) as the initiating cells has the advantage over the widely used fibroblasts to reprogram into endodermal progenitor cells in epigenetic similarity, epithelial property, the number of proliferating progenitor cells and the feasibility of clinical operation.

2, In the selection of small molecules, four groups of well-defined small molecules capable of positively regulating reprogramming are screened:

(1) Signaling pathway inhibitor: SB431542 (SB) or A83-01 (A83) is the TGF-β signaling pathway inhibitor. SB or A83 can replace Sox2 to produce iPSCs when combined with transcriptional factors, Oct4, Klf4, c-Myc. The other small molecule is MAPK ERK signaling pathway inhibitor, PD0325901 (PD), the combination of PD and SB (or A83) can increase reprogramming efficiency more than 100 times and greatly reduce reprogramming time;

(2) Epigenetic modifiers: the histone deacetylase inhibitor VPA, VPA can even replace Klf4, c-Myc, and can promote the formation of iPSCs when combined with Oct4, Sox2. The histone methyltransferase inhibitor Bix01294 (BIX) and DNA methyltransferase inhibitor RG108 (RG) can also significantly improve reprogramming efficiency;

(3) Calcium channel agonist: Bay K 8644 (Bay), the combination of Bay and Bix can replace Sox2 and c-Myc;

(4) Metabolic pathway regulator: the phosphoinositide-dependent protein kinase 1 agonist PS48, and the phosphofructokinase agonist FBP can facilitate the transition from energy metabolism oxidative phosphorylation of energy metabolism of mature cell to anaerobic glycolysis of stem cells, thereby improving reprogramming efficiency.

3, In the selection of trophoblast cells, in order to promote the production and maintenance of endoderm progenitor cells, GI-tract myofibroblasts closely related to endoderm organs were selected as trophoblast cells. These cells could affect the development of endoderm organs and support the expansion of endoderm progenitor cells by the paracrine in the early stage of development.

I. Isolation, Culture and Phenotypic Identification of Gastric Epithelial Cells

Materials and Methods

The materials listed and methods below are derived from the original records of the experiment. In the practical application of the present invention, it can be implemented using commercially available materials and methods suitable for industrial applications, without being limited by the listed experiments.

(I) Experimental Materials (1) Experimental Tissues

Gastric and duodenal tissues from surgery or biopsy were provided by the Department of general surgery of the General Hospital of the Chinese People's Liberation Army and the 307 Hospital of the Chinese People's Liberation Army. The aborted fetal tissues were provided by the General Hospital of the People's Liberation Army. All patients providing the tissues were informed and signed informed consents. Use of the tissue specimens was approved by the Ethics Committees of the General Hospital of the People's Liberation Army and the 307 Hospital.

(2) Experimental Equipment

Laser confocal microscope (Zeiss), thermostat water bath (long wind), refrigerated centrifuge (Eppendorf), inverted phase contrast microscope (Leica), surgical instruments (surgical shank, blade, ophthalmic straight forceps, curved forceps, scissors), and small dishs for laser focus (NEST).

(3) Main Reagents and Preparation

1. Preparation of Kubota Medium (KM) medium: One bag of RPMI 1640 (Gibco) powder was dissolved in 1 L of deionized water, and 1× penicillin-streptomycin, $10^{-9}$ M of Zinc SuLfate heptahydrate (Sigma), 0.54 g of Nicotinamide (Sigma), 5 mg of InsuLin (Sigma), $10^{-6}$ M of hydrocortisone (Sigma), 2 g of $NaHCO_3$ (Sigma), $5 \times 10^{-5}$ M of β-mercaptoethanol (Sigma), 30 nM of Selenium (Sigma), free fatty acid (Sigma), 10 μg/mL of High density lipoprotein (Sigma), 1 g of Bovine Serum Albumin (purchased from Gibco), 5 mg of Transferrin (Sigma), 2 mM of Glutamax (purchased from Gibco) were added.

2. Preparation of $Ca^{2+}$- and $Mg^{2+}$-free PBS: 0.24 g of $KH_2PO_4$, 8.0 g of NaCl, 0.2 g of KCl, and 1.44 g of $Na_2HPO_4$ were dissolved in 1 L of deionized water. The reagents may be added in equal proportion according to the volume prepared. After finishing the preparation, the solution was filtered with a 0.45 μM filter membrane and then autoclaved or directly filtered through a 0.22 filter membrane for use.

3. Main Antibodies

TABLE 1

Primary antibodies for immunofluorescence detection of human gastric epithelial cells (hGECs)

| Primary antibody | Company | Item No. | Genus of primary antibody | dilution ratio |
| --- | --- | --- | --- | --- |
| CXCR4 (C-X-C motif chemokine receptor 4) | Abcam | ab77909 | Rabbit | 200 |
| EPCAM (Epithelial cell adhesion molecule) | Neomarker | MS-181 | Mouse immunoglobulin 1 | 200 |

TABLE 1-continued

Primary antibodies for immunofluorescence detection of human gastric epithelial cells (hGECs)

| Primary antibody | Company | Item No. | Genus of primary antibody | dilution ratio |
|---|---|---|---|---|
| FOXA2 (Forkhead coding box protein A2) | R&D | AF2400 | Goat immunoglobulin | 100 |
| SOX9 (Sex determination region Y gene 9) | Abcam | ab76997 | Mouse immunoglobulin 2a | 50 |
| CK19 (Cytokeratin 19) | Abcam | ab7754 | Mouse immunoglobulin 2a | 200 |
| LGR5 (Repeated leucine-rich G-protein coupled receptor 5) | Sigma | HPA012530 | Rabbit | 350 |
| GASTRIN (GAST) | Santa Cruz | sc-7783 | Goat | 50 |
| MUC6 (Mucosal protein-6) | Abcam | ab49462 | Mouse immunoglobulin 1 | 50 |

TABLE 2

Secondary antibodies for immunofluorescence detection of human gastric epithelial cells (hGECs)

| Secondary antibody | Company | Item No. | dilution ratio |
|---|---|---|---|
| Alexa Fluor ® 568 Goat anti-mouse immunoglobulin 1 (γ1) | Invitrogen | A21124 | 400 |
| Alexa Fluor ® 488 Goat anti-mouse immunoglobulin 2a (γ2a) | Invitrogen | A21131 | 400 |
| Alexa Fluor ® 568 Goat anti-mouse immunoglobulin (H + L) | Invitrogen | A11031 | 400 |
| Alexa Fluor ® 488 Donkey anti-mouse immunoglobulin (H + L) | Invitrogen | A-21202 | 400 |
| Alexa Fluor ® 568 Donkey anti-goat immunoglobulin (H + L) | Invitrogen | A11057 | 400 |
| Alexa Fluor ® 488 Donkey anti-rabbit immunoglobulin(H + L) | Invitrogen | A21206 | 400 |
| Alexa Fluor ® 568 Goat anti-mouse immunoglobulin 2a (γ2a) | Invitrogen | A21134 | 400 |

4. Preparation of 0.075 mg/mL of type IV collagenase: 20 mg of type IV collagenase (Sigma) and 6 mg of DNase A were added to 200 mL of Advanced RPMI 1640 medium (purchased from Gibco).

5. Other reagents and materials: TrypLE digestive enzyme (purchased from Invitrogen), 4% (V/V) of paraformaldehyde (purchased from Sigma), DNase A (Invitrogen), 0.2% (V/V) of Triton X-100 (Polyethylene glycol octyl phenyl ether, purchased from Sigma), fetal bovine serum (FBS, Gibco), sodium citrate buffer (purchased from Sigma), DAPI (4',6-diamidino-2-phenylindole, Sigma), Immunohistochemical kit (Vector lab).

(2) Experimental Methods and Results
(1) Acquisition of Gastric Epithelial Cells Gastric epithelial cells may be purchased directly; the gastric antrum, pylorus or duodenal mucosal epithelial cells may also be obtained by isolation and culture as follows:

1) The prepared type IV collagenase was placed at room temperature or 37° C. for balance in advance, PBS was placed on ice to be pre-cooled, 1000× penicillin-streptomycin was prepared, and the surgical instruments were sterilized with 75% (V/V) alcohol.

2) Fresh gastric antrum, pylorus or duodenal tissue specimens were obtained after gastric operation from the hospital, and they were transported to the laboratory in the ice boxes within half an hour.

3) 5× penicillin-streptomycin was added to the pre-cooled PBS to wash the obtained tissue specimens 4-5 times, so as to thoroughly wash away residual blood.

4) After washing, the mucosal layers and the muscular layers of the gastric tissue were separated using blunt dissection, and the mucosal layers and the muscular layers were also washed with cold PBS containing 5× penicillin-streptomycin respectively, and then subjected to different treatments.

5) The mucosal layers were cut or mashed using a pair of scissors in combination with scalpel, an appropriate amount of type IV collagenase (0.075 mg/mL) was added thereto to digest in a 37° C. water bath, with shaking every 2-3 minutes. The sedimentation of the isolate was performed every 8-10 minutes, with settling on ice for 2-3 minutes. Then the supernatant was carefully collected by a dropper, and the remainder was continuously digested with an appropriate amount of enzyme.

6) The step 5 was repeated until terminated without significant bulk tissue. 7) The pre-cooled PBS was added to the collected supernatant, which was centrifuged at 4° C., 1200 rpm (revolution/minute) for 5 minutes, washed 3-4 times, so as to fully remove the residual digestive enzymes in the cells.

8) The cells were seeded at a suitable density with K1\4 medium containing 8% (V/V) of fetal bovine serum (FBS) and 1× penicillin-streptomycin to adherent overnight, and cultured with serum-free KM medium on the next day.

9) The medium was changed every 2-3 days during the culture process, and the reprogramming was started after 4-5 days of the culture.

Figure 2:
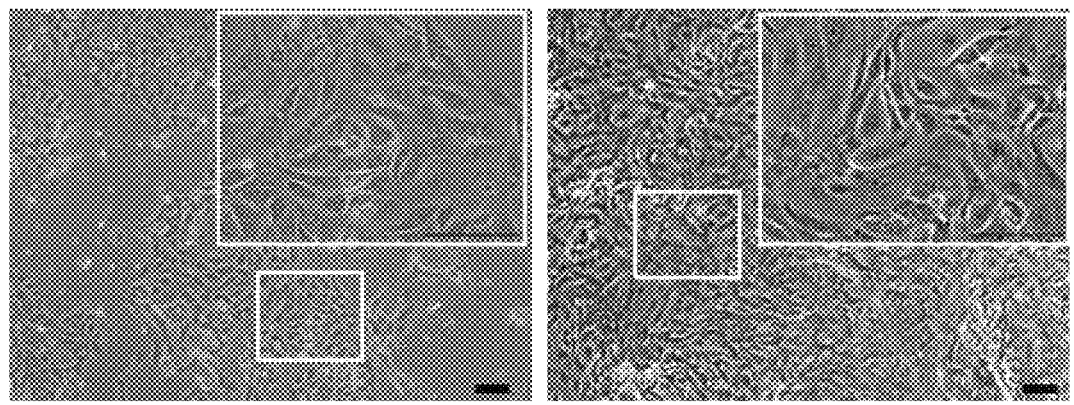
FIG. 2 is the morphology map of gastric epithelial cells (hGECs) and duodenal epithelial cells (hDECs) cultured for 4-5 days under a phase contrast microscope (scale: 100 μm)

RESULTS: The mucosal and muscular layers could be obtained by separating clinically obtained gastric or duodenal tissues. The mucosal layers were used to separate gastric or duodenal epithelial cells, and the muscular layers were used to separate trophoblast cells—myofibroblasts. According to the method of tissue separation of the stomach or duodenal epithelium in the experimental procedures, cells which are close to the crypt were commonly obtained. Cultured in serum-free Epithelial cell-screening medium, Kubota's medium, human gastric epithelial cells (hGECs) and duodenal epithelial cells (hDECs) exhibited typical dance-like epithelial morphology in culture (see FIG. 2). It was observed that the number of cells reached the most after days 4-5, then the cells entered a state of gradual apoptosis. Therefore, cells which have been cultured for 4-5 days were usually used as initiating cells for reprogramming to endoderm progenitor cells. Moreover, it was found from the observation and analysis on isolation and culture of cells in different parts of the dozens of stomach and duodenum that, the tissues derived from the gastric antrum, pylorus, or duodenum were the best in terms of cell adherence and growth. The tissues of the body or the fundus of stomach, and cardia were hardly adhered or difficult to culture. Since the source of duodenal tissue was relatively few, the gastric epithelial cells derived from the tissues of gastric antrum or gastric pylorus were isolated and used as reprogramming initiating cells in the subsequent experiments, unless otherwise mentioned.

(2) Acquisition of Myofibroblasts

Myofibroblasts may be purchased directly; gastrointestinal subepithelial myofibroblasts may also be isolated and cultured by the following adherence methods:

1) The gastric or duodenal muscular layers obtained as described above were fully mashed into small tissue pieces using a surgical blade. The small tissue pieces should be as small as possible. A small amount of high sugar medium or KM medium containing 15% (V/V) of fetal bovine serum (FBS) was added to wet the tissue pieces, and the tissue pieces were evenly coating in a 10 cm culture dish using a 1 ml small dropper, and placed upside down at 37° C. in a incubator for 30 minutes. The remaining stromal cells were isolated and cultured as described above.

2) After adhering for 30 minutes, the stromal cell growth medium was added along the edge of the culture dish, and the cells were cultured at 37° C. in a 5% $CO_2$ incubator.

3) After 5-7 days of culture, it was observed that spindle cells were climbed out from the tissue pieces. After 2 weeks, a large number of cells climbed out and grew. At this time, the cells were passaged and frozen. Thus, fetal gastric subepithelial myofibroblasts (fGSEMFs), adult human gastric subepithelial myofibroblasts (aGSEMFs), fetal intestinal subepithelial myofibroblasts (fISEMFs), and fetal diaphragm stromal cells (fDCs) were obtained. Frozen cells may provide trophoblast cells for later reprogramming.

Figure 3:
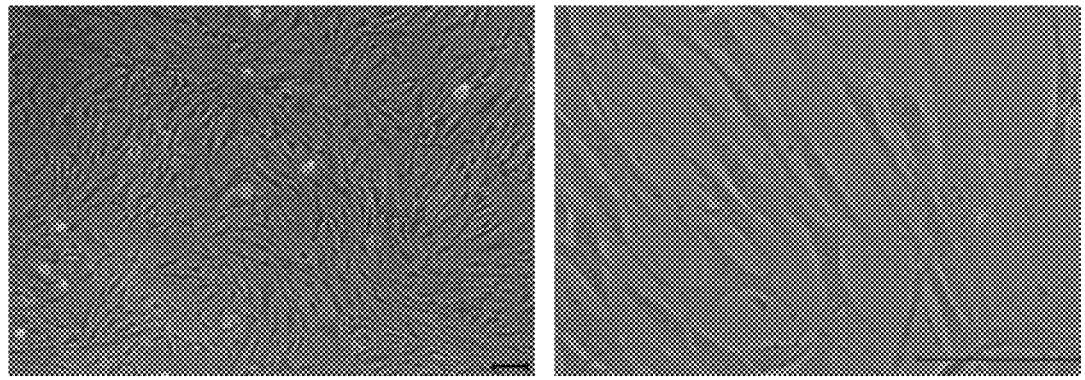
FIG. 3 is the morphology map of gastric muscle fibroblasts subcultured under a phase contrast microscope (scale: 100 μm)

RESULTS: The obtained gastric or duodenal muscular layers were mechanically mashed into small pieces. The myofibroblasts (GSEMFs) were isolated and cultured using tissue adherence method. The tissue was adhered for about 4-7 days, and it was seen that the spindle cells climbed out of the tissue pieces, and the passage was performed during 10-14 days. The subcultured myofibroblasts were exhibited a typical morphology of long spindle-like fibroblasts (as shown in FIG. 3).

(3) Immunofluorescence detection of gastric epithelial cells Immunofluorescence identification of the characterization of human gastric epithelial cells (hGECs) was performed, including the following operations (primary and secondary antibodies were shown in Tables 1 and 2, respectively):

1) The cells were fixed with 4% (V/V) of paraformaldehyde for 10-15 min, and washed twice with PBS.

2) The membranes were broken with 0.2% (V/V) of Triton X-100 for 10 minutes, and washed with PBS again.

3) Blocked with the serum derived from the genus of the secondary antibody for 1 hour, and washed with PBS again.

4) Incubated with the corresponding primary antibody at 4° C. overnight, and washed with PBS for 2-3 times.

5) Incubated with the corresponding secondary antibody for 1 hour at room temperature in the dark, and washed with PBS for 2-3 times.

6) Incubated with DAPI for 15 minutes at room temperature in the dark.

7) Observed and imaged under a laser confocal fluorescence microscope.

Figure 4:
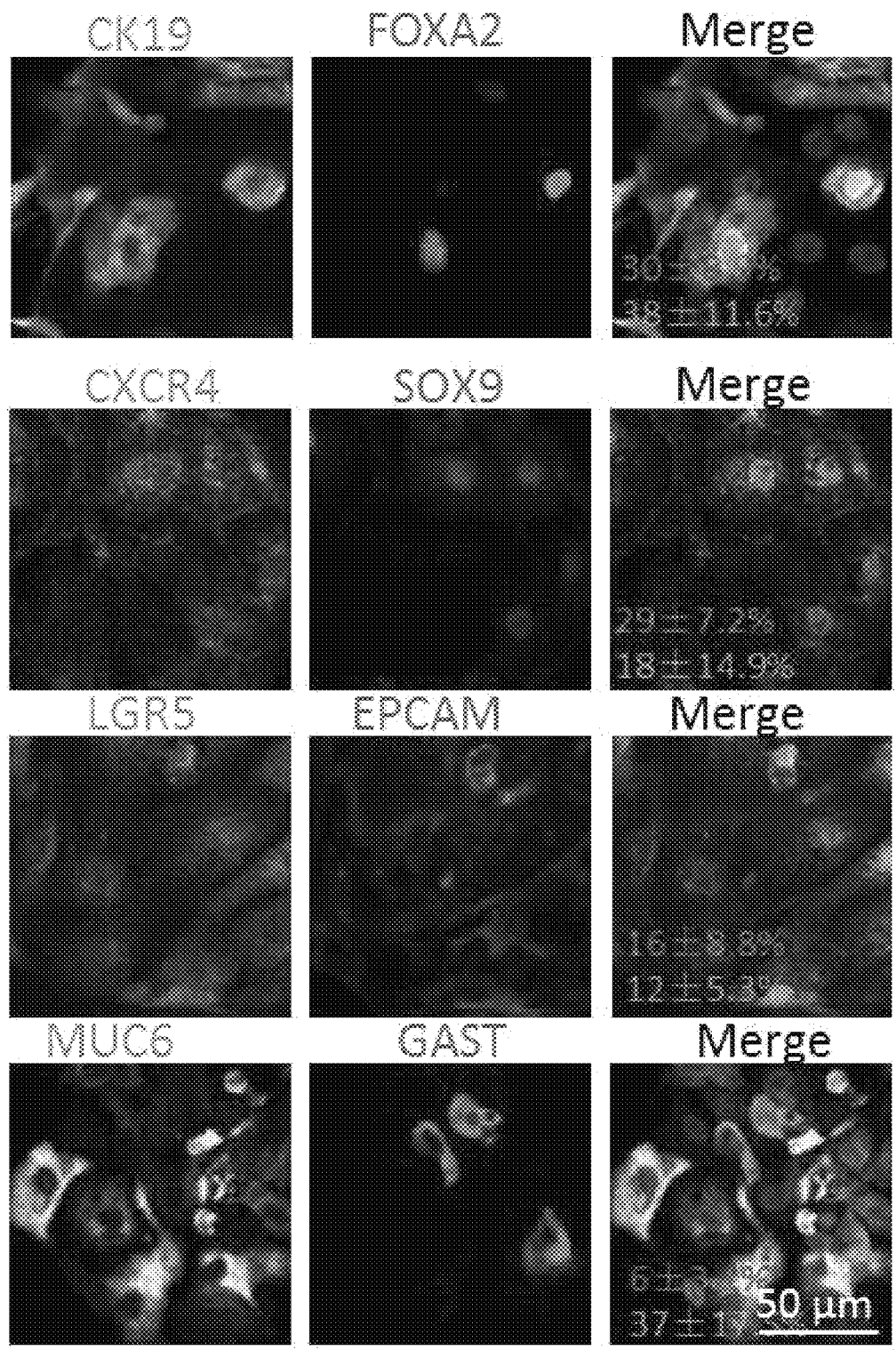
FIG. 4 shows the expression of gastric-specific and endodermal progenitor-specific proteins in gastric epithelial cells.

RESULTS: As shown in FIG. 4, it was found from the immunofluorescence staining that human gastric epithelial cells (hGECs) expressed endodermal progenitor cells markers such as CK19, FOXA2, CXCR4, SOX9, LGR5, EPCAM, and the like, at a low level, while highly expressing the gastric characteristic marker MUC6 and GAST.

The first part "Isolation, culture and phenotypic identification of gastric epithelial cells" successfully established an isolation and culture system for gastric epithelial cells and myofibroblasts in gastric antrum or pylorus. Human gastric epithelial cells (hGECs) cultured in vitro showed typical epithelioid morphology. Since the cells in the crypt were usually primitive (compared to the type of mature gastric cells), a certain degree of proliferation could be achieved. Human gastric epithelial cells (hGECs) highly expressed gastric-specific markers, and expressed early endodermal progenitor markers at a low level, which was consistent with our previous speculation. Since they partially expressed certain markers in endodermal progenitor cells, the reprogramming obstacles during reprogramming to endoderm progenitor cells were relatively small; therefore they were good sources of initiating cells for transformation to endoderm progenitor cells. However, the gastric epithelium characteristic markers of human gastric epithelial cells (hGECs) had to be lost during reprogramming. The source and culture problems of the initiating cells were solved, and the characteristics were also preliminarily determined. The next step was to reprogram to the endodermal progenitor cells with them as the initiating cells.

II. The Conversion of Gastric Epithelial Cells to Endoderm Progenitor Cells Induced by Small Molecule Compounds and Trophoblast Cells Materials and Methods (I) Experimental Materials (1) Experimental Cells Human gastric epithelial cells (hGECs) and adult human gastric subepithelial myofibroblasts (aGSEMFs) were prepared and stored in the step I.

(2) Experimental Equipment

Inverted phase contrast microscope (Leica), microscope graticule, refrigerated centrifuge (Eppendorf), 12-well plates.

(3) Main Reagents and Preparation

1. Basic Reagents

Advanced DMEM/F-12 medium, Advanced RPMI 1640 medium, NEAA (non-essential amino acids), TrypLE digestive enzyme, Glutamine (Glutamax), Dispase were all purchased from Gibco Company, penicillin-streptomycin and mitomycin-C(Sigma).

2. Small Molecule Compounds

TABLE 3

8 small molecule compounds (8M)

| Name of the small molecule | Concentration used | Company |
|---|---|---|
| FBP (Fructose diphosphate) | 3.5 mM | Sigma |
| Bay K 8644 (Flunitidine) | 2 μM | Stemgent |
| Bix01294 | 0.5 μM | Stemgent |
| SB431542 | 2 μM | Stemgent |
| Valproic Acid (VPA) | 0.5 mM | Stemgent |
| RG108 | 0.04 μM | Stemgent |
| PD0325901 | 0.5 μM | Stemgent |
| PS48 | 5 μM | Stemgent |

"Concentration used" means the concentration of each compound in Advanced DMEM/F-12 medium as a solvent.

3. Preparation of 8M Reprogramming Medium

Formulation: Advanced DMEM/F12+2 mM of Glutamine (Glutamax)+penicillin-streptomycin (100 U/mL of penicillin+0.1 mg/mL of streptomycin)+SB431542 (2 μM)+VPA (0.5 mM)+PD0325901 (0.5 μM)+RG108 (0.04 μM)+Bix01294 (0.5 μM)+Bay K 8644 (2 μM)+PS48 (5 μM)+FBP (3.5 mM).

The concentration of each component in the formulation is its concentration in Advanced DMEM/F-12 medium as a solvent.

(2) Experimental Methods and Results (1) The Conversion of Human Gastric Epithelial Cells (hGECs) or Duodenal Epithelial Cells (hDECs) to Induced Endodermal Progenitor Cells (hiEndoPCs) Mediated by Small Molecule Compounds The specific method included the following steps of:

1. Proliferation of the initiating cells: Primary isolated human gastric epithelial cells (hGECs) or duodenal epithelial cells (hDECs) were used as initiating cells, and cultured in Kubta medium (prepared according to the literature, literature source: Kubota, H., and Reid, L. M. (2000). Clonogenic hepatoblasts, common precursors for hepatocytic and biliary lineages, are lacking classical major histocompatibility complex class I antigen. Proc. Natl. Acad. Sci. USA 97, 12132-12137) at 37° C. in a 5% $CO_2$ incubator for 4-5 days, and the initiating cells were expanded.

2. Preparation of trophoblast cells: adult human gastric subepithelial myofibroblasts (aGSEMFs, the cells were obtained by separation of gastric tissue matrix layers, frozen in large quantities after culture and proliferation, and resuscitated in advance when necessary) as trophoblast cells were treated with mitomycin-C (10 μg/mL, for the purpose of losing mitosis of trophoblast cells) for 2-3 hours, washed with PBS for 3-4 times, the cells were digested by TrypLE enzyme, and then the cells were washed;

3. When human gastric epithelial cells (hGECs) or duodenal epithelial cells (hDECs) were cultured until day 5-6, the treated gastric subepithelial myofibroblasts were added at a suitable density (generally, density of $1-3\times10^5$ per square centimeter) to human gastric epithelial cells (hGECs) or duodenal epithelial cells (hDECs) being cultured, and placed at 37° C. in a 5% $CO_2$ incubator overnight (12-16 hours);

4. Reprogramming culture: on the second day after the addition of gastric subepithelial myofibroblasts, the medium was changed to 8M reprogramming medium, and changed every 2-3 days, and continuous observation was performed. Generally, induced endodermal progenitor cells (hiEndoPCs) were obtained after culturing for 1 week or 2 weeks more (7-15 days).

Results:

(1.1) Conversion of Human Gastric Epithelial Cells (hGECs) to Induced Endodermal Progenitor Cells (hiEndoPCs)

Figure 5:
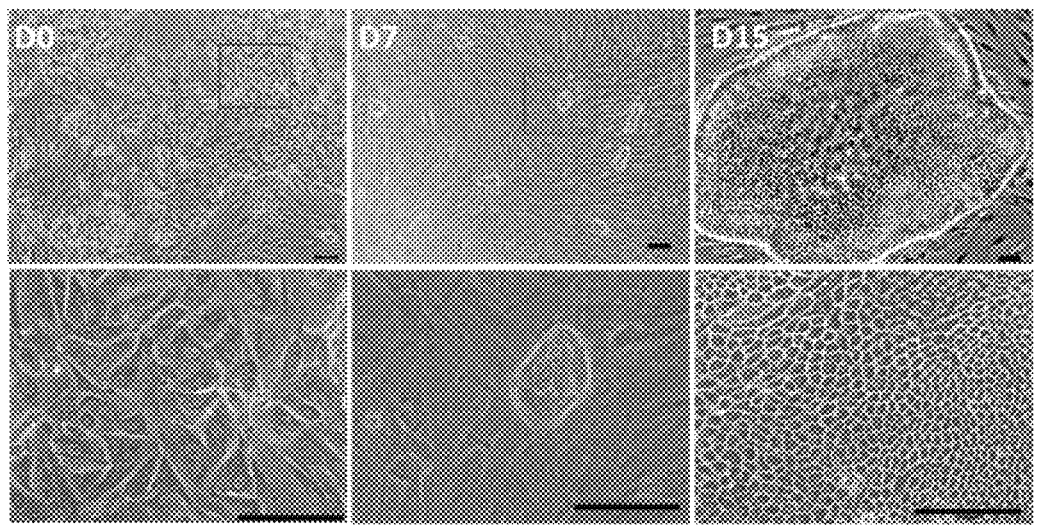
FIG. 5 is a dynamic process cell morphology map of human gastric epithelial cells (hGECs) reprogrammed to endodermal progenitor cells (hiEndoPCs) (scale: 100 μm)

The morphology of human gastric epithelial cells (hGECs) occurred clear changes constantly under the condition of 8M reprogramming medium and isolated cultured gastrointestinal subepithelial myofibroblasts (GSEMFs) as trophoblast cells using 8 small molecule compounds (8M, as shown in Table 3). From the beginning of the dance-like or multi-horned epithelium with larger morphology, small cell clones with clearer boundaries began to appear on the 7th day. On the 15th day, human gastric epithelial cells (hGECs) have been reprogramming to a typical endodermal stem/progenitor cell-like clone (G-hiEndoPCs) with clear boundaries and small and tight cells and a relatively uniform morphology, and a large nucleoplasm, as shown in FIG. 5 (The picture in the lower in FIG. 5 was the enlarged part of the box in the picture in the upper).

(1.2) Conversion of Human Duodenal Epithelial Cells (hDECs) to Endoderm Progenitor Cells (hiEndoPCs)

Figure 6:
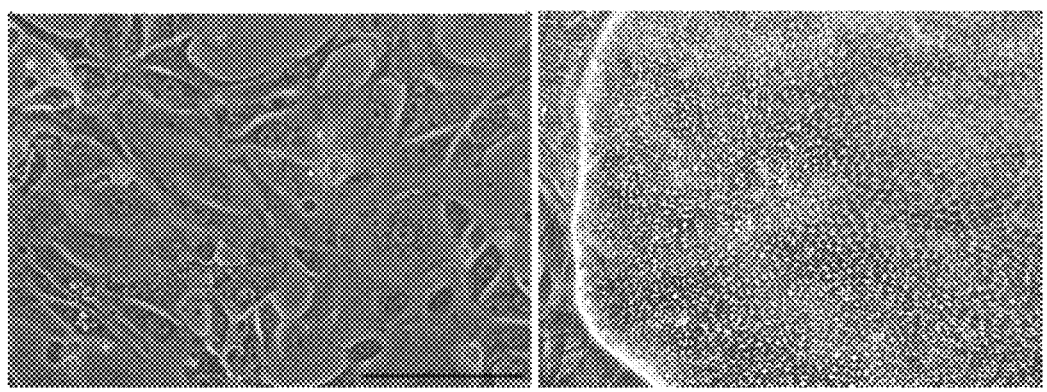
FIG. 6 shows the morphology map of human duodenal epithelial cells (hDECs) and their derived endoderm progenitor cells (hiEndoPCs) (scale: 100 μm)

Similarly, initiating from human duodenal epithelial cells (hDECs), under the action of 8M reprogramming medium and isolated cultured gastrointestinal subepithelial myofibroblasts (GSEMFs) as trophoblast cells, the typical endoderm stem/progenitor cell clones (D-hiEndoPCs) were also formed after inducing for 15 days (as shown in FIG. 6, the left picture of duodenal epithelial cells (hDECs), and the right picture of endoderm stem/progenitor cells (D-hiEndoPCs) produced by reprogramming of duodenal epithelial cells, having a morphology similar to that of G-hiEndoPCs (FIG. 5)). Due to the limited source of duodenal tissue, human gastric epithelial cells (hGECs) were usually used as initiating cells for reprogramming.

(1.3) Conversion of Only Human Gastric Epithelial Cells (hGECs) or Gastrointestinal Subepithelial Myofibroblasts (GSEMFs) as Initiating Cells to Endodermal Progenitor Cells (hiEndoPCs)

Figures 7A, 7B:
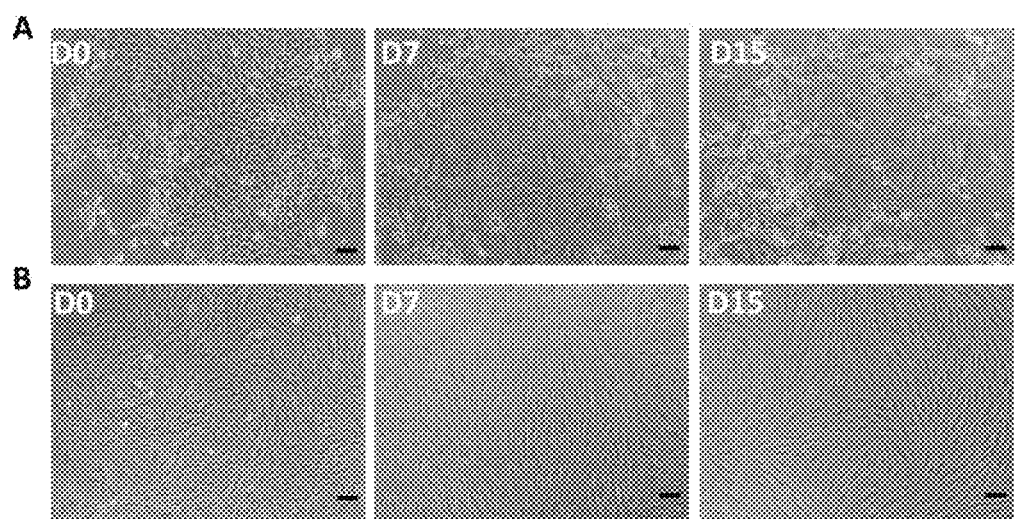
FIGS. 7A-7B are cell morphology maps of the initiating cells, human gastric epithelial cells (hGECs) (A) and the gastrointestinal myofibroblasts (GSEMFs) (B), respectively, of the reprogramming process (scale: 100 μm)

Endodermal stem/progenitor cell-like clones could not be formed without using small molecule compounds. However, only human gastric epithelial cells (hGECs) or gastrointestinal subepithelial myofibroblasts (GSEMFs) were used as initiating cells, respectively, they could not form endodermal stem/progenitor cell-like clones after culturing in 8M reprogramming medium for 15 days (as shown in FIGS. 7A-7B), indicating that the combination of small molecule compounds (8M), human gastric epithelial cells (hGECs), and gastrointestinal subepithelial myofibroblasts (GSEMFs) was an indispensable factor in the formation of endodermal progenitor cells (hiEndoPCs).

(2) Calculation of Clonal Formation Efficiency

The specific method included the following steps of:

1. Calculation of the total number of clones.

2. Calculation of the area of different clones using the microscope graticule: the area of each microscope microlattice was $0.0625$ $mm^2$, and the number of lattices occupied by the clone multiplied by $0.0625$ $mm^2$ was the area of each clone.

3. The evaluation of the efficiency of reprogramming is proformed by colligating number of clones and the area of the clones.

Figures 8A, 8B, 8C, 8D, 8E, 8F:
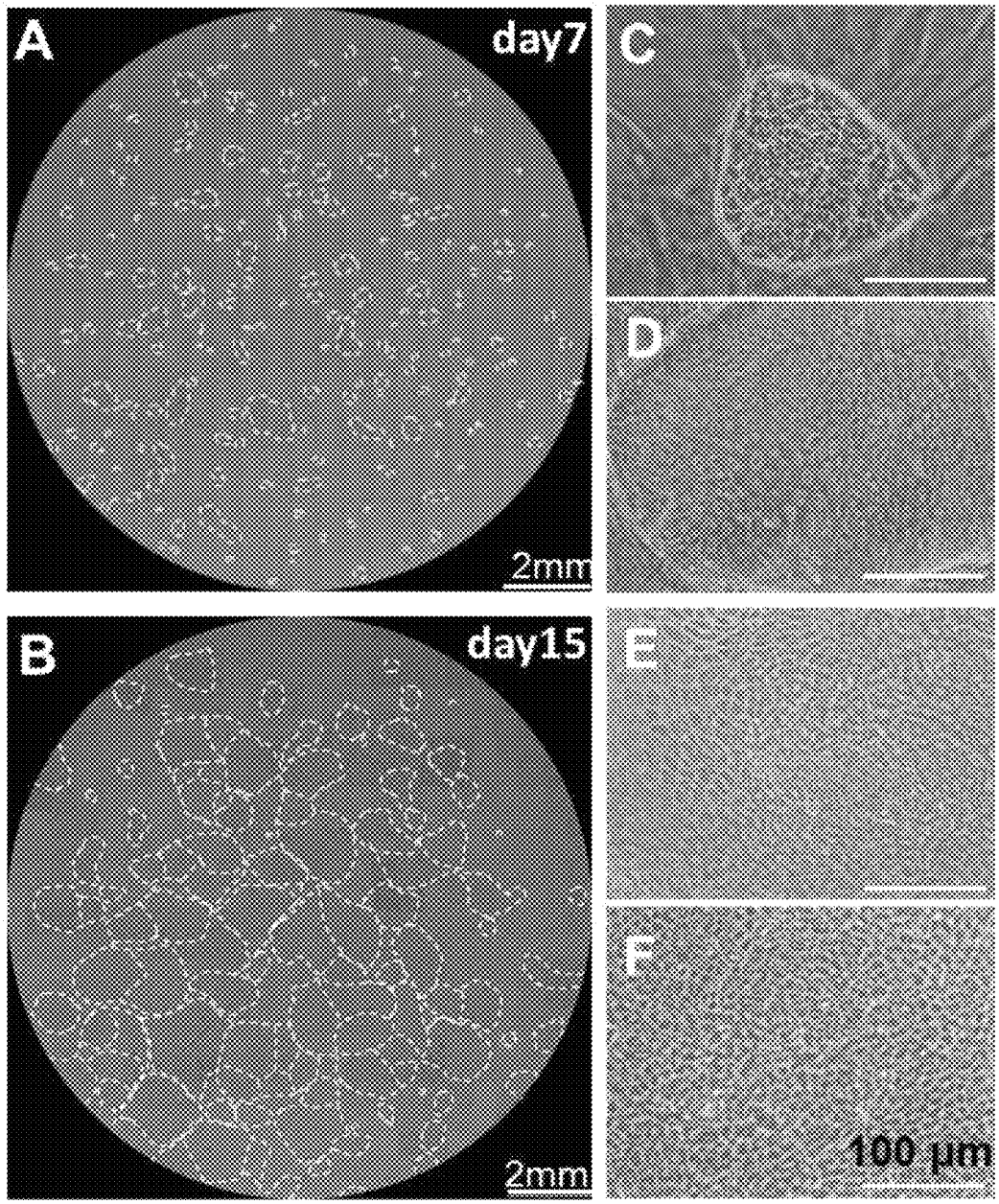
FIGS. 8A-8F are panoramic scan images of the clonal morphology, showing different clones on day 7 (A) and day 15 (B) (outline outline with dashed lines), C, D, E, F are specific forms of representative clones.
Figure 9:
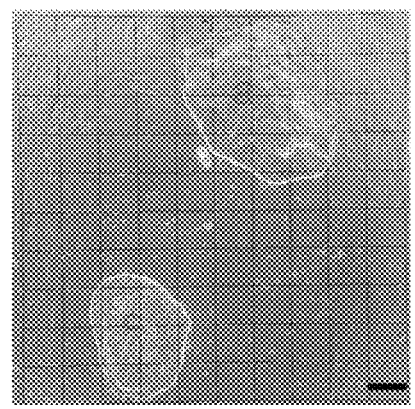
FIG. 9 is a schematic diagram of grids of clones of different sizes in the calculation of cloned area (scale: 250 μm)

RESULTS: In the foregoing observations, it has been found that small cell clones had begun to appear on day 7 of reprogramming, and the panoramic scan of the well plate showed that such small clones had clear boundaries and the number of small clones was very large (FIG. 8A), which were already in morphology close to the morphology of classical endoderm stem/progenitor cell clones (FIGS. 8C and 8D). Since the clonal morphology produced on day 15 of reprogramming was most typical (FIGS. 8E and 8F), colony formation efficiency was usually calculated at this time point. However, the growth rate of clones was faster from day 7 to day 15, and many clones were fused together to form a large clone upon the time point for calculation (FIG. 8B), so the number of clones was less upon calculation, but the total area was increasing. In order to reflect the reprogramming effect more objectively, the present experiment colligated the total number of clones and the number of clones and clone area under different areas, as the calculation method of reprogramming efficiency. Calculation of the area of different clones using the microscope graticule: the area of each microscope microlattice was $0.0625$ $mm^2$, and the number of lattices occupied by the clone multiplied by $0.0625$ $mm^2$ was the area of each clone. The calculation method for different sizes of cloned areas was shown in FIG. 9, and the calculation results were shown in Table 4.

TABLE 4

Calculation results for different sizes of cloned areas

| | Number of lattices | Area |
|---|---|---|
| a | 12 | 0.750 |
| b | 0.1 | 0.006 |
| c | 6 | 0.375 |

In the second part, human gastric epithelial cells (hGECs) were successfully reprogrammed to the phase of endodermal stem/progenitor cells (hiEndoPCs) under the condition of initially selected eight small molecules (8M) and adult human gastric subepithelial myofibroblasts (aGSEMFs) as trophoblast cells. Since the initial significant change that occurred during the reprogramming process was cellular morphology, the appearance of the stem/progenitor cell clones was used as the initial judgment for successful reprogramming. Human duodenal epithelial cells (hDECs) could also be reprogrammed to endodermal stem/progenitor cells (hiEndoPCs) using the same method. Small molecule compounds and trophoblast cells were essential elements during the reprogramming process. Although we have initially realized our vision, we still need to find the best reprogramming scheme, to improve the reprogramming efficiency as much as possible, and reduce the number of small molecule compounds. Moreover, the discovery of the key small molecules will have a very important role in the analysis of mechanism of reprogramming.

III. Optimization of the Reprogramming System of Small Molecule Compounds and Trophoblast Cells Materials and Methods (I) Experimental Materials (1) Experimental Cells Human gastric epithelial cells (hGECs), fetal gastric subepithelial myofibroblasts (fGSEMFs), adult human gastric subepithelial myofibroblasts (aGSEMFs), fetal intestinal subepithelial myofibroblasts (fISEMFs), fetal diaphragm stromal cells (fDCs) were prepared in the step I; mesenchymal stem cells (MSCs), mouse embryonic fibroblasts (MEFs), and adult human skin fibroblasts (HFFs) were derived from the foreskin tissue, and isolated and cultured in our laboratory.

(2) Experimental Equipment

Inverted phase contrast microscope (Leica), microscope graticule, 12-well plate.

(3) Main Reagents

1. Basic reagents: Advanced DMEM/F-12 medium, Advanced RPMI 1640 medium, NEAA (non-essential amino acids), Glutamine (Glutamax) were purchased from Gibco; penicillin-streptomycin, mitomycin-C were purchased from Sigma; TrypLE, Dispase digestive enzymes were purchased from Invitrogen; Matrigel gel was purchased from BD; Gelatin was purchased from Sigma.

2. Combination of small molecule compounds (8M): The types and concentration used were the same as that in the second part (see Table 3).

(2) Experimental Methods and Results (1) Preparation of conditioned medium for fetal intestinal subepithelial myofibroblasts (fISEMFs) or adult human gastric subepithelial myofibroblasts (aGSEMFs): fISEMFs cells or aGSEMFs cells were treated with mitomycin-C at a concentration of 10 μg/mL for 2-3 hours, washed with PBS for 3-4 times, then cultured with the addition of Advanced DMEM/F-12 medium, the medium was collected daily, filtered through a 0.22 μM filter, and stored at −80° C.

(2) Reprogramming of human gastric epithelial cells (hGECs) to endodermal progenitor cells (hiEndoPCs) supported by different trophoblast cells The specific method included the following steps of:

1) The treatment of human gastric epithelial cells as initiating cells (hGECs) was the same as that in the step II.

2) The preparation of various trophoblast cells was the same as that in the second part.

3) The reprogramming method was the same as the method in the second part.

4) The colonal formation efficiency under the support of small molecule compounds (8M) and various trophoblast cells, extracellular matrices or conditioned media was calculated on the 15th day of reprogramming, thereby finding the suitable trophoblast cells.

Figure 10:
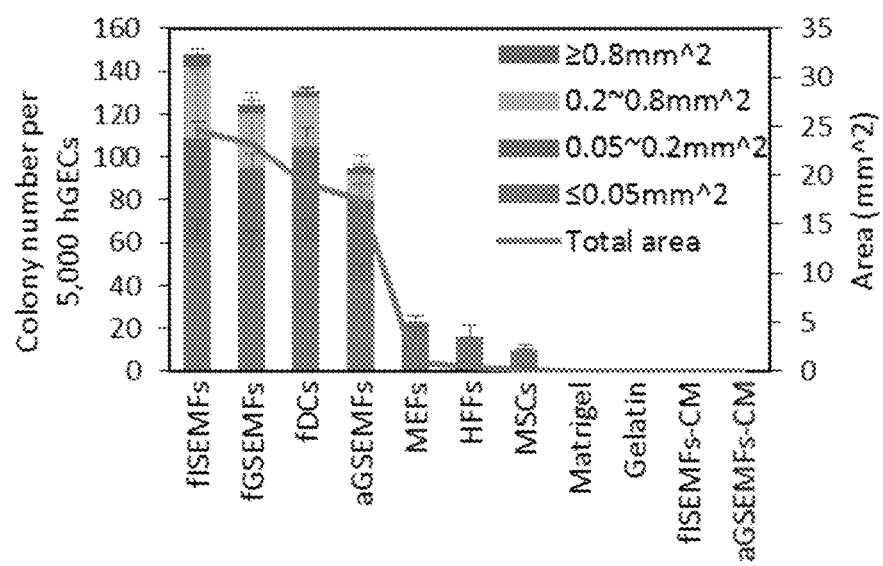
FIG. 10 is a bar graph of the efficiency of cloning formation of small molecule compounds (8M) with various trophoblast cells, extracellular matrix or conditioned medium (reprogramming efficiency under different support conditions)
Figure 11:
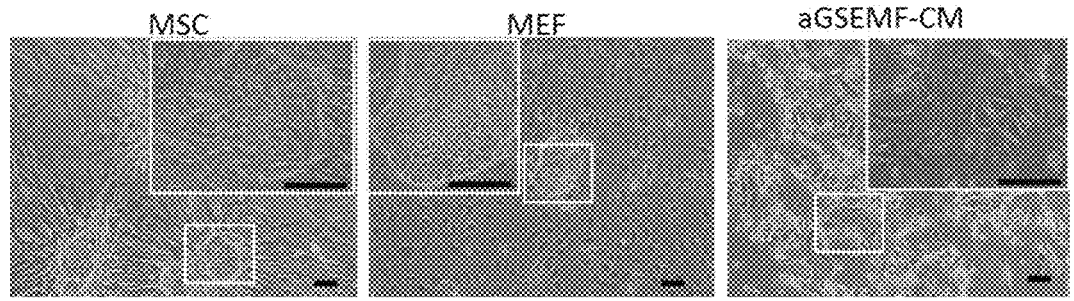
FIG. 11 shows the cell morphology map supported by MSC, MEFs and aGSEMF-CM (scale: 100 μm)

RESULTS: The conversion of human gastric epithelial cells (hGECs) to endodermal progenitor cells (hiEndoPCs) was achieved using 8 small molecule compounds (8M) and adult human gastric subepithelial myofibroblasts (aGSEMFs) in the previous experiments. Next, better trophoblast cells were determined or reprogramming without trophoblast cells was achieved. A variety of digestive tract derived stromal cells including fetal gastric subepithelial myofibroblasts (fGSEMFs), fetal intestinal subepithelial myofibroblasts (fISEMFs), fetal diaphragm stromal cells (fDCs), and other commonly used trophoblast cells such as mesenchymal stem cells (MSCs), mouse embryonic fibroblasts (MEFs), adult human skin fibroblasts (HFFs), and the like, were used, also a variety of extracellular matrices such as Matrigel gel, gelatin, and the like, as well as conditioned media derived from fetal intestinal subepithelial myofibroblasts (fISEMFs) and adult human gastric subepithelial myofibroblasts (aGSEMFs) were tested, to compare for reprogramming, respectively. Under the condition of 8M reprogramming medium, it was found that fISEMFs, fGSEMFs, aGSEMFs and the like digestive tract stromal cells and diaphragm stromal cells could successfully support hGECs to produce hiEndoPCs, and the reprogramming efficiency of fetal intestinal subepithelial myofibroblasts (fISEMFs) was the highest. Other supporting media such as MEFs, HFFs, MSCs, Matrigel, gelatin, and conditioned media and the like had little or no reprogramming support (see FIG. 10). The use of MSCs or MEFs as supporting cells produced a small amount of atypical epithelial-like cell clones. In the conditional medium derived from adult human gastric subepithelial myofibroblasts (aGSEMFs) (aGSEMFs-CM), the cells were continuously apoptotic as the culture time prolonged (as shown in FIG. 11, the picture in the upper right or upper left was an enlarged figure for the small box). Due to the limited source of fetal tissue, specimens in human gastric operation in clinically were the most readily available and sufficient adult human gastric subepithelial myofibroblasts (aGSEMFs) could be obtained, and aGSEMFs could maintain high reprogramming efficiency, and thus aGSEMFs were a good class of the reprogramming trophoblast cells, which would be reprogrammed in the subsequent experiments as trophoblast cells.

(3) Optimization of Small Molecule Combination—Screening of Necessary Small Molecules for Reprogramming 1) The trophoblast cells screened in the second part were used as the supporting cells, and the small molecules were removed one by one based on the culture conditions for above-mentioned 8 small molecule compounds (8M), and the indispensable small molecules were first screened.

2) Based on the small molecule compound combinations screened in the step 1), the small molecule compounds were successively removed one by one so that the best small molecule compound combination (with highest reprogramming efficiency) and the combination with fewest small molecule compounds (guaranteed for the formation of the clone) were finally found.

(4) Statistical Analysis

All data was obtained from 3 or more independent experiments, and the data was described as mean±standard deviation unless otherwise stated. Statistical analysis between the two groups of data was performed using the SPSS software for the two-tailed t-test. The difference between the two groups was considered statistically significant at P<0.05.

Figure 12:
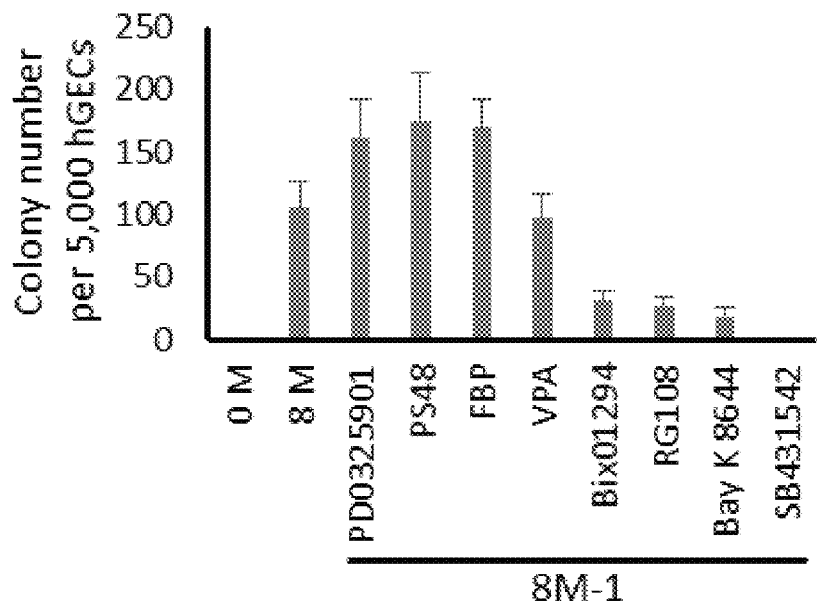
FIG. 12 is a bar graph of cloning formation efficiency subtracted one by one from 8 small molecule compounds (8M)

RESULTS: In the step (2), the most reasonable trophoblast cells-adult human gastric subepithelial myofibroblasts (aGSEMFs) were identified as the supporting cells for optimization of small molecule combinations. Based on the combination of 8 small molecule compounds (8M), the molecules were removed one by one. When PD0325901, PS48 and FBP were removed, the clonal formation efficiency increased, indicating that these small molecule compounds played a certain inhibitory role in reprogramming and should be removed; when the VPA was removed, the clonal formation efficiency did not change significantly, indicating that VPA was optional, and should be removed based on the simplification principle; however, when Bix01294, Bay K 8644, RG108 were removed, the clonal formation efficiency was obviously decreased, and especially when SB431542 was removed, clones were not produced (as shown in FIG. 12), indicating that these four small molecules were necessary.

Figure 13:
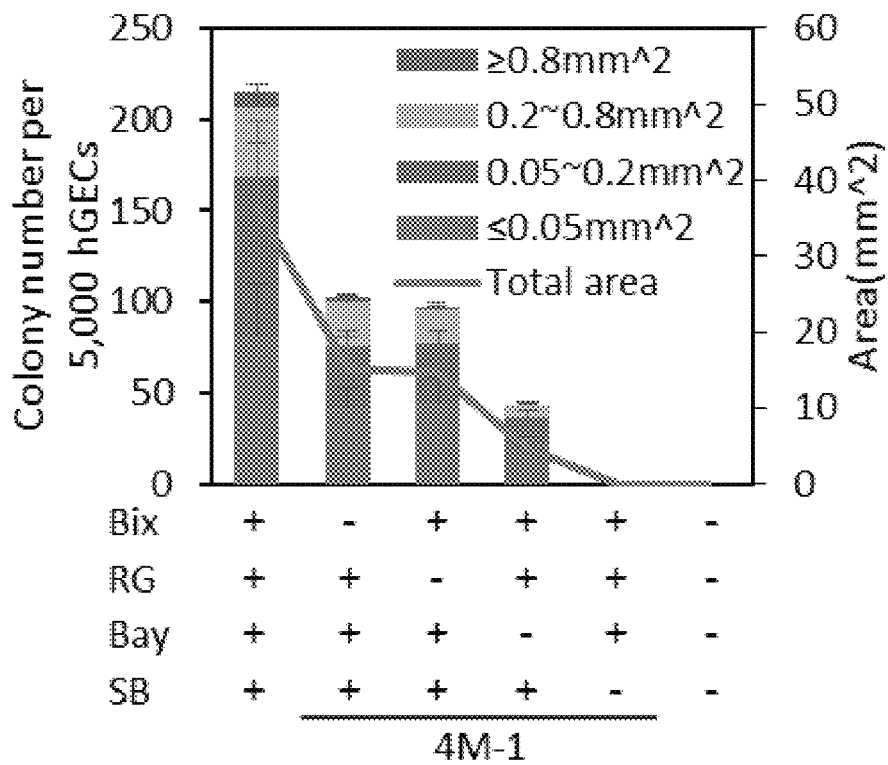
FIG. 13 is a bar graph of cloning formation efficiency subtracted one by one from four small molecule compounds of Bix01294 (Bix), Bay K 8644 (Bay), RG108 (RG) and SB431542 (SB)
Figure 14:
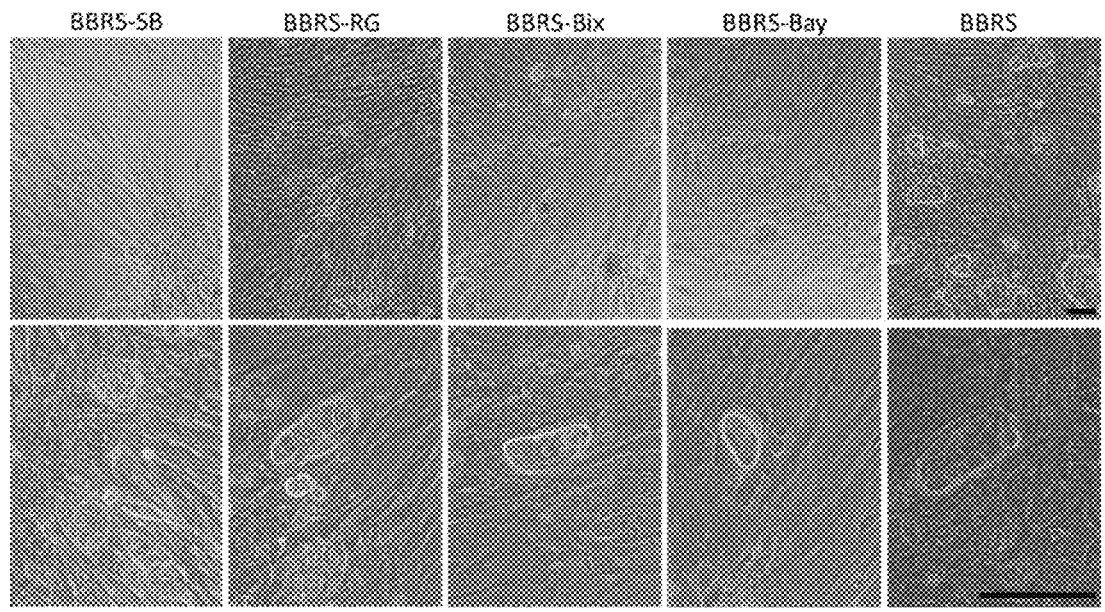
FIG. 14 is a cloning morphology map subtracted one by one from four small molecules of Bix01294 (Bix), Bay K 8644 (Bay), RG108 (RG) and SB431542 (SB) (scale: 100 μm)

Induced endodermal progenitor cells (hiEndoPCs) could also be produced based on the combination of above 4 small molecule compounds of Bix01294, Bay K 8644, RG108, SB431542 (abbreviated as BBRS combination), and the efficiency was higher than that of 8 small molecule compounds (8M). Then the optimization was performed based on Bix01294, Bay K 8644, RG108, SB431542 (BBRS combination). When removing any small molecule of Bix01294 (Bix), Bay K 8644 (Bay), RG108 (RG), the clonal formation efficiency would be significantly decreased (as shown in FIG. 13), but the morphology of the clones was not significantly different from that of the BBRS group, and no clones were formed when SB431542 (SB) was removed (as shown in FIG. 14). Therefore, it was determined that the best combination of reprogramming was the combination of Bix01294, Bay K 8644, RG108, SB431542 (BBRS), and the efficiency of reprogramming under the condition of BBRS combination was about 4%-6% (as shown in FIG. 13).

Figure 15A:
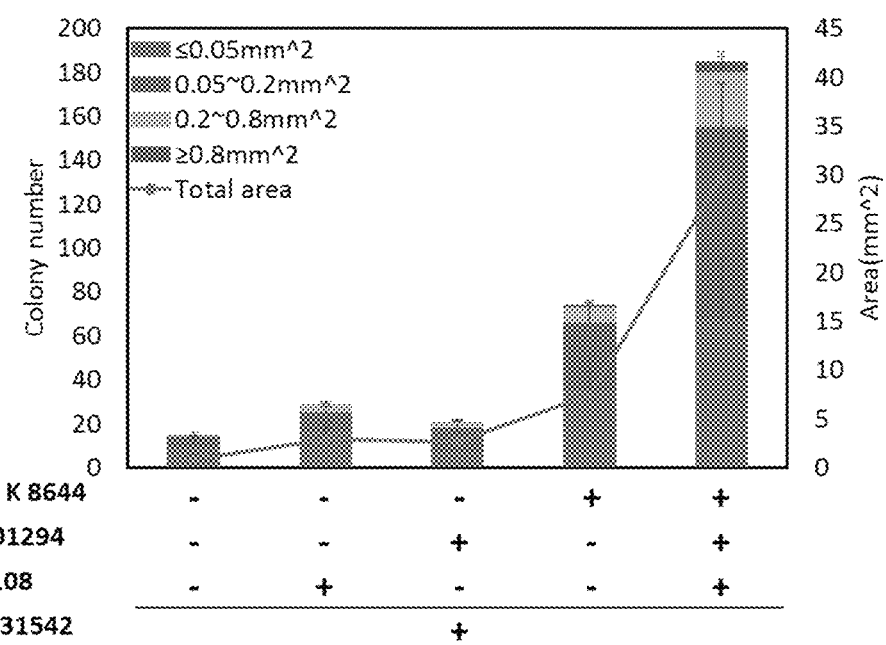
FIG. 15A is a bar graph of cloning formation efficiency based on SB431542 and in combination with other three small molecule compounds.
Figure 16:
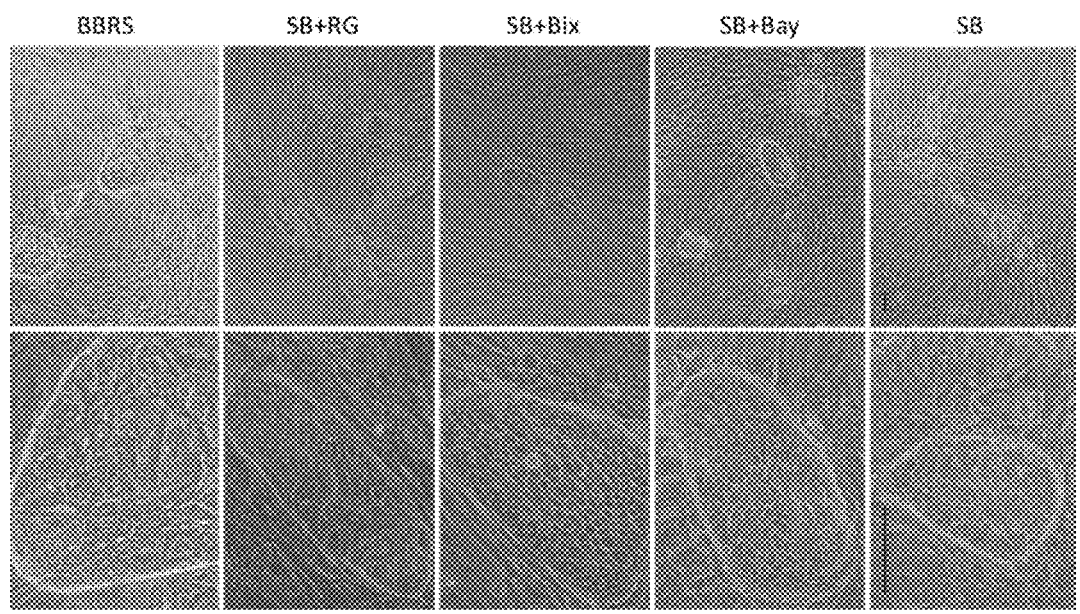
FIG. 16 is a clonal morphology map based on SB431542 and in combination with other three small molecule compounds.

Since SB431542 was the most critical, based on SB431542, combined with any of the other three small molecules (Bix01294 (Bix), Bay K 8644 (Bay), RG108 (RG)), it was found that SB431542 was capable for forming the clones with the composition of fewest small molecules, although the efficient was not as good as the optimal combination of BBRS (as shown in FIG. 15A), the morphology showed no significant differences (as shown in FIG. 16). The indispensable role of SB431542 played an important role in the mechanism of action of small molecule compounds during reprogramming.

(5) Optimization of Small Molecule Compounds Necessary for Reprogramming

Figure 15B:
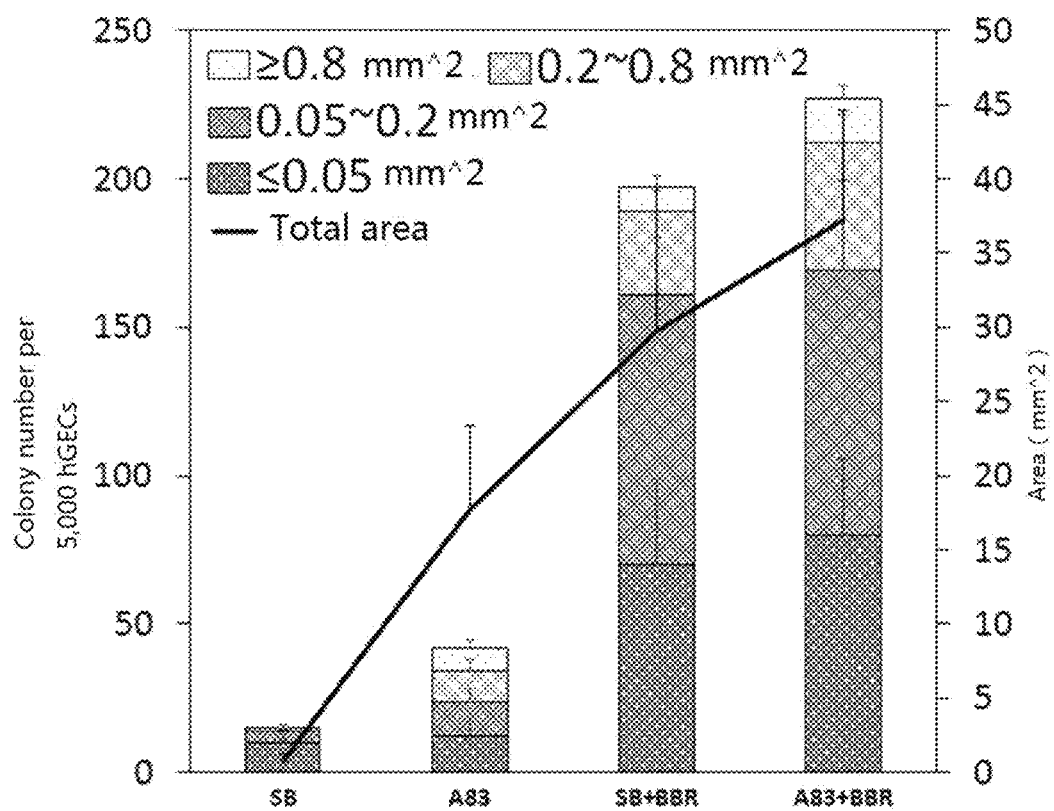
FIG. 15B is a bar graph of cloning formation efficiency based on A83-01 and in combination with other three small molecule compounds.

After confirming that SB431542 (SB) was the fewest combination of small molecule compounds capable of reprogramming in the reprogramming system, since SB431542 was an inhibitor of TGF-β signaling pathway, the inventors attempted to replace SB by using another inhibitor, A83-01 (A83), of TGF-β signaling pathway, to repeat the optimization experiment of small molecule compound combination, the results showed that A83 (concentration used of 0.5 μM) could produce similar or better effects of reprogramming either alone or in combination with other small molecules (referred to as BBRA). The results were shown in FIG. 15B, in which BBR represented the other three small molecules of Bix01294 (B), Bay K 8644 (B), RG108 (R), respectively.

Figure 17:
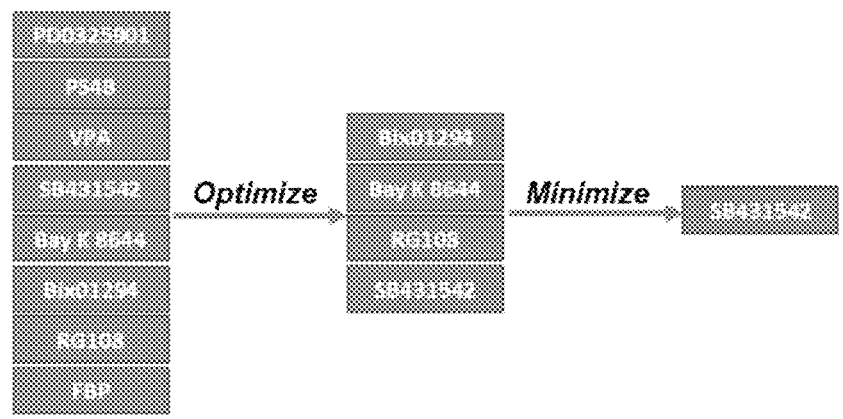
FIG. 17 is a flow chart of a small molecule compound optimization process.

In the third part, through the screening of trophoblast cells, it was determined that a variety of digestive tract derived subepithelial myofibroblasts could support the conversion of human gastric epithelial cells (hGECs) to endodermal progenitor cells (hiEndoPCs), especially, fetal derived stromal cells had stronger supporting roles, suggesting a unique supporting roles of trophoblast cells associated with the digestive tract for reprogramming of endodermal progenitor cells. Adult human gastric subepithelial myofibroblasts (aGSEMFs) were determined to be trophoblast cells in view of sufficient cellular sources. On the basis of aGSEMFs as the supporting cells, the best small molecule combinations for reprogramming, Bix01294, Bay K 8644, RG108, SB431542 (BBRS) or Bix01294, Bay K 8644, RG108, A83-01 (BBRA), and the necessary small molecule SB431542 or A83-01 (A83) were screened by three rounds of optimization for small molecules. The screening process was shown in FIG. 17. In the following Example 3, the inventors described in detail for reprogramming of human gastric epithelial cells (hGECs) to endodermal progenitor cells (hiEndoPCs) using BBRS+aGSEMFs as a condition of reprogramming as an example.

IV. Precise Positioning of Initiating Cells for Reprogramming

Materials and Methods (I) Experimental Materials (1) Experimental Cells, Tissues Human gastric epithelial cells (hGECs), adult human gastric subepithelial myofibroblasts (aGSEMFs), adult human gastric antrum tissue (provided by the General Hospital of the People's Liberation Army).

(2) Experimental Equipment

Flow cytometry (BD), Laser confocal microscope (Zeiss), inverted phase contrast microscope (Leica).

(3) Main Reagents

Basic reagents: Advanced DMEM/F-12 medium, NEAA (non-essential amino acid), Glutamine (Glutamax) were purchased from Gibco Company; penicillin-streptomycin, Accutase, mitomycin-C were purchased from Sigma Company; TryPLE digestive enzyme was purchased from Invitrogen Company.

Small molecule compounds: SB431542, Bix01294, RG108, Bay K 8644 were all purchased from Stemgent Company.

Antibodies: CD56-PE (eBioscience), Rabbit anti-human CD56 (NCAM) (Abcam), murine anti-human IgG1 MUC5AC (Abcam); Alexa Fluor® 647 Goat Anti-Mouse IgG2b (γ2b), Alexa Fluor® 568 Goat Anti-Mouse IgG1 (γ1) were all purchased from Invitrogen Company.

(2) Experimental Methods and Results (1) Fluorescence In Situ Hybridization (FISH)—Initial Location of the Initiating Cells The specific method included the following steps of:

1) The reprogramming was performed by inoculating male-derived gastric epithelial cells into female-derived trophoblast cells, or vice versa.

2) After successfully reprogramming, the cells in the original wells were fixed with a mixture of methanol and glacial acetic acid (3:1) for 20 minutes, and in situ hybridization for X and Y chromosomes was performed after sending to the Company.

3) The treated cells were observed under confocal microscopy for staining of sex chromosomes in hiEndoPCs and trophoblast cells, respectively.

Figures 18A, 18B:
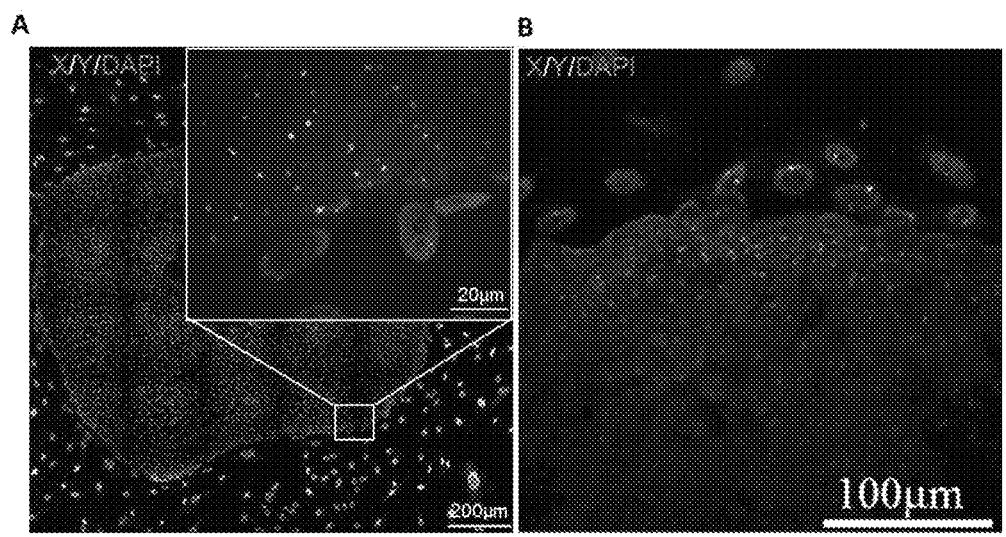
FIGS. 18A-18B are preliminary mapping staining of the initiating cells by fluorescence in situ hybridization (FISH) (A: FISH staining after reprogramming of male-derived hGECs; B: FISH staining after reprogramming of female-derived hGECs)

RESULTS: Since the two types of cells, initiating cells—human gastric epithelial cells (hGECs) and trophoblast cells—adult human gastric subepithelial myofibroblasts (aGSEMFs), involved in the reprogramming system, it has been confirmed that they alone could not be reprogrammed to induced endodermal progenitor cells (hiEndoPCs), and the reprogramming could be successful only in combination of the both above in the culture of BBRS reprogramming medium. To order to further confirm that hiEndoPCs were indeed derived from gastric epithelial cells rather than trophoblast cells, a gender mismatch combined with fluorescence in situ hybridization (FISH) experiments were performed: the reprogramming was performed using male-derived hGECs as initiating cells and female-derived gastrointestinal subepithelial myofibroblasts (aGSEMFs) as trophoblast cells, and the results of fluorescence in situ hybridization (FISH) showed that the hiEndoPCsX and Y chromosomes obtained by reprogramming were positive, indicating that they were indeed male sources, while trophoblast cells were only positive for X chromosome, indicating that it was a female source (FIG. 18A). When the reprogramming was performed using female-derived hGECs as initiating cells and male-derived gastrointestinal subepithelial myofibroblasts (aGSEMFs) as trophoblast cells, the results of fluorescence in situ hybridization (FISH) showed that hiEndoPCs were only positive for X chromosome, indicating that it was a female source, while X and Y chromosomes in trophoblast cells were positive, indicating that they were male sources (FIG. 18B). This experiment sufficiently demonstrated that hiEndoPCs derived from gastric epithelial cells rather than trophoblast cells.

(2) Determination of Surface Markers of Human Gastric Epithelial Cells (hGECs) as Initiating Cells—Flow Sorting, Inoculation and Reprogramming of CD56 Markers The specific method included the following steps of:

1) Human gastric epithelial cells (hGECs) were digested into single cells with Accutase (cell dissociation solution), which was centrifuged at 1000 rpm for 5 min, and the supernatant was discarded.

2) The cells were washed with PBS for 1 time.

3) The cells were resuspended in PBS and an appropriate amount of CD56-PE was added, and PE (PE, a fluorescent label dye) isotype control antibody was added for control group.

4) Placed in a shaker at 4° C. for 45 min.

5) The cells were washed with PBS for 3 times.

6) The cells were resuspended in an appropriate amount of PBS.

7) Analysis and screening was performed by flow cytometry, and CD56 positive cells and negative cells were retained, respectively (paying attention to the asepsis during the whole process).

8) CD56-positive and negative cells were inoculated in the same amount into adult human gastric subepithelial myofibroblasts (aGSEMFs) treated with mitomycin-C in advance, and the medium was changed to BBRS reprogramming medium after cell adhering overnight (12-16 hours).

Immunofluorescence staining was performed for CD56 (NCAM, a neuronal cell adhesion molecule, a surface protein expressed on the cell membrane) of gastric antrum tissue, and cellular immunofluorescence staining method was the same as that in the first part.

Figure 19:
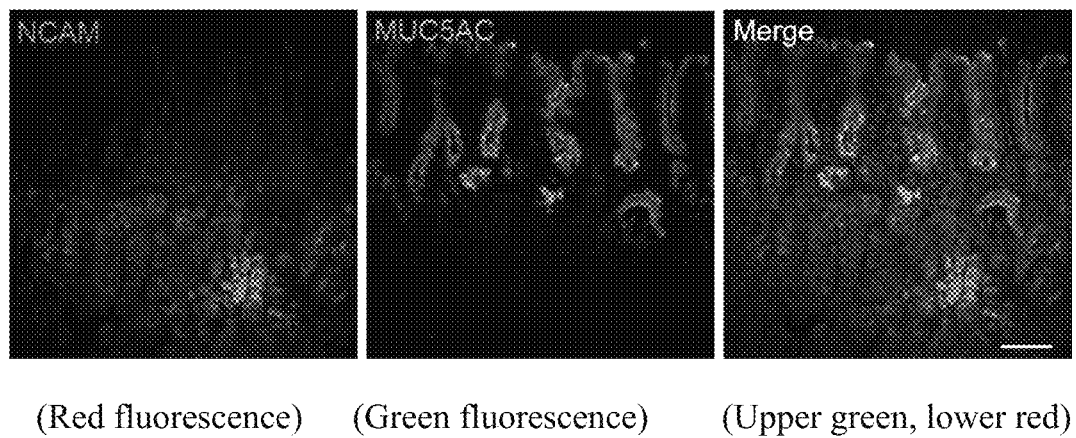
FIG. 19 is an immunofluorescence staining of CD56 (NCAM) in gastric antrum tissues (scale: 50 μm)

RESULTS: It was clearly confirmed by FISH experiments that the initiating cells were derived from gastric epithelial cells rather than trophoblast cells. Since the gastric epithelial cells belonged to the primary cells and the types of cells were mixed, the initiating cells needed to be subdivided in order to further clarify which subgroup of the initiating cells had undergone the conversion to hiEndoPCs. First, it was necessary to clarify the surface markers of hGECs. Since the isolated hGECs were mainly derived from the crypts of the gastric antrum, it had been reported that NCAM was a surface marker expressed on a variety of entoderm derived tissues, especially on primitive cells. Therefore, NCAM in situ staining of gastric antrum tissue revealed that NCAM (CD56) was mainly expressed on deep gastric tissue (ie, crypt part) in different degrees (as shown by the red fluorescence in the left part of FIG. 19), and it was hardly expressed on superficial gastric tissue. The superficial tissue mainly expressed MUC5AC (as shown in the middle of FIG. 19 with green fluorescence, and the right in FIG. 19 was the combined figure for NCAM staining and MUC5AC staining). Therefore, it was considered that NCAM could be used as a reliable marker for grouping for initiating cells.

Figure 20:
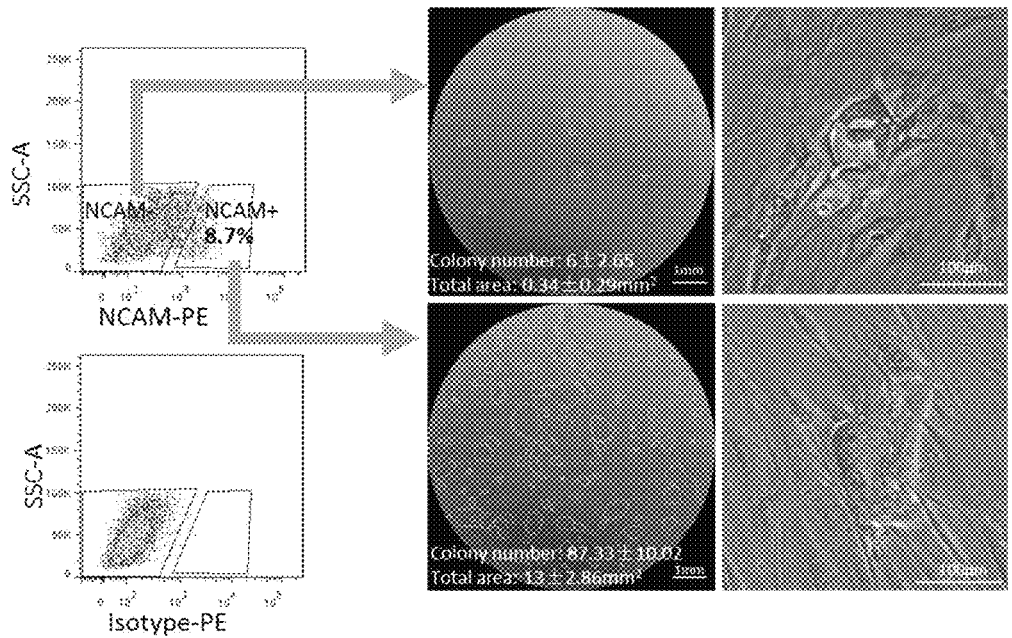
FIG. 20 is a schematic diagram showing the NCAM flow sorting of the initiating cells-human gastric epithelial cells (hGECs) and the reprogramming of the corresponding subpopulations (the lines outline the outlines of different clones)

Cultured hGECs were flow-classified using NCAM as a sorting marker and divided into two groups of NCAM positive and NCAM negative cells. Then the reprogramming was performed using NCAM positive cells and negative cells as initiating cells, respectively. The results showed that NCAM positive cells as initiating cells were reprogrammed successful, while negative cells were almost impossible (as shown in FIG. 20).

In the fourth part, it was confirmed by sex mismatch experiments that initiating cells were derived from gastric epithelial cells rather than trophoblast cells. By subclassing the initiating cells, it was further confirmed that NCAM positive, rather than NCAM negative, gastric epithelial cells underwent conversion of cell types during reprogramming, thereby achieving precise localization of initiating cells.

Example 2. Phenotypic Identification and Differentiation Potential of Induced Endodermal Progenitor Cells Endoderm progenitor cells were thought to be the origin of liver, pancreas, intestine, stomach, lung, thyroid and other internal organs, and had the potential to proliferate, thus was the ideal seed cells for obtaining functional hepatocytes, pancreatic cells, intestinal cells, lungs and thyroid cells. Previous studies have been reported to obtain endodermal progenitor cells from embryonic stem cells (ESCs) or induced Pluripotent Stem Cells (iPSCs), which lay a good foundation for the identification of reprogrammed endodermal progenitor cells in this example. In the Example 1, we successfully generated endodermal stem/progenitor-like clones (hiEndoPCs) from human gastric epithelial cells (hGECs) using a combination of BBRS and adult gastric subepithelial myofibroblasts (aGSEMFs). However, this was only a preliminary morphological change, and the properties of endodermal progenitor cells need to be further confirmed. Therefore, PCR, immunoprotein staining used to identify the characteristic marker of hiEndoPCs, and the whole genome expression detected by gene chip, the epigenetic analysis by methylation chip, its expansion potential and the microstructure observed by electron microscopy were all performed. In addition, the potentials of hiEndoPCs for differentiation into liver, pancreas, intestine, lung and thyroid were tested to confirm that hiEndoPCs were indeed endodermal progenitors and to identify the unique properties of hiEndoPCs cells.

I. Expression of the Marker Genes in Induced Endodermal Progenitor Cells

Materials and Methods (I) Experimental Materials (1) Experimental Cells

Adult human gastric subepithelial myofibroblasts (aGSEMFs), human gastric epithelial cells (hGECs), induced endodermal progenitor cells (hiEndoPCs), and H9 human embryonic stem cells (ESCs) were purchased from Wicell Company.

(2) Experimental Equipment

Real-time fluorescence quantitative PCR instrument (Bio-Rad), ordinary PCR instrument (Eppendorf), inverted phase contrast microscope (Leica), real-time quantitative 96-well plate and blocking membrane (Bio-Rad), 12-well plate, laser confocal fluorescence microscope (Zeiss), small dishs for cellular immunoconfocus (NEST).

(3) Main Reagents

Antibodies were the same as that in the first part of Example 1, the immunohistochemistry kit (Vector Lab), RA and LDN193189 were purchased from Sigma Company; A83-01 was purchased from Stemgent Company; b-FGF, Wnt3a, ActivinA, FGF10 were purchased from R&D Company.

(4) Primer Sequence

TABLE 5

Primer sequence

| Name of gene | Primer sequence (F: 5' -> 3') | Primer sequence (R: 5' -> 3') |
| --- | --- | --- |
| GAPDH | GAGTCAACGGATTTGG TCGT (SEQ ID NO: 1) | TTGATTTTGGAGGGA TCTCG (SEQ ID NO: 2) |
| FOXA2 | GCGACCCCAAGACCTA CAG (SEQ ID NO: 3) | GGTTCTGCCGGTAGA AGGG (SEQ ID NO: 4) |
| GATA4 | CCCAGACGTTCTCAGT CAGTG (SEQ ID NO: 5) | GCTGTTCCAAGAGTC CTGCT (SEQ ID NO: 6) |
| ONECUT2 | CGATCTTTGCGCAGAG GGTGCTGT (SEQ ID NO: 7) | TTTGCACGCTGCCAG GCGTAAG (SEQ ID NO: 8) |
| HNF1B | TGTACGCACACAAGCA GGAA (SEQ ID NO: 9) | GTTGGTGAGTGTACT GATGCTG (SEQ ID NO: 10) |
| HOXA3 | AGCAGCTCCAGCTCAG GCGAAA (SEQ ID NO: 11) | TGGCGCTCAGTGAGG TTCAG (SEQ ID NO: 12) |
| NANOG | ACAACTGGCCGAAGAA TAGCA (SEQ ID NO: 13) | GGAGGAAGCTGACAA CAATGAAA (SEQ ID NO: 14) |
| SOX9 | AGCGAACGCACATCAA GAC (SEQ ID NO: 15) | GCTGTAGTGTGGGAG GTTGAA (SEQ ID NO: 16) |
| OCT4 | CTTGAATCCCGAATGG AAAGGG (SEQ ID NO: 17) | GTGTATATCCCAGGG TGATCCTC (SEQ ID NO: 18) |

TABLE 5-continued

Primer sequence

| Name of gene | Primer sequence (F: 5' -> 3') | Primer sequence (R: 5' -> 3') |
| --- | --- | --- |
| SOX2 | TACAGCATGTCCTACT CGCAG (SEQ ID NO: 19) | GAGGAAGAGGTAACC ACAGGG (SEQ ID NO: 20) |
| C-MYC | TCGGAAGGACTATCCT GCTG (SEQ ID NO: 21) | GTGTGTTCGCCTCTT GACATT (SEQ ID NO: 22) |
| PDX1 | TTAGGATGTGGACGTA ATT (SEQ ID NO: 23) | GGTCAAGTTCAACAT GACAG (SEQ ID NO: 24) |
| GAST | ATGCAGCGACTATGTG TGTATG (SEQ ID NO: 25) | GCCCCTGTACCTAAG GGTG (SEQ ID NO: 26) |
| GIF | ACTCATGGAGAACTCG GTGAC (SEQ ID NO: 27) | GGGCCTTCAAGTTGT AGGCTC (SEQ ID NO: 28) |
| PGC | AGTCTATCCGTGAGAC CATGAA (SEQ ID NO: 29) | GCGGTACTTCCAAGC AGGA (SEQ ID NO: 30) |

(2) Experimental Methods and Results (1) Analysis of the Expression of Characteristic Protein in Induced Endodermal Progenitor Cells (hiEndoPCs)

The protein immunofluorescence staining method was the same as that in Example 1.

(2) Analysis of the Expression of Specific Genes in Induced Endodermal Progenitor Cells (hiEndoPCs)

The RNA of reprogrammed clones was extracted, reverse transcribed and real-time fluorescence quantitative PCR was performed, and the specific method included the following steps of:

1) The cell clones produced by reprogramming were manually picked, trying to avoid the incorporation of trophoblast cells, and then using the RNA extraction kit (purchased from QIAGEN), the appropriate lysate Buffer RLT was added to the picked cells according to the instructions, and the cells were fully lysed. And RNA was continued to be extracted according to the following steps:

2) An equal volume of 70% (V/V) ethanol was added to the lysate and mixed by pipetting.

3) The mixed solution including the precipitate was added to a spincolumn (spin column, purchased from QIAGEN) and placed in a 2 mL of collection tube, centrifuged at 12000 rpm for 30 s, and the filtrate was discarded.

4) 700 µL of Buffer RW1 (provided by RNA extraction kit, purchased from QIAGEN) was added to the spincolumn, centrifuged at 12000 rpm for 30 s, and the filtrate was discarded.

5) 500 µL of Buffer RPE (provided by RNA extraction kit, purchased from QIAGEN) was added to the spincolumn, centrifuged at 12000 rpm for 30 s, and the filtrate was discarded.

6) 500 µL of Buffer RPE was added to the spincolumn, centrifuged at 12000 rpm for 2 min, the filtrate was discarded, and then the spincolumn was vacated for 1 min.

7) The spincolumn was moved to a new 1.5 mL of collection tube, 30 µL RNeasy-free water (ribonuclease-free water) was added to the center of the membrane of the spincolumn, the spincolumn was centrifuged at 12000 rpm for 1 min, the spin column was discarded, and the extracted RNA solution was obtained in the collecting tube.

8) The concentration of the eluted RNA sample was determined using a spectrophotometer.

9), The corresponding volume of RNA was taken according to the total amount of RNA of 1 g, and RNA-free water (ribonuclease-free water) was add until 16 μL, heated at 65° C. for 5 min, then quickly transferred the centrifuge tube to ice and ice bath was performed for 2 minutes.

10) After finishing the ice bath, 4 μL of 5×RT reverse transcription reagent in the RNA reverse transcription kit was added, and the ordinary PCR instrument was used with the reverse transcription program of: 37° C. for 15 minutes, 50° C. for 5 minutes, 98° C. for 5 minutes, and 4° C. for termination.

11) The primers for detection was added to the 96-well plate in advance, and the cDNA obtained by reverse transcription, three distilled water, SYBR were absorbed as needed. After preparing the system (specifically: 9 μL of cDNA and water in total, 10 μL of SYBR, 1 μL of the primer), the wells in the plate was blocked, and the plate was placed in a real-time fluorescence quantitative PCR instrument. Procedure: 95° C. for 3 minutes, 95° C. for 10 seconds, 60° C. for 35 seconds, 65° C. for 5 seconds, 95° C. for 5 seconds, for 45 cycles in total.

(3) Directed Induction and Differentiation of Embryonic Stem Cells (ESCs) to Figurate Endoderm (DE)

Human embryonic stem cell H9, which is in good growth state, was seeded in a suitable density in a Matrigel gel-coated well plate in advance, and the medium was changed to DE induction medium: Advanced RPMI 1640+1% (W/V) B27 (serum-free nerve cell additive)+ActivinA (100 ng/mL)+CHIR99021 (3 μM, purchased from Stemgent) on the next day and cultured for 1 day, and the medium was changed to: Advanced RPMI 1640+1% B27+Activin A (100 ng/mL) on day 2 and day 3.

(4) Directed Induced Differentiation of Embryonic Stem Cells (ESCs) to Primitive Gut (PGT)

After induction to figurate endoderm (DE), the medium was changed to PGT induction medium: Advanced RPMI 1640+2% (V/V) FBS+50 ng/mL of FGF10 (fibrogenic growth factor 10)+cyclopamine (0.25 μM), and PGT was obtained in 3 days.

(5) Directed Induced Differentiation of Embryonic Stem Cells (ESCs) to the Posterior Segment of the Anterior Intestine (PFG)

After induction to figurate endoderm (DE), the medium was changed to PFG induction medium: Advanced RPMI 1640+RA (retinoic acid, 2 μM)+LDN 193189 (0.25 μM, purchased from Sigma), and PFG was obtained in 3 days.

(III) Statistical Analysis

All data was obtained from 3 or more independent experiments, and the data was described as mean±standard deviation unless otherwise stated. Statistical analysis between the two groups of data was performed using the SPSS software for the two-tailed t-test. The difference between the two groups was considered statistically significant at P<0.05.

Results:

(1) Analysis of the Expression of Characteristic Protein in Induced Endodermal Progenitor Cells (hiEndoPCs)

Figure 21:
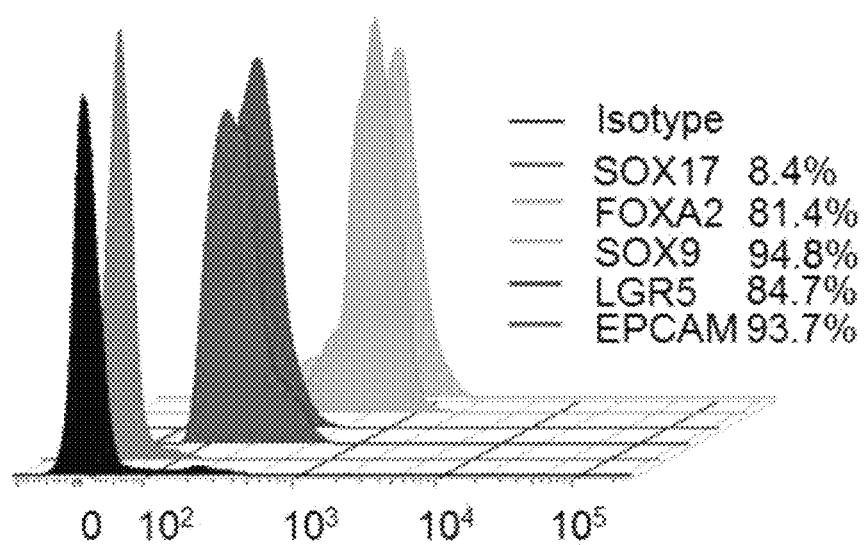
FIG. 21 is a flow level detection map of endodermal progenitor cell-specific proteins in induced endodermal progenitor cells (hiEndoPCs)
Figure 22:
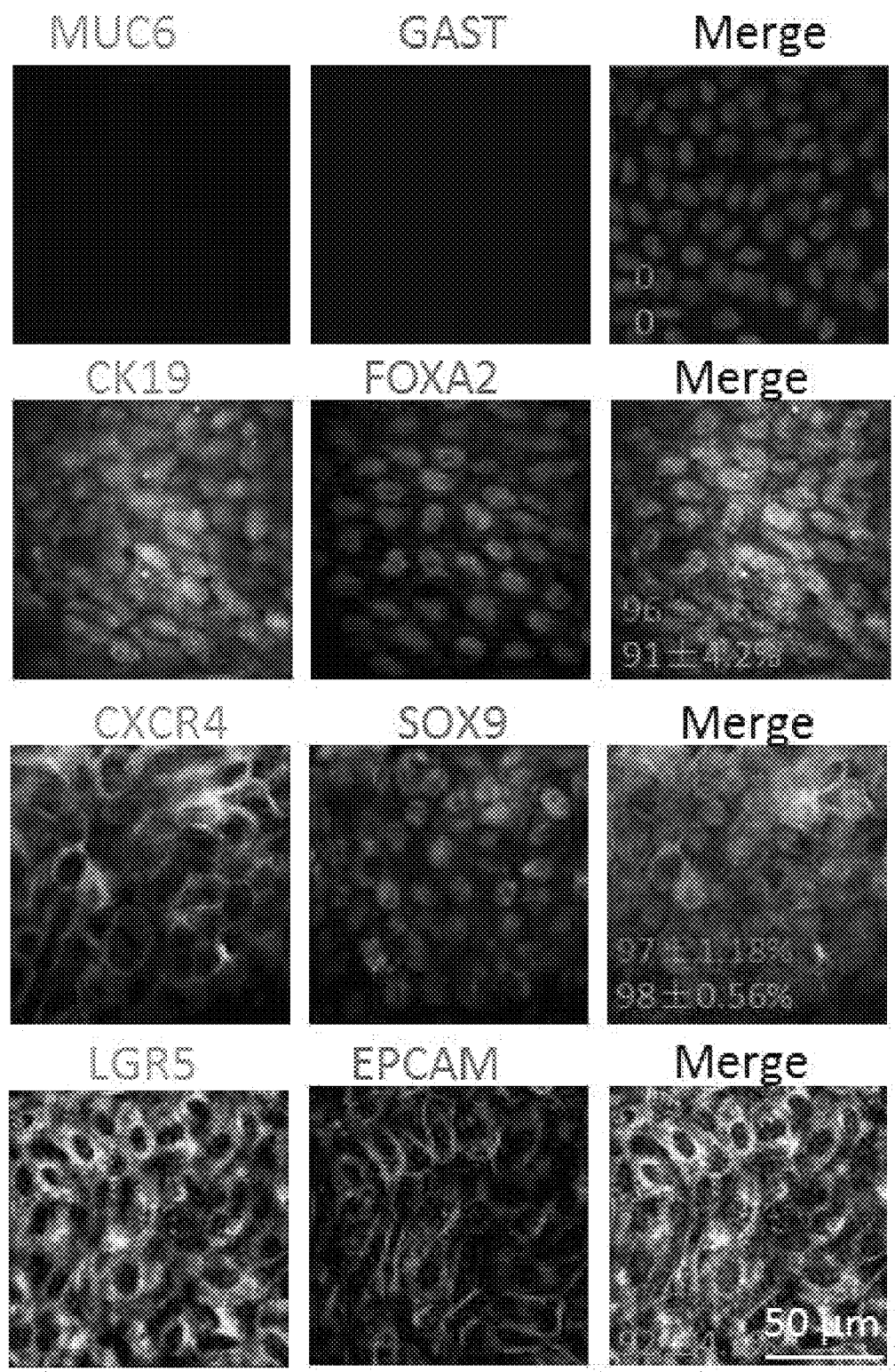
FIG. 22 is a staining diagram showing the expression of gastric-specific and endodermal progenitor-specific protein expression in induced endodermal progenitor cells (hiEndoPCs)

Analysis of endodermal specific proteins in reprogrammed clones by flow cytometry revealed that hiEndoPCs homologously highly expressed FOXA2 (Forkhead coding box protein A2), SOX9 (Sex determination region Y gene 9), SOX17 (Sex determination region Y gene 17), LGR5 (Repeated leucine-rich G-protein coupled receptor 5), EPCAM (Epithelial cell adhesion molecule), as shown in FIG. 21 (Isotype is an isotype). Immunofluorescence staining of hiEndoPCs revealed that, as shown in FIG. 22, hiEndoPCs no longer expressed the gastric specific markers, MUC6 (Mucosal protein-6) and GAST (gastrin), lost the properties of the stomach, and began to express the endodermal stem/progenitor cells specific transcription factor FOXA2 (red fluorescence, with an expression level of 96±2.6%), SOX9 (red fluorescence, with an expression level of 97±1.18%) and other endodermal stem/progenitor cells related markers such as CXCR4 (green fluorescence, with an expression level of 98±0.56%), EPCAM (red fluorescence, with an expression level of 97±2.7%), LGR5 (green fluorescence, with an expression level of 92±4.3%), CK19 (green fluorescence, with an expression level of 91±4.2%). The detection at the flow level was consistent with the immunoprotein staining, which further confirmed the characteristics of hiEndoPCs as the endodermal progenitor cells.

(2) Analysis of the Expression of Specific Genes in Induced Endodermal Progenitor Cells (hiEndoPCs)

Figures 23A, 23B:
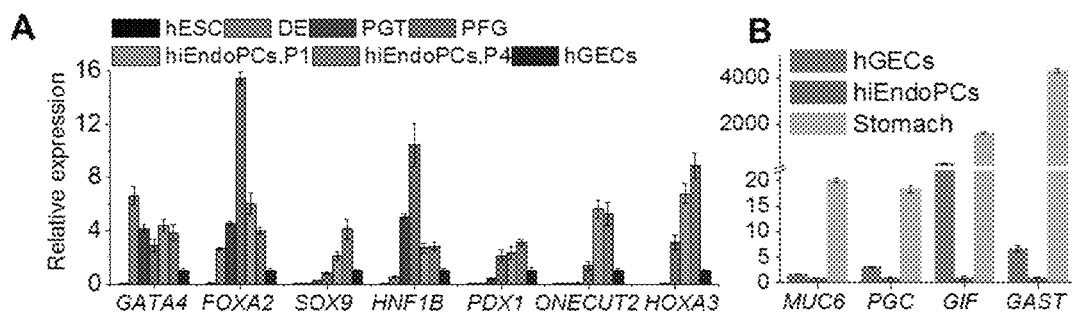
FIGS. 23A-23B are bar graphs showing the results of endodermal progenitor cell marker gene expression analysis in induced endodermal progenitor cells (hiEndoPCs), (A) and expression analysis results of gastric specific genes (B)

The results at the transcriptional level also showed that compared to human gastric epithelial cells (hGECs), the expression of the endodermal early developmental related genes in endodermal progenitor cells (hiEndoPCs) such as FOXA2 (Forkhead coding box protein A2), SOX9 (Sex determination region Y gene 9), GATA4 (GATA binding protein 4), HNF1B (hepatocyte nuclear factor homeobox protein B), PDX1 (pancreatic duodenal homeobox gene 1), ONECUT2 (one excised domain protein family 2), HOXA3 (homeobox protein A3) were significantly upregulated, even comparable to the expression of early endodermal genes in the early developmental stages of endoderm derived from embryonic stem cells (ESCs)—figurate endoderm (DE), primitive gut (PGT), and the posterior segment of the anterior intestine (PFG), and especially the most similar to the expression pattern of PFG (FIG. 23A, the column groups in FIG. 23A were successively hECs, DE, PGT, PFG, hiEndoPCs, P1, hiEndoPCs, P4 and hGECs from left to right). Moreover, hiEndoPCs no longer expressed the gastric specific markers such as MUC6, PGC, GIF, and GAST (FIG. 23B, the column groups in FIG. 23B were successively hGECs, hiEndoPCs, and human gastric tissue from left to right).

SUMMARY: Induced endodermal progenitor cells (hiEndoPCs) obtained by reprogramming of human gastric epithelial cells (hGECs) as initiating cells had lost the gastric characteristic markers such as MUC6, GIF, PGC, GAST, and the like, and began to highly express genes of markers such as transcription factors FOXA2, SOX9, HNF1B, GATA4, PDX1, HOXA3 in endodermal early progenitor cells and marker such as CXCR4, CK19, LGR5, EPCAM in other endodermal progenitor cells. Both transcript levels and protein expression levels indicated the characteristics of hiEndoPCs as endodermal progenitor cells. However, in order to fully understand the molecular characteristics, characteristics in developmental stages and spatiotemporal localization of hiEndoPCs, it was necessary to analyze the expression for whole genes or the profile for epigenetic expression.

II. Epigenetic Analysis and Localization of Developmental Stages for Induced Endodermal Progenitor Cells Materials and Methods (I) Experimental Materials (1) Experimental Cells Adult human gastric subepithelial myofibroblasts (aGSEMFs), human gastric epithelial cells (hGECs), duodenal epithelial cells (hDECs), induced endodermal progenitor cells (hiEndoPCs), figurate endoderm (DE), primitive gut (PGT), the posterior segment of the anterior intestine (PFG).

(2) Experimental Equipment

Ordinary PCR instrument (Eppendorf).

(3) Main Reagents

Illumina TotalPrep kit (Ambion), Sentrix Chip Array (Human HT-12), QIAamp DNA Micro Kit (Qiagen), EZ DNA Methylation-Gold kit (Zymo Research).

(2) Experimental Methods and Results (1) The Methods of RNA Extraction and Reverse Transcription for hGECs, hiEndoPCs, PGT, and PFG were the Same as Those in the Step I of the Present Example.

(2) Deep Sequencing Processing and Analysis (Completed with the Cooperation of the Beijing Institute of Genomics, Chinese Academy of Sciences)

The extracted hGECs, hiEndoPCs, PGT, and PFG RNA were first amplified, and the bioacylated cRNA was generated from the total RNA according to the procedure provided by the Illumina TotalPrep kit, and then the cRNA was hybridized using a Sentrix Chip Array, and the treatment after hybridization was performed according to the method provided by Illumina Company. The data was processed using Illumina BeadStudio software, and the raw data was uploaded to the Gene Expression Omnibus database (accession number GSE69706).

(3) DNA Methylation Treatment and Analysis (Completed with the Cooperation of the Beijing Institute of Genomics, Chinese Academy of Sciences)

First, DNA library construction, sequencing and data analysis were performed. hGECs from two different specimens and two corresponding monoclones of hiEndoPCs were collected, and genomic DNA was extracted with QIAamp DNA Micro Kit, sulfurous acid conversion was performed using EZ DNA Methylation-Gold kit (Zymo Research, Item No. D5005), and then sequencing was performed using a high throughput sequencing platform HiSeq 2500 (Illumina). The raw data was uploaded to the Gene Expression Omnibus database (accession number: GSE69706).

Result:

(1) Epigenetic Analysis of Whole Genomic DNA in Induced Endodermal Progenitor Cells (hiEndoPCs)

Figures 24A, 24B:
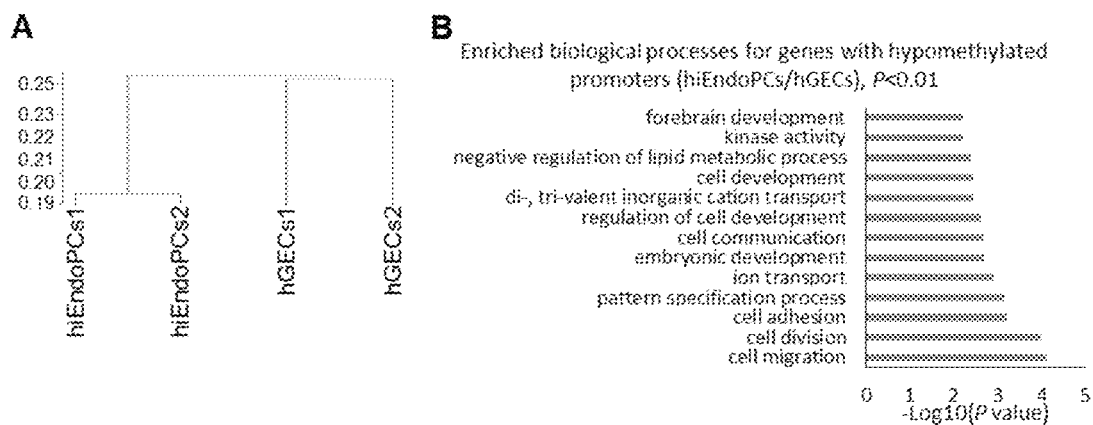
FIGS. 24A-24B show the epigenetic changes in whole genome DNA before and after reprogramming by the DNA methylation microarray (A: cluster analysis of hGECs and hiEndoPCs; B: GO analysis of hiEndoPCs compared to hGECs hypomethylated genes)

In the step I, the identification of hiEndoPCs was limited to certain characteristic markers of endodermal stem/progenitor cells. To confirm that hiEndoPCs and hGECs were indeed two different types of cells, we analyzed hiEndoPCs and hGECs from the perspective of epigenetic modification by using whole genomic DNA methylation chip detection. The results of cluster analysis showed that hiEndoPCs and hGECs had different epigenetic patterns (FIG. 24A), which clearly confirmed that the cells changed significantly after reprogramming. Gene Ontology (GO) analysis showed that the classification of genes in the hypomethylated state, i.e., the genes in active state in hiEndoPCs, were mainly related to embryonic development or stem cell development compared with hGECs (FIG. 24B). This was consistent with the early endodermal properties and the stem/progenitor cellular properties of the hiEndoPCs.

(2) Epigenetic Modification of the Promoter Region of Characteristic Genes in Induced Endodermal Progenitor Cells (hiEndoPCs)

Figures 25A, 25B:
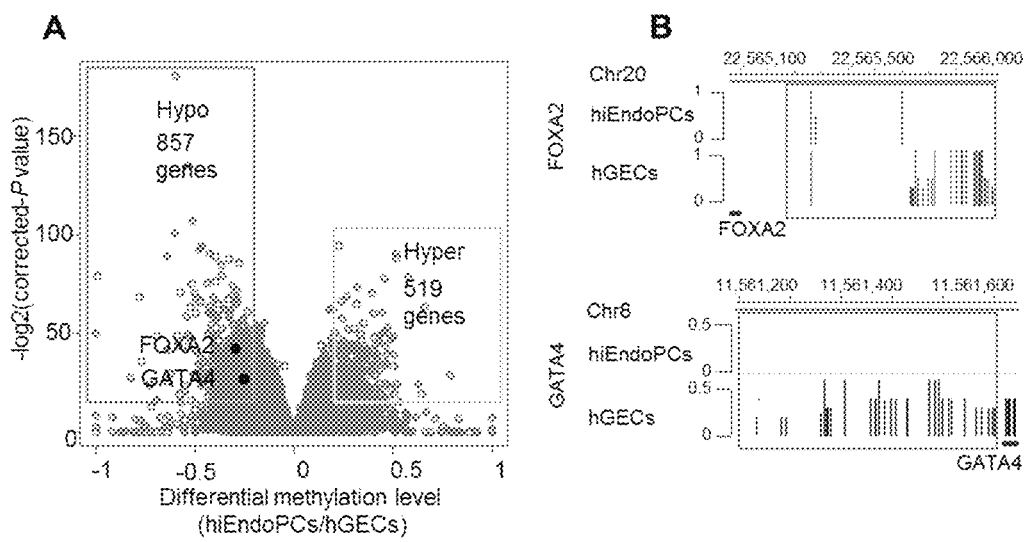
FIG. 25A is a volcano plot showing the number of genes whose promoter methylation levels change in hiEndoPCs compared to hGECs.
FIG. 25B is a comparison of methylation levels of hiEndoPCs and hGECs in the promoter regions of FOXA2 and GATA4 genes.

Methylation analysis showed that there were 519 and 857 genes for up-regulation and down-regulation of methylation in promoter region in hiEndoPCs compared to hGECs (FIG. 25A), of which methylation levels in promoter region in endodermal specific transcription factor FOXA2 (Forkhead coding box protein A2) and GATA4 (GATA binding protein 4) were significantly reduced in hiEndoPCs (FIG. 25B), indicating that the gene expression of FOXA2 and GATA4 was transcriptionally activated, which was consistent with the high expression of FOXA2 and GATA4 genes in hiEndoPCs.

(3) Localization of Developmental Stage of Induced Endodermal Progenitor Cells (hiEndoPCs)

Figure 26:
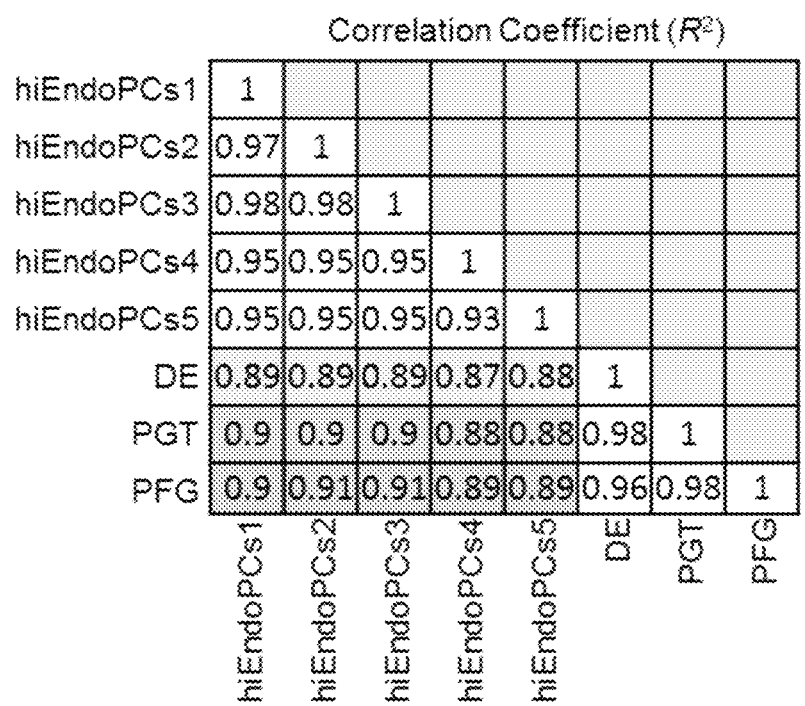
FIG. 26 is a correlation analysis of RNA deep sequencing, showing the relationship between hiEdoPs and ESC-derived DE, PGT, and PFG.
Figure 27:
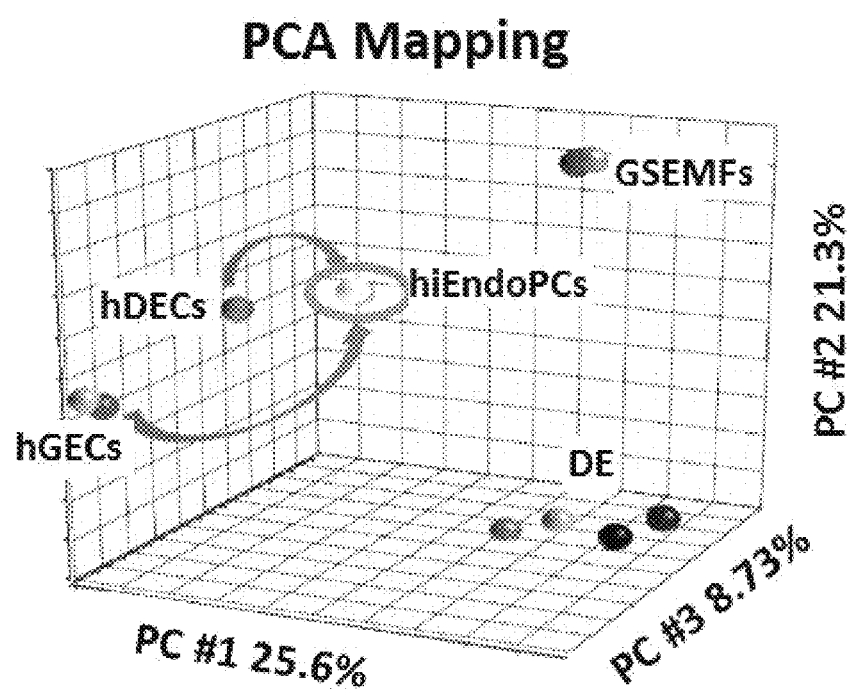
FIG. 27 is a PCA analysis plot showing the positional relationship of hGECs, hDECs, hiEndoPCs derived from hGECs, hiEndoPCs derived from hDECs, DE and GSEMFs derived from ESCs on the whole gene expression profile.

After confirming the characteristics of hiEndoPCs as the endodermal stem/progenitor cells from multiple levels, it was also necessary to locate the developmental stage of hiEndoPCs to further clarify its characteristics. Since the positive control of hiEndoPCs in the natural state was unobtainable, the well-recognized figurate endoderm (DE), primitive gut (PGT), posterior segment of the anterior intestine (PFG), and the like early endodermal stages, which were derived from the embryonic stem cells (ESCs) and induced in accordance with the developmental processes, were used as positive controls to compare the profiles of whole genomic expression with hiEndoPCs obtained by reprogramming. RNA deep sequencing revealed that hiEndoPCs were between PGT and PFG and closer to PFG (FIG. 26). In addition, PCA principal component analysis showed that hiEndoPCs derived from gastric epithelial cells and hiEndoPCs derived from duodenal epithelial cells were very similar in whole gene expression profiles (PCA principal component analysis referred to a multivariate statistical analysis method by linear transformation of multiple variables to select fewer number of important variables), which was consistent with their cellular morphology being most similar as previously found, and were different from their initiating cells, and also significantly different from ESCs derived figurate endoderm (DE), trophoblast Cells (GSEMFs) (FIG. 27).

SUMMARY: Analysis of methylation level of whole genomic DNA further confirmed that hGECs were significantly different from hiEndoPCs. After reprogramming, hiEndoPCs obtained the molecular characteristics of endodermal stem/progenitor cells, thus the conversion of hGECs to hiEndoPCs was indeed a reprogramming process. Moreover, RNA deep sequencing confirmed that hiEndoPCs were between PGT and PFG and closer to PFG at the developmental stage, thus realizing the temporal and spatial localization of hiEndoPCs.

III. Microscopic Characteristics of Induced Endodermal Progenitor Cells

Materials and Methods (I) Experimental Materials (1) Experimental Cells

Human gastric epithelial cells (hGECs), induced endodermal progenitor cells (hiEndoPCs).

(2) Experimental Equipment

H7650 transmission electron microscope (HITACHI), H7650 Electron Microscopy, AMT XR16M CCD Digital Camera (electronic coupler of digital camera, AMT), AMT Capture Engine Software Version 600.259 (capture engineering software), detachable 96-well plate (Corning).

(3) Main Reagents

Polybed 812 epoxy resin was purchased from Polysciences, Inc., Warrington, Pa., Reynolds' lead citrate (provided by National Instrument Analysis and Testing Center, Academy of Military Medical Sciences), aqueous uranyl acetate (provided by the National Instrument Analysis and Testing Center, Academy of Military Medical Sciences).

(2) Experimental Methods and Results

The specific method included the following steps of:

1. hiEndoPCs and hGECs were seeded in detachable 96-well plates.

2. The cells were washed with PBS, and fixed with fixative solution of 3% of glutaraldehyde and 0.1 M of sodium cacodylate (purchased from Sigma) at pH 7.4 overnight (12-16 hours).

3. The cells were washed with sodium cacodylate buffer (purchased from Sigma) for 3 times, and then fixed with the mixture of 1% of osmium tetroxide (purchased from Sigma) and 0.1 sodium cacodylate buffer (purchased from Sigma) for 1 hour.

4. After washing with deionized water, dehydrated and buried in Polybed 812 epoxy resin.

5. The tissue was cut into 70 nm sections, stained with 4% of aqueous uranyl acetate (provided by the National Instrument Analysis and Testing Center, Academy of Military Medical Sciences) for 15 minutes and then with Reynolds' lead citrate (by provided the National Instrument Analysis and Testing Center, Academy of Military Medical Sciences) for 7 minutes.

6. The stained sections were observed by H7650 transmission electron microscope.

7. Imaging was performed by using AMT XR16M CCD and AMT 600.259 (capture engineering software).

Figures 28A, 28B, 28C, 28D, 28E:
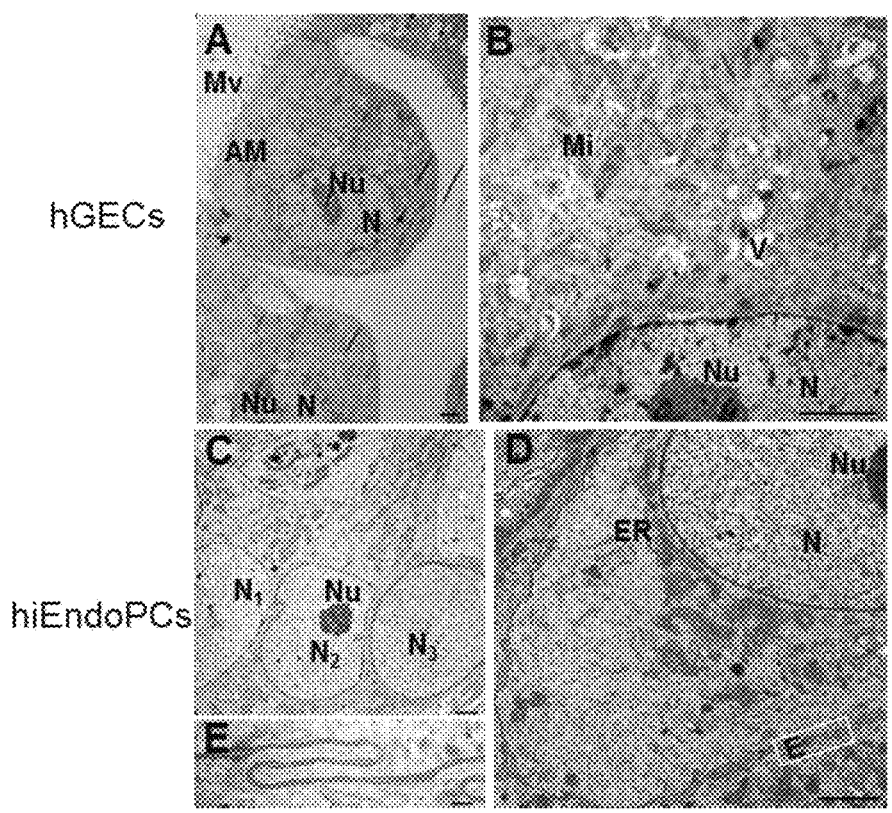
FIGS. 28A-28E are microscopic morphology maps of hGECs and hiEndoPCs, (scale: 2 μm (A-D), 100 nm (E))

RESULTS: as shown in FIGS. 28A-28E (in the figure, Microvilli (Mv), Terminal web of actin microfilaments (AM), Mitochondria (Mi), Vacuoles (V), Endoplasmic reticuLum (ER), Nucleus (N), nucleolus (Nu)), it was found from the observation of hGECs and hiEndoPCs at the level of electron microscopy that, hGECs showed the characteristics of mature cells including relatively large cells, intercellular tight junction, relatively small nucleoplasm, and many actin fiber networks (FIG. 28A), rich in cytoplasmic contents, a large amount of mitochondria contained, microvilli and vacuoles (FIG. 28B). The cells of hiEndoPCs were smaller, the junctions were tighter, the nucleoli were clearer, the nucleoplasmic ratio was larger (FIG. 28C), the cytoplasmic content was less, the mitochondria contained were less, and a small amount of mitochondria and endoplasmic reticulum were distributed around the nuclear membrane (FIG. 28D), and there were fingerlike prominent junctions of immature cells at the cellular junctions (FIG. 28E). Therefore, microscopic analysis showed that hiEndoPCs were significantly different from hGECs, and hiEndoPCs showed microscopic characteristics of stem cells, while hGECs showed characteristics of terminally differentiated mature cells.

SUMMARY: Analysis at the level of electron microscopy further confirmed that the characteristics of hiEndoPCs belonged to that of stem/progenitor cells, while hGECs had the characteristics of mature cells. The conversion of hGECs to hiEndoPCs was the conversion of mature cells to stem/progenitor cells.

4. Characteristics of Proliferation and Passage Expansion of Induced Endodermal Progenitor Cells Materials and Methods (I) Experimental materials (1) Experimental Cells Adult human gastric subepithelial myofibroblasts (aGSEMFs), induced endodermal progenitor cells (hiEndoPCs).

(2) Experimental Equipment

Inverted phase contrast microscope (Leica), MltraVIEW (Perspective, PerkinElmer).

(3) Main Reagents

Fibronectin (FN), Cell-TAK gel (CT) were purchased from BD; serum-free cell freezing medium (Bio-Tool); A83-01 (Stemgent); bFGF (basic fibroblast growth factor b), Wnt3a were all purchased from R&D; mitomycin-C (Sigma); Advanced DMEM/F12, Dispase were purchased from Gibco.

(2) Experimental Methods and Results (1) Passage of hiEndoPCs

1. Preparation before passage: aGSEMFs treated with mitomycin-C were seeded at a suitable density in the well plates in advance, or about 3 hours in advance, Fibronectin (FN), *Cell*-TAK (CT) gel were coated in the well plates and dried at room temperature;

2. Preparation of medium for passage: Advanced DMEM/DF12+AWF (Formulation: A83-01 0.5 µM+Wnt3a 50 ng/mL+bFGF 10 ng/mL), or Advanced DMEM/DF12+A (A83-01, 0.5 µM);

3. The clones were manually picked upon passage, and divided into small pieces at a ratio of about 1:3-4, and placed in FN+AWF, CT+AWF or, Trophoblast (trophoblast cells)+A medium at 37° C. in a 5% $CO_2$ incubator to subculture.

(2) Freezing and resuscitation of hiEndoPCCs 1. Freezing: the manually picked clones were digested with 5 mg/mL of Dispase enzyme for 5 minutes at 37° C., and blown into small pieces. The cells were washed twice with medium, and then the cells were resuspended with an appropriate amount of serum-free cell freezing medium, placed in a cryotube, and stored directly at −80° C.

2. Resuscitation: The frozen cells were quickly thawed at 42° C., washed with 10 volumes of medium, centrifuged, and then resuspended in Advanced DMEM/DF12+A (A83-01 0.5 µM) medium and inoculated on the above prepared trophoblast cells and cultured.

Result:

(1) Characteristics of Proliferation of hiEndoPCs During Reprogramming

Figures 29A, 29B, 29C:
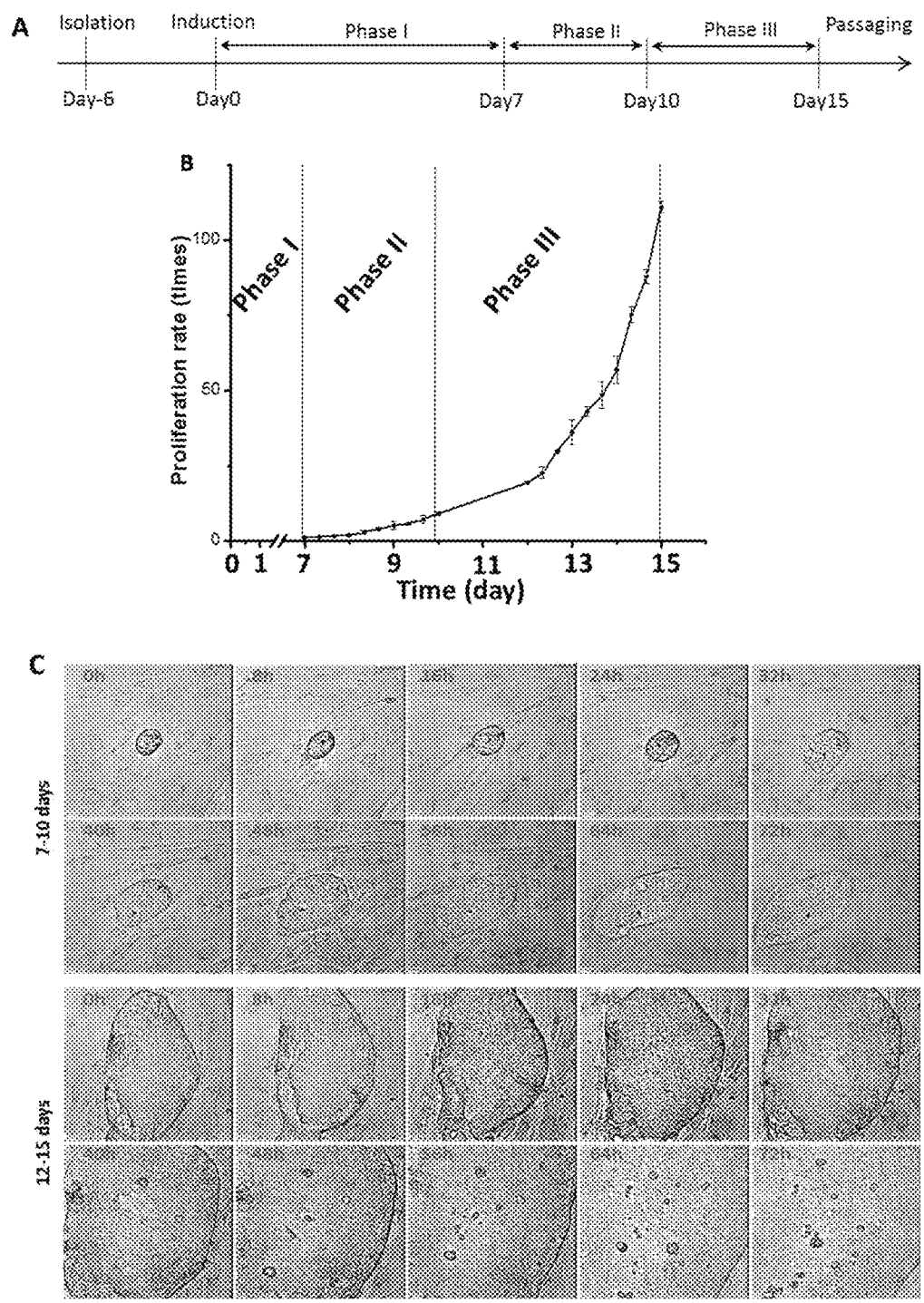
FIGS. 29A-29C show the dynamics of hiEndoPCs during reprogramming. A is the axial map of the period during the reprogramming process of hiEndoPCs, B is the growth rate curve of different periods, and C is the dynamics change map of cell morphology of Phase II and Phase III.

After confirming the molecular characteristics of hiEndoPCs as the endodermal progenitor cells, the characteristics of proliferation were analyzed. The kinetics of hiEndoPCs during reprogramming were carefully observed, and divided into three phases: some tight, sharp edges on day 0-7 were the characteristics of the gradual appearance of cell clones (Phase I); there were a process of slower proliferation for clones on day 7-10 (Phase II), with the clones growing from small to large; it was a stage of rapid proliferation for clones on day 10-15 (Phase III), with many small clones rapidly aggregating into larger clones, and the doubling time of the cells was 36.1±4.7 hours at this stage (see FIGS. 29A-29C).

(2) Screening of Subculture Conditions for hiEndoPCs

Figures 30A, 30B, 30C, 30D:
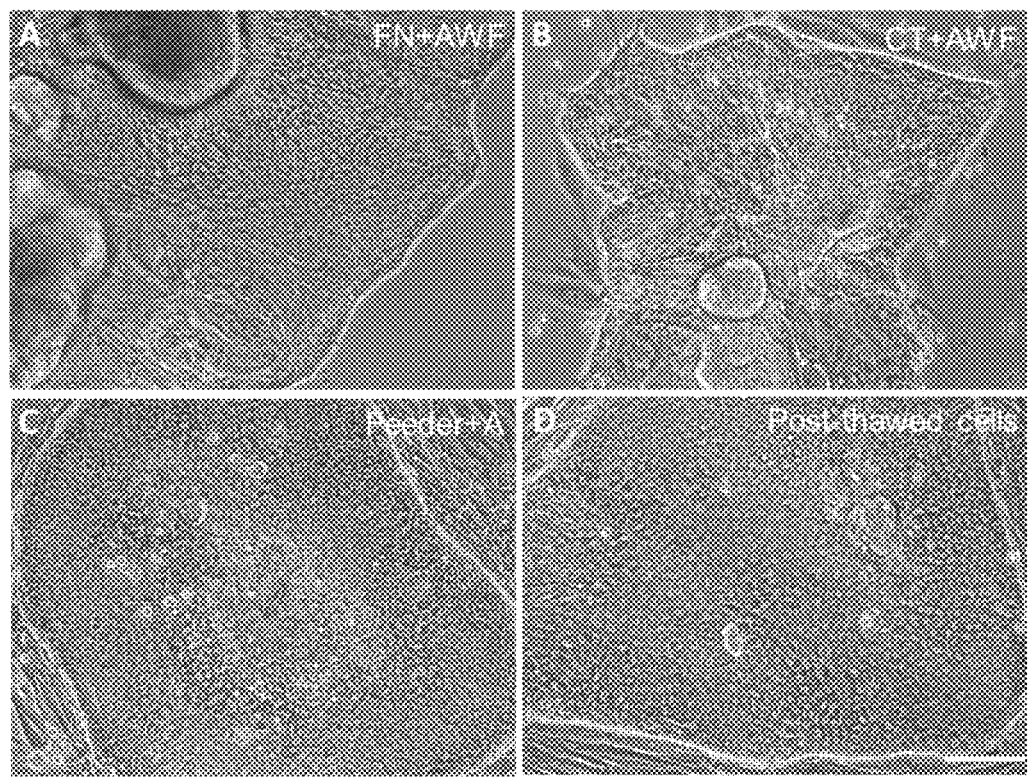
FIGS. 30A-30D are cell morphology maps of the hiEndoPCs after passage under different supporting environments (scale: 100 μm)

Since hiEndoPCs were endodermal progenitor cells, they were obliged to have certain potential for passage expansion. The inventors had repeatedly screened for passage conditions and finally determined that the clones were well grown and maintained in the state of the original clones after passage under the condition of Fibronectin (FN) gel or BD *Cell*-TAK (CT) gel as extracellular matrix in combination with Advanced DMEM/DF12+AWF (A83-01 0.5 µM+Wnt3a 50 ng/mL+bFGF 10 ng/mL), ie, FN+AWF (FIG. 30A) or CT+AWF (FIG. 30B), and the like conditions free of trophoblast cells. The original morphology of stem/progenitor cell clones was maintained under the conditions of aGSEMFs as trophoblast cells in combination with Advanced DMEM/DF12+A (A83-01 0.5 µM), ie, Trophoblast+A (FIG. 30C). hiEndoPCs could also be frozen, and the original morphology of the clones could be maintained under the condition of Trophoblast+A after resuscitation of the clones (FIG. 30D, Post-Thawed cells, resuscitated after freezing).

Figure 31:
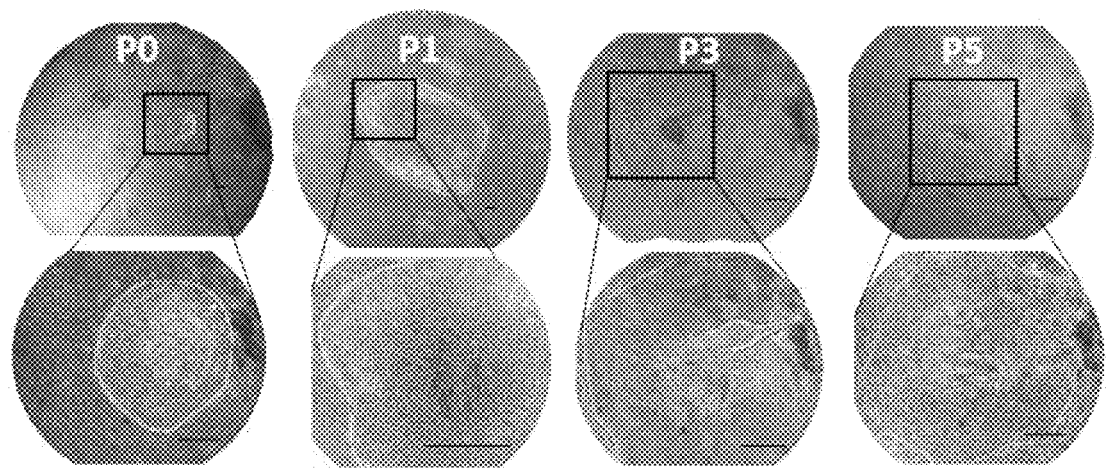
FIG. 31 is a cell morphology map of hiEndoPCs during passage (scale: 200 μm)
Figure 32:
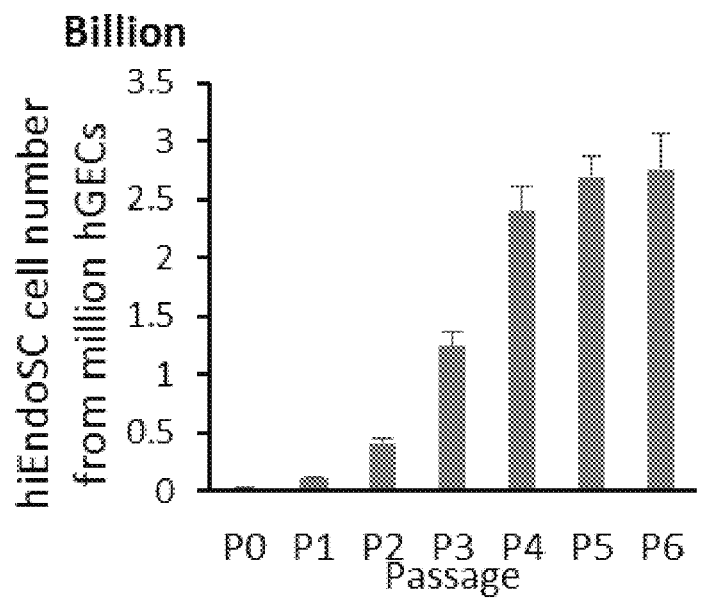
FIG. 32 is a histogram of the number of passages of hiEndoPCs and the number of cells per generation.

(3) Passage Expansion Characteristics of hiEndoPCs hiEndoPCs could be expanded for about 4-6 generations under the above subculture conditions, and the cell morphology remained basically unchanged during the passage (FIG. 31, the lower of the picture was an enlarged part of the box in the picture upper). After 4 generations, the cell proliferation rate slowed down, and the number of cells in the 6th generation peaked, indicating that its proliferation potential was limited. Approximately $10^9$ stem/progenitor cells (hiEndoPCs) were obtained initiating with approximately $10^6$ human gastric epithelial cells (hGECs) available each time, after reprogramming and approximately 4-6 amplifications (FIG. 32).

SUMMARY: hiEndoPCs could be expanded for 4-6 generations using the corresponding passage conditions.

V. Identification of Differentiation Potential of Induced Endodermal Progenitor Cells Materials and Methods (I) Experimental Materials (1) Experimental Cells Human gastric epithelial cells (hGECs), induced endodermal progenitor cells (hiEndoPCs), and H9 human embryonic stem cells (ESCs) were purchased from Wicell Company.

(2) Experimental Equipment

Real-time fluorescence quantitative PCR instrument (Bio-Rad), ordinary PCR instrument (Eppendorf), upright fluorescence microscope (Leica), real-time quantitative 96-well plate and blocking membrane (Bio-Rad), 12-well plate, laser confocal fluorescence microscope (Zeiss), inverted phase contrast microscope (Leica), small dishs for cellular immunoconfocus (NEST).

(3) Main Reagents

1. Main Antibodies

TABLE 6

Primary antibodies for immunofluorescence detection of endodermal progenitor cells (hiEndoPCs)

| Primary antibody | Company | Item No. | Genus of primary antibody | Dilution ratio |
| --- | --- | --- | --- | --- |
| AFP | Sigma | A8452 | Mouse immunoglobulin 2a | 200 |
| ALB | Abcam | ab10241 | Mouse immunoglobulin 2b | 400 |
| CK18 | Santa Cruz | sc-6259 | Mouse immunoglobulin 1 | 100 |
| Lgr5 | Sigma | HPA012530 | Rabbit | 350 |
| CDX2 | R&D | AF3665 | Goat immunoglobulin | 100 |
| Muc2 | Abcam | ab118964 | Mouse immunoglobulin 1 | 100 |
| Somatostatin | Millipore | AB5494 | Rabbit | 100 |
| InsuLin | Abcam | ab7842 | Guinea pig | 100 |
| Glucagon | Sigma | G2654 | Mouse immunoglobulin 1 | 200 |
| ProinsuLin | R&D | MAB13361 | Mouse immunoglobulin 2a | 200 |
| c-peptide | Millipore | 05-1109 | Mouse immunoglobulin 1 | 100 |
| α-amylase | Sigma | A8273 | Rabbit | 200 |
| PDX1 | Abcam | ab47308 | Guinea pig | 200 |
| NKX6.1 | R&D | AF5857 | Goat immunoglobulin | 200 |
| Villin | Abcam | ab201989 | Mouse immunoglobulin 1 | 100 |
| E-Cadherin | BD | 610181 | Mouse immunoglobulin 2a | 100 |

TABLE 7

Secondary antibodies for immunofluorescence detection of endodermal progenitor cells (hiEndoPCs)

| Secondary antibody | Company | Item No. | Dilution ratio |
|---|---|---|---|
| Alexa Fluor ® 568 Goat anti-Mouse immunoglobulin 1 (γ1) | Invitrogen | A21124 | 400 |
| Alexa Fluor ® 488 Goat anti-Mouse immunoglobulin 2a (γ2a) | Invitrogen | A21131 | 400 |
| Alexa Fluor ® 647 Goat anti-Mouse immunoglobulin 2b(γ2a) | Invitrogen | A21242 | 400 |
| Alexa Fluor ® 647 Goat anti-Mouse immunoglobulin (H + L) | Invitrogen | A21244 | 400 |
| Alexa Fluor ® 488 Goat anti-Guinea pig immunoglobulin(H + L) | Invitrogen | A11073 | 400 |
| Alexa Fluor ® 647 Goat anti-Rat immunoglobulin(H + L) | Invitrogen | A21247 | 400 |
| Alexa Fluor ® 568 Goat anti-Mouse immunoglobulin (H + L) | Invitrogen | A11031 | 400 |
| Alexa Fluor ® 647 Donkey anti-Mouse immunoglobulin (H + L) | Invitrogen | A31571 | 400 |
| Alexa Fluor ® 568 Donkey anti-Mouse immunoglobulin (H + L) | Invitrogen | A10037 | 400 |
| Alexa Fluor ® 488 Donkey anti-Mouse immunoglobulin (H + L) | Invitrogen | A-21202 | 400 |
| Alexa Fluor ® 568 Donkey anti-Goat immunoglobulin (H + L) | Invitrogen | A11057 | 400 |
| Alexa Fluor ® 488 Donkey anti-Rabbit immunoglobulin (H + L) | Invitrogen | A21206 | 400 |
| Alexa Fluor ® 4568 Goat anti-Mouse immunoglobulin 2a (γ2a) | Invitrogen | A21134 | 400 |

2. Main media, additives and matrigels: Advanced DMEM/DF12, MCDB131 (low protein, serum-free medium 131), CMRL 1066, Advanced RPMI 1640, GlutaMax (Glutamine), NEAA (non-essential amino acids), N2 (Serum-free nerve cell additive N2), B27 (serum-free nerve cell additive B27) were all purchased from Gibco; ITS-X (insulin-transferrin-selenium-ethanolamine complex solution, Life Technologies); T3, Ascorbic acid (vitamin C, Sigma); HM (hepatocyte culture medium, Sciencell); Lanminin, Fibronectin (FN), Collagen IV were purchased from BD.

3. Cytokines: b-FGF (basic fibroblast growth factor b), Wnt3a, ActivinA, FGF4 (fibroblast growth factor 4), HGF (hepatocyte growth factor), OSM (ostomalin M), FGF10 (fibrogenic growth factor 10), FGF7 (fibroblast growth factor 7), EGF (epidermal growth factor), Noggin, BMP4 (bone morphogenetic protein 4), IGF (insulin-like growth factor), TSH (thyroid stimulating hormone), InsuLin were purchased from R&D Company; NaI (sodium iodide, Sigma).

4. Small molecule compounds: DEX (dexamethasone), RA (retinoic acid), LDN193189, SANT-1 were purchased from Sigma; TPB was purchased from EMD MilliPore; ALK5 inhibitor II was purchased from Enzo Life Sciences; γ-secretase inhibitor XX was purchased from EMD MilliPore; R428 was purchased from SelleckChem; Chir99021 was purchased from Stemgent.

5. Kit: human albumin ELISA kit (human albumin assay kit, purchased from Bethyl).

6. Other reagents: 1 mg/mL of ICG (indocyanine green) solution, hematoxylin, Periodic Acid, Triton X-100, Schiff's (Polyethylene glycol octyl phenyl ether, Sigma), sodium citrate buffer, 4% of paraformaldehyde.

(4) Primer Sequences

TABLE 8

Primer sequences

| Gene name | Primer sequence (F: 5' -> 3') | Primer sequence (R: 5' -> 3') |
|---|---|---|
| HNF4A | ACGGACAGATGTGTGAGTGG (SEQ ID NO: 31) | CAGGAGCTTATAGGGCTCAGA (SEQ ID NO: 32) |
| AFP | CTTGCACACAAAAAGCCCACT (SEQ ID NO: 33) | GGGATGCCTTCTTGCTATCTCAT (SEQ ID NO: 34) |
| ALB | TTTATGCCCCGGAACTCCTTT (SEQ ID NO: 35) | ACAGGCAGGCAGCTTTATCAG (SEQ ID NO: 36) |
| TF | CCTCCTACCTTGATTGCATCAG (SEQ ID NO: 37) | TTTTGACCCATAGAACTCTGCC (SEQ ID NO: 38) |
| AAT | ATGCTGCCCAGAAGACAGATA (SEQ ID NO: 39) | TTGTTGAAGGTTGGGTGATCC (SEQ ID NO: 40) |
| GGT | GGGGAGATCGAGGGCTATGAG (SEQ ID NO: 41) | GATGACGGTCCGCTTGTTTC (SEQ ID NO: 42) |
| G6PC | TCAGGGAAAGATAAAGCCGACC (SEQ ID NO: 43) | AGGTAGATTCGTGACAGACAGAC (SEQ ID NO: 44) |
| CYP1A2 | ATGGCATTGTCCCAGTCTGTT (SEQ ID NO: 45) | TGGCTCTGGTGGACTTTTCAG (SEQ ID NO: 46) |
| CYP3A4 | AAGTCGCCTCGAAGATACACA (SEQ ID NO: 47) | AAGGAGAGAACACTGCTCGTG (SEQ ID NO: 48) |
| CYP3A7 | AAGGTCGCCTCAAAGAGACA (SEQ ID NO: 49) | TGCACTTTCTGCTGGACATC (SEQ ID NO: 50) |
| CEBPA | GCGGGAACGCAACAACATC (SEQ ID NO: 51) | GTCACTGGTCAACTCCAGCAC (SEQ ID NO: 52) |
| CEBPB | CTTCAGCCCGTACCTGGAG (SEQ ID NO: 53) | GGAGAGGAAGTCGTGGTGC (SEQ ID NO: 54) |
| MGT1A1 | TAAGTGGCTACCCCAAAACG (SEQ ID NO: 55) | GCTTTGCATTGTCCATCTGA (SEQ ID NO: 56) |
| MGT1A3 | TCAGATGGACAATGCAAAGCGC (SEQ ID NO: 57) | GGCGCATGATGTTCTCCTTGTA (SEQ ID NO: 58) |
| PDX1 | TTAGGATGTGGACGTAATT (SEQ ID NO: 59) | GGTCAAGTTCAACATGACAG (SEQ ID NO: 60) |
| NKX6.1 | AGGACGACGACTACAATAAGCCTCT (SEQ ID NO: 61) | GCGCTGCTGGACTTGTGCTTCT (SEQ ID NO: 62) |
| NEUROG 3 | GGAGTCGGCGAAAGAAGGC (SEQ ID NO: 63) | TACAAGCTGTGGTCCGCTATG (SEQ ID NO: 64) |
| INSULIN | GCAGCCTTTGTGAACCAACAC (SEQ ID NO: 65) | CCCCGCACACTAGGTAGAGA (SEQ ID NO: 66) |

TABLE 8-continued

Primer sequences

| Gene name | Primer sequence (F: 5' -> 3') | Primer sequence (R: 5' -> 3') |
|---|---|---|
| SST | GCTGCTGTCTGAACCCAAC (SEQ ID NO: 67) | CGTTCTCGGGGTGCCATAG (SEQ ID NO: 68) |
| AMY2A | TTCAGACCTTGGTGGGAAAGA (SEQ ID NO: 69) | ACGAACCCCAACATTGTTACAT (SEQ ID NO: 70) |
| GLUCAGON | GACAAGCGCCATTCACAGG (SEQ ID NO: 71) | TGACGTTTGGCAATGTTATTCCT (SEQ ID NO: 72) |
| CDX2 | GGCAGCCAAGTGAAAACCAG (SEQ ID NO: 73) | GGTGATGTAGCGACTGTAGTAA (SEQ ID NO: 74) |
| MUC2 | TGCAGTGTGATGTCTCTGTTGGGT (SEQ ID NO: 75) | ATCCATGGGCCAGCAACAATTGAC (SEQ ID NO: 76) |
| VIL1 | AGCTCCTCTACAGGCTTGTTCACT (SEQ ID NO: 77) | GGACGTGTTCAATGCTAACAGCAACC (SEQ ID NO: 78) |
| CHGA | TGACCTCAACGATGCATTTC (SEQ ID NO: 79) | CTGTCCTGGCTCTTCTGCTC (SEQ ID NO: 80) |
| LYSO | CTTGTCCTCCTTTCTGTTACGG (SEQ ID NO: 81) | CCCCTGTAGCCATCCATTCC (SEQ ID NO: 82) |
| AQP5 | GCCATCCTTTACTTCTACCTGCTC (SEQ ID NO: 83) | GCTCATACGTGCCTTTGATGATGG (SEQ ID NO: 84) |
| CC-10 | TCATGGACACACCCTCCAGTTATGAG (SEQ ID NO: 85) | TGAGCTTAATGATGCTTTCTCTGGGC (SEQ ID NO: 86) |
| NKX2.1 | CGGCATGAACATGAGCGGCAT (SEQ ID NO: 87) | GCCGACAGGTACTTCTGTTGCTTG (SEQ ID NO: 88) |
| SPA | GTGCGAAGTGAAGGACGTTTGTGT (SEQ ID NO: 89) | TTTGAGACCATCTCTCCCGTCCC (SEQ ID NO: 90) |
| SPB | TCTGAGTGCCACCTCTGCATGT (SEQ ID NO: 91) | TGGAGCATTGCCTGTGGATGG (SEQ ID NO: 92) |
| SPC | CCTTCTTATCGTGGTGGTGGTGGT (SEQ ID NO: 93) | TCTCCGTGTGTTTCTGGCTCATGT (SEQ ID NO: 94) |
| PAX8 | ACTACAAACGCCAGAACCCTACCA (SEQ ID NO: 95) | TGTCATTGTCACAGACGCCCTCA (SEQ ID NO: 96) |
| TG | ACGGTTCCTCGCAGTTCAAT (SEQ ID NO: 97) | GCAGCTTGGAACATAGGGGT (SEQ ID NO: 98) |
| TSHR | AGCCACTGCTGTGCTTTTAAG (SEQ ID NO: 99) | CCAAAACCAATGATCTCATCC (SEQ ID NO: 100) |

(2) Experimental Methods and Results
(1) The immunofluorescence staining method was the same as described above.
(2) The Q-PCR method was the same as described above.
(3) Induced differentiation to hepatocytes
The specific method included the following steps of:
1. Collegan IV/Matrigel/Laminin/KM were mixed at a ratio of 1:3:1:5, then an appropriate volume of the mixed gel solution was uniformly coated to the well plate, which was dried at room temperature for 3-5 hours.
2. hiEndoPCs were manually picked and divided into small pieces with appropriate size and seeded into the above treated culture plates, and cultured using reprogramming medium for human gastric epithelial cells (hGECs) supplemented with 8% (V/V) of FBS and 10 uM of Y27632 (formulation: Advanced DMEM/F12+2 mM Glutamine+penicillin-streptomycin+SB431542 (2 μM)+RG108 (0.04 μM)+BIX01294 (0.5 μM)+Bay K 8644 (2 μM)) overnight.
3. After the cell clumps fully adhered, hiEndoPCs were induced to differentiate by a staged method. The first stage: cultured with KM (formulation see that in the first part of the Example)+25 ng/mL BMP4+25 ng/mL FGF4+50 ng/mL Wnt3a for 3 days; the second stage: cultured with HM (commercialized medium, purchased from ScienCell)+20 ng/mL HGF+10 ng/mL OSM+1 μM Dex for 10-15 days.
(4) Induction of Differentiation to Islet β Cells
The specific method included the following steps of:
1. Matrigel/KM were mixed at a ratio of 1:1, then an appropriate volume of the mixed gel solution was uniformly coated to the well plate, which was dried at room temperature for 3-5 hours. The cell adherence method was the same as described above.
2. The adhered cells were induced to differentiate to the pancreas according to four stages.
2.1 MCDB 131 medium (purchased from Gibco)+1.5 g/L of sodium bicarbonate+2 mM (concentration) 2 mM of Glutamax (Glutamine)+10 mM of final glucose concentration (glucose)+2% of BSA (bovine serum albumin)+0.25 mM of ascorbic acid (vitamin C)+50 ng/mL of FGF7 (fibroblast growth factor 7)+0.25 μM of SANT-1+1 μM of retinoic acid (RA)+100 nM of LDN193189+1:200 ITS-X (insulin-Transferrin-selenium-ethanolamine complex solution)+200 nM TPB, cultured for 2 days.
2.2 MCDB 131 medium+1.5 g/L of sodium bicarbonate+2 mM of Glutamax+10 mM of final glucose concentration+2% of BSA+0.25 mM of ascorbic acid+2 ng/mL of FGF7+0.25 μM of SANT-1+0.1 μM of retinoic acid+200 nM of LDN193189+1:200 ITS-X+100 nM of TPB, cultured for 2 days.
2.3 After 2 days, the cells in the second stage were digested with 5 mg/mL of dispase for 5 minutes at 37° C., then mechanically blown into small pieces and transferred to a low adsorption well plate, with medium changed: MCDB 131 medium+1.5 g/L of sodium bicarbonate+2 mM of Glutamax+20 mM of final glucose concentration+2% of BSA+0.25 μM of SANT-1+0.05 μM of retinoic acid+100 nM of LDN193189+1:200 ITS-X+1 μM of T3 (insulin-transferrin-selenium-ethanolamine complex solution)+10 μM of ALK5 inhibitor II+10 μM of zinc suLfate+10 μg/mL of heparin, and cultured for 3 days.
2.4 CMRL 1066+2 mM of Glutamax+2% of BSA+100 nM of LDN193189+1:200 ITS-X+1 μM of T3+10 of μM ALK5 inhibitor II+10 μM zinc sulfate+100 nM of γ-secretase inhibitor XX+2 μM of R428, cultured for 7 days or longer.
(5) Induced Differentiation to Intestinal Cells
The specific method included the following steps of:
1. RPMI 1640 medium+2 mM of Glutama+100 U/mL of penicillin+0.1 mg/mL of streptomycin+500 ng/mL of FGF4 (fibroblast growth factor 4)+500 ng/mL of Wnt3a (WNT signaling pathway protein ligand 3A)+100 ng/mL EGF (epidermal growth factor)+3 μM of CHIR99021 (Stemgent), cultured for 5 days.
2. The cells in the first stage were manually picked and mechanically blown into small pieces and then embedded in matrigel (artificial basement membrane) at 37° C. for 7-10 minutes. The medium was added thereto after solidification: Advanced DMED/F12+2 mM of Glutamax+100 U/mL of penicillin+0.1 mg/mL of streptomycin+1% of N2 (serum-free nerve cell additive N2)+1% of B27 (serum-free nerve cell additive B27)+100 ng/mL of EGF (epidermal growth factor)+100 ng/mL of Noggin, and cultured for more than 1 week.

(6) Induced Differentiation to the Thyroid

The specific method included the following steps of:

1. Advanced DMEM/F12+L-Glutamax+B27 (1%)+N2 (1%)+Noggin (200 ng/mL)+SB431542 (10 μM) for 3 days.

2. Advanced DMEM/F12+L-Glutamax+B27 (1%)+N2 (1%)+Wnt3a (100 ng/mL)+EGF (20 ng/mL)+BMP4 (10 ng/mL)+FGF10 (10 ng/mL)+FGF7 (10 ng/mL)+TSH (1 μg/mL) for 3 days.

3. Advanced DMEM/F12+L-Glutamax+B27 (1%)+N2 (1%)+TSH (1 μg/mL)+IGF (50 ng/mL)+insuLin (5 mg/mL)+NaI (100 μM) for 4 days.

(7) Induced Differentiation to the Lung

The specific method included the following steps of:

1. Advanced DMEM/F12+L-Glutamax+B27 (1%)+N2 (1%)+Noggin (200 ng/mL)+SB431542 (10 μM) for 4 days.

2. Advanced DMEM/F12+L-Glutamax+B27 (1%)+N2 (1%)+Wnt3a (100 ng/mL), EGF (20 ng/mL)+BMP4 (10 ng/mL)+FGF10 (10 ng/mL)+FGF7 (10 ng/mL) for 3 days.

3. Advanced DMEM/F12+L-Glutamax+B27 (1%)+N2 (1%)+Wnt3a (100 ng/mL)+FGF10 (10 ng/mL)+FGF7 (10 ng/mL)+Dexamethasone (50 nM) for 3 days.

(8) ELISA Detection of C Peptide Content

The protocol was performed according to the requirements on the C-peptide ELISA kit. The specific method included the following steps of:

1. Preparation of working solution: The reagents in the kit were diluted into working solutions according to the instructions in advance, and equilibrated at room temperature for 20 minutes.

2. Preparation of standard samples: 1 mL of deionized water was added to each of the 5 standard samples, mixed well and packed into small samples, and stored at −20° C. in the refrigerator.

3. The standard samples and the cell supernatant samples to be tested were respectively added to a 96-well plate coated with c-peptide antibody, each well of 25 μL, three replicates for each sample.

4. 50 μL of buffer was added to each well.

5. The 96-well plate was placed on a microporous shaker and incubated for 1 hour at 800 rpm.

6. The liquid in the 96-well plate was discarded, 350 μL of washing buffer was added to each well, then the washing solution was poured off, and blotted with the filter paper, and repeated for 4-5 times.

7. 200 μL of Enzyme conjugate solution was added to each well.

8. The well plate was placed on a microporous shaker and incubated at room temperature for 1 hour at 800 rpm.

9. The liquid was discarded and 350 μL of washing buffer was added to each well, and the step 6 was repeated.

10. 200 μL of substrate TMB (tetramethylbenzidine) was added to each well.

11. The well plate was placed on a shaker and incubated at room temperature for 30 minutes in the dark.

12. 50 μL of stop solution was added to each well, and shook on a shaker for 5 seconds in the dark.

13. The OD value was measured at a wavelength of 450 nm on a microplate reader within 30 minutes, and the results were calculated.

9) Dithizone (DTZ) Staining

The specific method included the following steps of:

1. DTZ stock solution (purchased from Sigma) was diluted at a ratio of 1:20, and then filtered through a 0.45 μm of filter membrane to prepare a working solution.

2. The cells to be stained were washed with PBS. 3. The prepared DTZ working solution was added to the cells to be stained, the cells were incubated at 37° C. for 10 min, and observed and photographed under the microscope.

(10) Statistical Analysis

All data was obtained from 3 or more independent experiments, and the data was described as mean±standard deviation unless otherwise stated. Statistical analysis between the two groups of data was performed using the SPSS software for the two-tailed t-test. The difference between the two groups was considered statistically significant at $P<0.05$.

RESULTS: Endodermal progenitor cells eventually developed into organs such as the pancreas, liver, intestines, lungs and thyroid in vivo. To confirm that hiEndoPCs were endodermal progenitor cells, the present invention tested their potential to be induced differentiation in multiple directions.

Figures 33A, 33B, 33C, 33D, 33E, 33F:
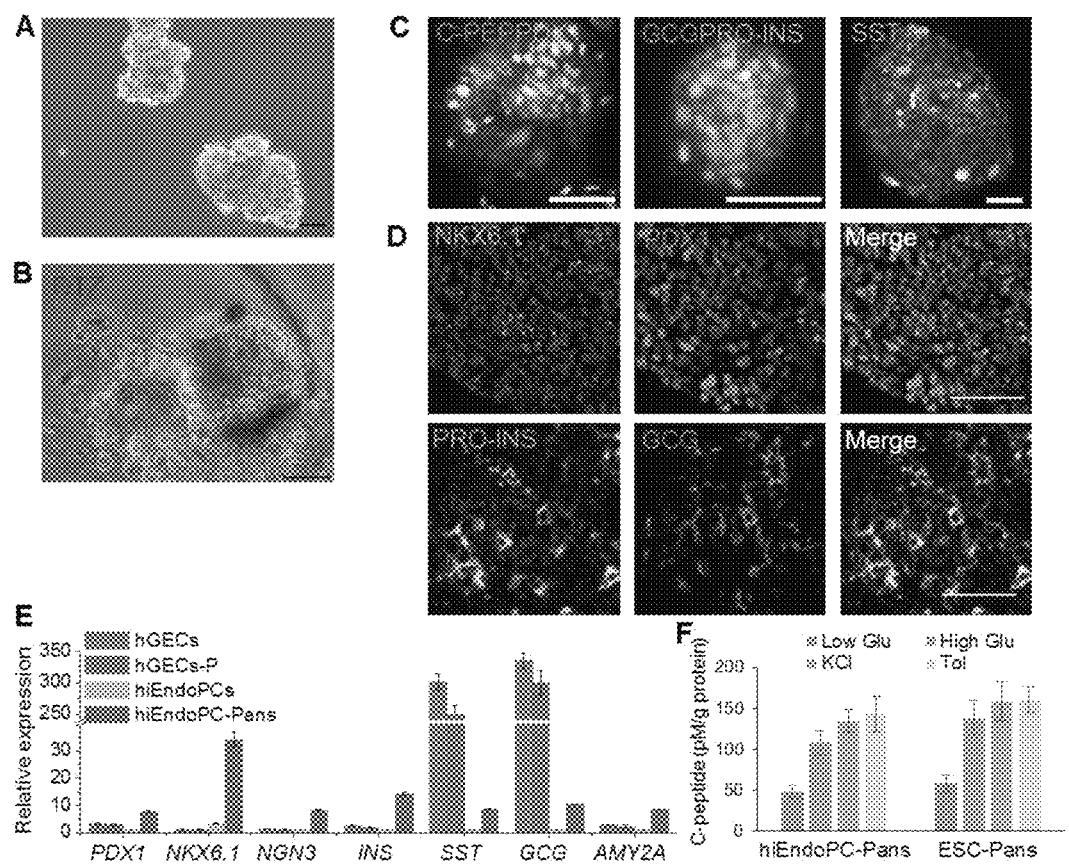
FIGS. 33A-33F show the results of differentiation of hiEndoPCs into the pancreas, A is a three-dimensional morphology map of hiEndoPC-Pans; B is a histioPC-Pans DTZ staining map; C and D are hiEndoPC-Pans pancreas-specific protein expression maps (scale: 50 μm); E is the pancreatic specific gene expression map of hiEndoPC-Pans; F is the insulin release response map of hiEndoPC-Pans.

(1) Induced Differentiation of Endodermal Progenitor Cells (hiEndoPCs) to the Pancreas In accordance with the classical pancreas induced differentiation protocol [Pagliuca Felicia W, Millman Jeffrey R, Gürtler M, Segel M, Van Dervort A, Ryu Jennifer H, et al. Generation of Functional Human Pancreatic β Cells In Vitro. Cell. 2014; 159:428-39. Rezania A, Bruin J E, Arora P, Rubin A, Batushansky I, Asadi A, et al. Reversal of diabetes with insuLin-producing cells derived in vitro from human pluripotent stem cells. Nat Biotechnol. 2014; 32:1121-33.], hiEndoPCs were induced to differentiate to the pancreas. After 2 weeks of induction, hiEndoPCs derived pancreatic cells (hiEndoPC-Pans) exhibited three-dimensional sprouting morphology of islets in vivo (FIG. 33A). DTZ (dithizone) staining showed that hiEndoPC-Pans appeared red, indicating that the cytoplasm of the cells contained zinc ions, which was characteristic of islet β cells (FIG. 33B). Pancreatic specific protein staining of hiEndoPC-Pans showed significant expression of pancreatic specific transcription factors PDX1 and NKX6.1, islet α cell marker GCG, islet β cell marker C-PEP and PRO-INS, and islet δ cell marker SST (FIGS. 33C and 33D). Analysis of transcriptional levels revealed that various pancreatic characteristic genes were upregulated after induction (FIG. 33E), which was consistent with immunostaining results. To confirm whether hiEndoPCs-Pans had the most important ability to synthesize and release insulin from islet β cells, the ability of hiEndoPCs-Pans to release C-peptide under various stimulating conditions was examined. When stimulated with high glucose, the release of C-peptide was significantly increased compared to the low-sugar group. When other insulin secretion promoters KCL and Tolbutamiden were used, the release of C peptide was also significantly increased. Moreover, the insulin release response of hiEndoPCs-Pans to stimuli was comparable to that of ESCs derived islet cells (FIG. 33F). The sugar-stimulated reactivity of hiEndoPCs-Pans had important clinical application significance for the treatment of diabetic hyperglycemia in the future.

(2) Induced differentiation of hiEndoPCs to intestinal cells

Figures 34A, 34B, 34C:
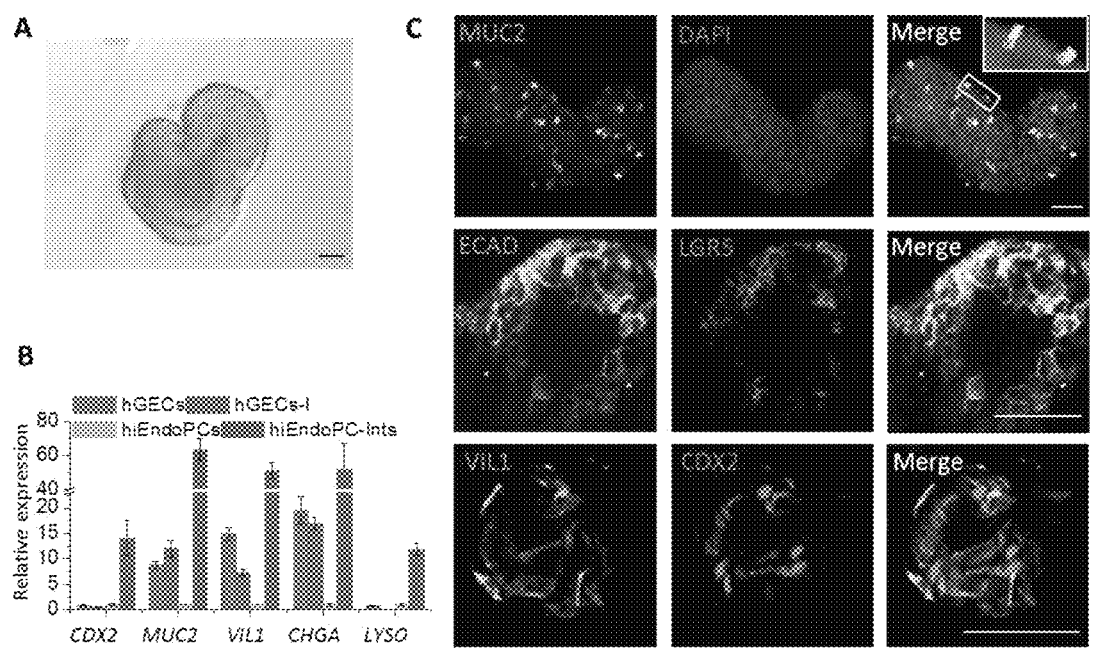
FIG. 34A-34C show the results of differentiation of hiEndoPCs into the intestine, A is the morphology map of hiEndoPC-Ints; B is the intestinal-specific gene expression map of hiEndoPC-Ints; C is the intestinal specific protein staining map of hiEndoPC-Ints (scale: 50 μm)

In accordance with the classical intestinal cell induction protocol[Spence J R, Mayhew C N, Rankin S A, Kuhar M F, Vallance J E, Tolle K, et al. Directed differentiation of human pluripotent stem cells into intestinal tissue in vitro. Nature. 2010; 470:105-9. Watson C L, Mahe M M, Múnera J, Howell J C, Sundaram N, Poling H M, et al. An in vivo model of human small intestine using pluripotent stem cells. Nature Medicine. 2014; 20:1310-4.], hiEndoPCs was detected for differentiation to intestinal tract. After 2 weeks of induction, hiEndoPCs derived intestinal organoid (hiEndoPC-Ints) was found to exhibit morphological characteristics of primary intestinal culture in vitro (FIG. 34A). The expression of intestinal specific transcription factor CDX2, small intestinal cell marker VIL1, goblet cell marker MUC2, small intestinal endocrine cell marker CHGA, and small intestinal Paneth's cell marker LYSO in hiEndoPC-Ints were significantly upregulated after induction (FIG. 34B). Moreover, at the protein level, the intestinal characteristic markers, VIL1, MUC2, CDX2, LGR5, and ECAD were also significantly expressed (FIG. 34C), confirming that hiEndoPC-Ints had initially possessed characteristics of the intestine.

(3) Induced Differentiation of hiEndoPCs to Hepatocytes

Using the classical liver induction protocol [Gouon-Evans V, Boussemart L, Gadµe P, Nierhoff D, Koehler C I, Kubo A, et al. BMP-4 is required for hepatic specification of mouse embryonic stem cell-derived definitive endoderm. Nat Biotechnol. 2006; 24:1402-111 HiEndoPCs were induced to differentiate to hepatocytes, and hiEndoPCs derived hepatocytes (hiEndoPC-Heps) were found to begin to express multiple functional genes with characteristic of primary hepatocytes including HNF4A, CEBPA, CEBPB, TF, AATGGT, G6PC, CYP1A1, CYP3A4, CYP3A7, MGT1A1, MGT1A3, and the like (FIG. 35A). At the same time, the staining of AFP (alpha-fetoprotein) and CK18 (cytokeratin 18) were positive in hiEndoPC-Heps (FIG. 35B); the proportion of ALB (albumin)-positive cells at the flow level was as high as 90% or more (FIG. 35C), indicating that hiEndoPC-Heps had initially possessed characteristics of the hepatocytes.

(4) Induced differentiation of hiEndoPCs to the thyroid and lung After induced differentiation of hiEndoPCs to the thyroid [Longmire T A, Ikonomou L, Hawkins F, ChristodouLou C, Cao Y, Jean J C, et al. Efficient derivation of purified lung and thyroid progenitors from embryonic stem cells. Cell Stem Cell. 2012; 10:398-411.], the expression levels of specific transcription factor NKX2.1 shared by thyroid and lung, thyroid specific transcription factor Pax8, thyroglobulin (Tg), and thyroid stimulating hormone receptor (TSHR) in hiEndoPCs derived thyroid cells (hiEndoPCs-Thyroid) were very significantly improved compared to that before induction (FIG. 36A). The expression of lung specific transcription factor NKX2.1, lung Clare cell marker CC-10, aquaporin AQP5 as a marker of type I alveolar cells, and surface active protein SPA, SPB and SPC as markers of type II alveolar cells, in hiEndoPCs-derived lung cells (hiEndoPCs-Lung) were significantly upregulated (FIG. 36 B).

The endocytic differentiation potential of hiEndoPCs was identified by the strategy of promoting differentiation to pancreas, liver, intestine, thyroid and lung. The results showed that after the differentiation of hiEndoPCs in five directions, the expression of related genes and protein expression were significantly improved. The partial function had also appeared, more clearly confirmed that hiEndoPCs were endodermal progenitor cells, and suggested that hiEndoPCs could provide ideal seed cells for cell therapy of diabetes, liver disease and intestinal diseases, and the like.

Example 3. A Small Molecule Compound Combination for Reprogramming Digestive Tract Derived Epithelial Cells to Endodermal Stem/Progenitor Cells Effect of changing the concentration of individual small molecule in small molecule combination 4M on production of induced endodermal progenitor cells: as described above, in the BBRS small molecule combination of four small molecule compounds, under the condition of four small molecules with concentration used of SB431542 (SB, 2 µM), RG108 (RG, 0.04 µM), Bix01294 (Bix, 0.5 µM), Bay K 8644 (Bay, 2 µM), the endodermal progenitor cells (hiEndoPCs) could be obtained by reprogramming with an efficiency of 4-6%. In this Example, using the same method, under the condition of four small molecules with different concentration ranges of SB431542 (1 to 10 µM), RG108 (0.01 to 1 µM), Bix01294 (0.1 to 2 µM), Bay K 8644 (1 to 4 µM), the production of hiEndoPCs was verified (see Table 9), and at the same time, after replacing SB with A83-01 (A83, 0.4 to 1 µM), the production of hiEndoPCs was verified under the condition of A83-01 (A83, 0.4 to 1 µM) combined with other three small molecules with different concentrations of RG108 (0.01 to 1 µM), Bix01294 (0.1 to 2 µM), Bay K 8644 (1 to 4 µM) (Table 10).

TABLE 9

Efficiency for obtaining hiEndoPCs by BBRS small molecule combinations with different concentrations used and reprogramming thereof

| Exp. No. | SB value (µM) | RG value (µM) | Bix value (µM) | Bay value (µM) | Formation efficiency of hiEndoPCs |
|---|---|---|---|---|---|
| Combination 1 | 1 | 0.01 | 0.1 | 1 | 3.2% |
| Combination 2 | 1 | 0.01 | 0.1 | 4 | 3.6% |
| Combination 3 | 5 | 0.01 | 2 | 1 | 2.3% |
| Combination 4 | 5 | 0.1 | 2 | 4 | 2.9% |
| Combination 5 | 5 | 0.1 | 0.1 | 1 | 3.4% |
| Combination 6 | 5 | 0.1 | 0.5 | 4 | 3.7% |
| Combination 7 | 1 | 0.1 | 0.5 | 1 | 3.5% |
| Combination 8 | 1 | 1 | 0.5 | 4 | 3.1% |
| Combination 9 | 10 | 0.01 | 0.5 | 2.5 | 4.1% |
| Combination 10 | 10 | 0.01 | 0.1 | 2.5 | 4.7% |
| Combination 11 | 5 | 0.01 | 2 | 2.5 | 4.3% |
| Combination 12 | 10 | 0.01 | 2 | 2.5 | 4.5% |
| Combination 13 | 10 | 1 | 0.1 | 1 | 4.2% |
| Combination 14 | 10 | 1 | 0.1 | 4 | 4.8% |
| Combination 15 | 10 | 1 | 2 | 1 | 3.8% |
| Combination 16 | 10 | 1 | 2 | 4 | 3.9% |

TABLE 10

Efficiency for obtaining hiEndoPCs by BBRA small molecule combinations with different concentrations used and reprogramming thereof

| | A83 value (µM) | RG value (µM) | Bix value (µM) | Bay value (µM) | Formation efficiency of hiEndoPCs |
|---|---|---|---|---|---|
| Combination 1 | 0.4 | 0.01 | 0.1 | 1 | 4.1% |
| Combination 2 | 0.4 | 0.01 | 0.1 | 4 | 4.3% |
| Combination 3 | 0.4 | 0.01 | 2 | 1 | 4.2% |
| Combination 4 | 0.4 | 0.01 | 2 | 4 | 4.6% |
| Combination 5 | 0.4 | 1 | 0.1 | 1 | 4.7% |
| Combination 6 | 0.7 | 1 | 0.1 | 4 | 5.1 |
| Combination 7 | 0.7 | 0.1 | 2 | 1 | 5.2% |
| Combination 8 | 0.7 | 0.1 | 2 | 4 | 5.5% |
| Combination 9 | 0.7 | 0.1 | 0.5 | 1 | 5.3% |
| Combination 10 | 1 | 0.1 | 0.5 | 4 | 5.7% |
| Combination 11 | 1 | 0.01 | 0.5 | 1 | 5.9% |
| Combination 12 | 1 | 0.01 | 0.5 | 2.5 | 6.0% |
| Combination 13 | 0.7 | 1 | 0.1 | 2.5 | 5.8% |
| Combination 14 | 1 | 1 | 0.1 | 2.5 | 6.1% |
| Combination 15 | 1 | 1 | 2 | 2.5 | 5.4% |
| Combination 16 | 1 | 1 | 2 | 4 | 5.6% |

The endodermal related gene, protein, epigenetic modification and differentiation function of endodermal progenitor cells obtained in the combination of Table 9 and Table 10 were determined by the method of Example 2. The results showed that the induced endoderms obtained by the above combination highly expressed the endodermal progenitor cell characteristic markers FOXA2, SOX9, GATA4, HNF1B, HOXA3, PDX1, CXCR4, EPCAM, CK19 and LGR5, and did not express the gastric cell characteristic markers MUC6 and GAST. It had the endodermal progenitor cell characteristics of epidermal modification, and could express hepatocyte specific markers AFP, ALB, HNF4A, CK18, CYP3A4, and the like after differentiation to hepatocytes; Pancreas specific markers such as NKX6.1, PDX1, GCG, SST, and INS were expressed after differentiation to pancreatic β cells, and insulin could be released under stimulating conditions; intestinal specific markers such as CDX2, MUC2, VIL1, CHGA, and LYSO were expressed after inducted differentiation to intestinal cells; after differentiation to lung and thyroid cells, they expressed respective cell-specific markers. It was confirmed that the endodermal progenitor cells were also obtained by the small molecules in the concentration range listed in Table 9-Table 10.

Example 4. Preparation of a Reprogramming Kit for Reprogramming Digestive Tract Derived Epithelial Cells to Endodermal Stem/Progenitor Cells The present invention provided a reprogramming kit for reprogramming digestive tract derived epithelial cells to endodermal stem/progenitor cells, comprising a small molecule compound combination for reprogramming digestive tract derived epithelial cells to endodermal stem/progenitor cells, specifically, a small molecule compound combination consisting of 8 small molecule compounds (8M), FBP (Fructose diphosphate), Bay K 8644, Bix01294, SB431542 or A83-01, Valproic Acid (VPA), RG108, PD0325901 and PS48, respectively.

A preferred small molecule compound combination for reprogramming digestive tract derived epithelial cells to endodermal stem/progenitor cells comprised the following 4 small molecule compounds, wherein the BBRS combination was Bix01294 (Bix), Bay K 8644 (Bay), RG108 (RG), and SB431542 (SB). BBRA combination was Bix01294 (Bix), Bay K 8644 (Bay), RG108 (RG) and A83-01 (A83).

In the kit, each compound could be packaged separately, or each compound could be mixed and packaged according to 8M combination or BBRS combination or BBRA combination; when the compounds were separately packaged, the concentration used of each compound was described in the instructions of the kit, and the specific values of concentration could be referred to Example 1 and Example 3.

The kit further comprised basal medium, Advanced DMEM/F12 and basal additive component for cell culture, Glutamine (Glutamax) and Antibiotic SP, and instructions for use thereof, wherein Glutamine was used at a concentration of 2 mM (1×) relative to Advanced DMEM/F12 basal medium, Antibiotics (eg, penicillin-streptomycin) were used at a concentration of 100 U/mL of penicillin+0.1 mg/mL of streptomycin, and the ingredients were packaged separately or mixed according to the listed concentration.

The kit could be further combined with the small molecule compound combination and the basal medium and the basal additive component for cell culture to form a reprogramming medium, and the reprogramming medium was formulated as: Advanced DMEM/F12+2 mM of Glutamine (Glutamax)+penicillin-streptomycin (100 U/mL of penicillin+0.1 mg/mL of streptomycin)+SB431542 (2 µM) or A83-01 (0.5 µM)+VPA (0.5 mM)+PD0325901 (0.5 µM)+RG108 (0.04 µM)+Bix01294 (0.5 µM)+Bay K 8644 (2 µM)+PS48 (5 µM)+FBP (3.5 mM).

A preferred reprogramming medium was formulated as: Advanced DMEM/F12 containing 2 mM of Glutamine (Glutamax), penicillin-streptomycin (100 U/mL of penicillin and 0.1 mg/mL of streptomycin), 1 to 10 µM of SB431542, 0.01 to 1 µM of RG108, 0.1 to 2 µM of Bix01294, 1 to 4 µM of Bay K 8644; more preferably, Advanced DMEM/F12 containing 2 mM of Glutamine (Glutamax), penicillin-streptomycin (100 U/mL of penicillin and 0.1 mg/mL of streptomycin), 2 µM of SB431542, 0.04 µM of RG108, 0.5 M of Bix01294, 2 µM of Bay K 8644.

Another preferred reprogramming medium was formulated as: Advanced DMEM/F12 containing 2 mM of glutamine (Glutamax), penicillin-streptomycin (100 U/mL of penicillin and 0.1 mg/mL of streptomycin), 0.4-1 µM of A83-01, 0.01 to 1 µM of RG108, 0.1 to 2 µM of Bix01294, 1 to 4 µM of Bay K 8644; more preferably, Advanced DMEM/F12 containing 2 mM of glutamine (Glutamax), penicillin-streptomycin (100 U/mL of penicillin and 0.1 mg/mL of streptomycin), 0.5 µM of A83-01, 0.04 µM of RG108, 0.5 M of Bix01294, 2 µM of Bay K 8644.

The kit could further include trophoblast cells and instructions for use thereof, the trophoblast cells being digestive tract derived stromal cells, such as gastric subepithelial myofibroblasts or intestinal subepithelial myofibroblasts.

All of the cells, compounds and reagents in the kit were commercially available from the sources suggested in the previous examples.

The kit further included instructions for use, which described the actual composition and method for use of the kit, including the reprogramming method for reprogramming of digestive tract derived epithelial cells to endodermal stem/progenitor cells using related reagents, the content of which referred to the description in the examples.

INDUSTRIAL APPLICABILITY

The present invention provides a small molecule compound combination for reprogramming digestive tract derived epithelial cells to endodermal stem/progenitor cells, a reprogramming method and an application. Human gastric epithelial cells (hGECs) are used as initiating cells, human gastric subepithelial myofibroblasts (aGSEMFs) are used as a trophoblast, a compound combination having all or a plurality of FBP, Bay K 8644, Bix01294, SB431542 or A83-01, VPA, RG108, PD0325901 and PS48 including SB or A83 is used to reprogram digestive tract derived epithelial cells to endodermal stem/progenitor cells, and the endodermal stem/progenitor cells can be used for inducing differentiation towards liver cells, pancreatic beta cells and intestinal cells. The present invention can be applied industrially.

The invention claimed is:

1. A small molecule compound combination for reprogramming digestive tract derived epithelial cells to endodermal stem/progenitor cells, the small molecule compound is selected from the group consisting of TGF-β signaling pathways, epigenetic modulators, $Ca^{2+}$ channel activators, and metabolic regulators, and the like functional groups; typically, a combination including all 8 small molecule compounds of FBP, Bay K 8644 (Bay), Bix01294 (Bix), SB431542 (SB) or A83-01 (A83), VPA, RG108 (RG), PD0325901, and PS48 (8M), or a combination including or a plurality of the 8M on the premise of SB or A83.

2. The reprogramming small molecule compound combination according to claim 1, wherein, the combination including 8 small molecule compounds is: a combination of SB43154: VPA: PD0325901: RG108: Bix01294: Bay K 8644: PS48: FBP in a molar ratio of 50:12500:12.5:1:12.5:50:125:87500; or a combination of A83: VPA: PD0325901: RG108: Bix01294: Bay K 8644: PS48: FBP in a molar ratio of 12.5:12500:12.5:1:12.5:50:125:87500.

3. The reprogramming small molecule compound combination according to claim 1, wherein, the small molecule compounds were Bix01294 (Bix), Bay K 8644 (Bay), RG108 (RG), SB431542 (SB) and A83-01 (A83), which form two combinations: a combination including 4 small molecule compounds is: Bix01294 (Bix), Bay K 8644 (Bay), RG108 (RG), and SB431542 (SB), referred to as BBRS combination, or Bix01294 (Bix)-, Bay K 8644 (Bay), RG108 (RG), and A83-01 (A83), referred to as BBRA combination.

4. The reprogramming small molecule compound combination according to claim 3, wherein, each compound in the combinations is used at a concentration of SB43152 of 1 to 10 μM, A83 of 0.4 to 1 μM, RG108 of 0.01 to 1 μM, Bix01294 of 0.1 to 2 μM, Bay K 8644 of 1 to 4 μM.

5. The reprogramming small molecule compound combination according to claim 3, wherein, the BBRS combination is a combination of each compound of SB: RG: Bix: Bay in a molar ratio of 50:1:12.5:50, and the BBRA combination is a combination of each compound of A83: RG: Bix: Bay in a molar ratio of 12.5:1:12.5:50.

6. A reprogramming kit for reprogramming digestive tract derived epithelial cells into endodermal stem/progenitor cells, includes the reprogramming small molecule compound combination according claim 2, and instructions for use of the compounds; each compound is packaged separately, or each compound is packaged according to the BBRS combination with SB: RG: Bix: Bay at molar ratio of 50:1:12.5:50 or the BBRA combination with A83: RG: Bix: Bay at molar ratio of 12.5:1:12.5:50, and the concentration of each compound used is described in the instructions.

7. The reprogramming kit according to claim 6, wherein, further includes feeder cells and instructions for use thereof, the feeder cells are digestive tract derived stromal cells, such as gastric subepithelial myofibroblasts or intestinal subepithelial myofibroblasts.

8. The reprogramming kit according to claim 6, wherein, further includes basal medium, Advanced DMEM/F12, basal components for cell culture, Glutamine (Glutamax) and Antibiotic (SP), and instructions for use thereof, wherein Glutamine is used at a concentration of 2 mM (1×) relative to Advanced DMEM/F12 basal medium, the Antibiotic is penicillin-streptomycin, penicillin is used at a concentration of 100 U/mL and streptomycin is used at a concentration of 0.1 mg/mL relative to Advanced DMEM/F12basal medium, and each substance is packaged separately or mixed according to the listed concentration.

9. The reprogramming small molecule compound combination according to claim 3, wherein, the small molecule compound combination is dissolved in a basal medium to form a reprogramming medium, which is formulated as:

Advanced DMEM/F12 or Advanced 1640 medium containing 1 to 10 µM of SB43152, 0.01 to 1 µM of RG108, 0.1 to 2 µM of Bix01294, 1 to 4 µM of Bay K 8644; preferably, Advanced DMEM/F12 containing 2 µM of SB43152, 0.04 µM of RG108, 0.5 M of Bix01294, 2 µM of Bay K 8644.

10. The reprogramming small molecule compound combination according to claim 3, wherein, the small molecule compound combination is dissolved in a basal medium to form a reprogramming medium, which is formulated as: Advanced DMEM/F12 or Advanced 1640 medium containing 0.4-1 µM of A83-01, 0.01 to 1 µM of RG108, 0.1 to 2 µM of Bix01294, 1 to 4 µM of Bay K 8644; preferably, Advanced DMEM/F12 containing 0.5 µM of A83-01, 0.04 µM of RG108, 0.5 M of Bix01294, 2 µM of Bay K 8644.

11. A method for reprogramming digestive tract derived epithelial cells to endodermal stem/progenitor cells, comprises the following steps of:
1) using the isolated primary digestive tract derived epithelial cells as starting cells and expanding the digestive tract derived epithelial cells;
2) treating the feeder cells with mitomycin-C, washing, and digesting the cells with enzymes for later use;
3) adding the feeder cells prepared in the step 2) to the digestive tract derived epithelial cells cultured and expanded in step 1), and continuing co-culture overnight;
4) adding a reprogramming medium containing the reprogramming small molecule compound combination according to claim 3 on day 2, refreshing the medium every 2-3 days, and culturing for 7-15 days to obtain colony of induced endoderm stem/progenitor cells (hiEndoPCs).

12. The method according to claim 11, wherein, the starting cells in the step 1) are digestive tract derived epithelial cells, including gastric epithelial cells and duodenal epithelial cells, preferably gastric epithelial cells (hGECs), and particularly preferably NCAM (neural cell adhesion molecule) positive gastric epithelial cells (hGECs);
in the step 1), NCAM positive gastric epithelial cells are preferably used as starting cells, and cultured in Kubota medium at 37° C. in a 5% $CO_2$ incubator for 5 days.

13. The method according to claim 11, wherein, the feeder cells in the step 2) are digestive tract derived stromal cells, including gastric subepithelial myofibroblasts or intestinal subepithelial myofibroblasts, preferably human gastric subepithelial myofibroblasts (aGSEMFs);
in the step 2), human gastric subepithelial myofibroblasts (aGSEMFs) are preferably treated with mitomycin-C for 2-3 hours, then the cells are washed with PBS, and the cells are digested with TrypLE enzyme.

14. The method according to claim 11, wherein, in the step 3), the feeder cells prepared in the step 2) are preferably added at a density of 1 to $3\times10^5$ per square centimeter to the digestive tract derived epithelial cells cultured for 5 days in the step 1), and cultured at 37° C. in a 5% $CO_2$ incubator overnight (12-16 hours).

15. The method according to claim 11, wherein, the method further comprises the process for passage of the endodermal stem/progenitor cells (hiEndoPCs), comprising the following steps of:
(1) preparation before passage: seeding the adult human gastric subepithelial myofibroblasts (aGSEMFs) treated with mitomycin-C (10 µg/mL) in a well plate, or about 3 hours in advance, coating the well plate with Fibronectin (FN), Cell-TAK (CT, cell tissue adhesive) gel and dring at room temperature;
(2) preparation of medium for passage: Advanced DMEM/DF12+AWF (A83-01 0.5 µM+Wnt3a 50 ng/mL+bFGF 10 ng/mL), or Advanced DMEM/DF12+A (A83-01, 0.5 µm);
(3) picking the colony of endodermal stem/progenitor cells (hiEndoPCs) and dividing them into small pieces at a ratio of about 1:3-4, placing them in FN+AWF, CT+AWF or, Feeder [feeder cells, adult human gastric subepithelial myofibroblasts (aGSEMFs) treated with mitomycin-C (10 µg/mL)]+A medium at 37° C. in a 5% $CO_2$ incubator to subculture so as to obtain passaged endodermal stem/progenitor cells.

16. The method according to claim 15, wherein, the method further comprises the process of the passaged endodermal stem/progenitor cells (hiEndoPCs) for differentiation into liver cells, pancreatic β cells, and intestinal cells.

17. The reprogramming small molecule compound combination according to claim 3, wherein, each compound is used at a concentration of SB43152 of 2 µM, A83 of 0.5 µM, RG108 of 0.04 M, Bix01294 of 0.5 µM, and Bay K 8644 of 2 µM.

18. The reprogramming kit according to claim 7, wherein, further includes basal medium, Advanced DMEM/F12, basal components for cell culture, Glutamine (Glutamax) and Antibiotic (SP), and instructions for use thereof, wherein Glutamine is used at a concentration of 2 mM (1×) relative to Advanced DMEM/F12 basal medium, the Antibiotic is penicillin-streptomycin, penicillin is used at a concentration of 100 U/mL and streptomycin is used at a concentration of 0.1 mg/mL relative to Advanced DMEM/F12basal medium, and each substance is packaged separately or mixed according to the listed concentration.

19. The method according to claim 11, wherein, the reprogramming medium in the step 4) is formulated as: Advanced DMEM/F12 or Advanced 1640 medium containing 1 to 10 µM of SB43152, 0.01 to 1 µM of RG108, 0.1 to 2 µM of Bix01294, 1 to 4 µM of Bay K 8644; preferably, Advanced DMEM/F12 containing 2 µM of SB43152, 0.04 µM of RG108, 0.5 M of Bix01294, 2 µM of Bay K 8644; or
the reprogramming medium in the step 4) is formulated as: Advanced DMEM/F12 or Advanced 1640 medium containing 0.4-1 µM of A83-01, 0.01 to 1 µM of RG108, 0.1 to 2 µM of Bix01294, 1 to 4 µM of Bay K 8644; preferably, Advanced DMEM/F12 containing 0.5 µM of A83-01, 0.04 µM of RG108, 0.5 M of Bix01294, 2 µM of Bay K 8644.

* * * * *